US012648948B2

(12) United States Patent
Habib

(10) Patent No.: US 12,648,948 B2
(45) Date of Patent: Jun. 9, 2026

(54) METHODS AND COMPOSITIONS FOR TREATING CANCER

(71) Applicant: UNITED STATES GOVERNMENT AS REPRESENTED BY THE DEPARTMENT OF VETERANS AFFAIRS, Washington, DC (US)

(72) Inventor: Amyn Habib, Dallas, TX (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 1007 days.

(21) Appl. No.: 17/701,634

(22) Filed: Mar. 22, 2022

(65) Prior Publication Data

US 2022/0211706 A1    Jul. 7, 2022

Related U.S. Application Data

(62) Division of application No. 15/940,802, filed on Mar. 29, 2018, now Pat. No. 11,285,154.

(60) Provisional application No. 62/478,500, filed on Mar. 29, 2017.

(51) Int. Cl.
| | |
|---|---|
| *A61K 31/517* | (2006.01) |
| *A61K 31/17* | (2006.01) |
| *A61K 31/277* | (2006.01) |
| *A61K 31/416* | (2006.01) |
| *A61K 31/4178* | (2006.01) |
| *A61K 31/4439* | (2006.01) |
| *A61K 31/454* | (2006.01) |
| *A61K 31/498* | (2006.01) |
| *A61K 31/4985* | (2006.01) |
| *A61K 31/502* | (2006.01) |
| *A61K 31/573* | (2006.01) |
| *A61K 31/713* | (2006.01) |
| *A61K 38/17* | (2006.01) |
| *A61K 45/06* | (2006.01) |
| *A61P 35/00* | (2006.01) |
| *C07K 16/24* | (2006.01) |

(52) U.S. Cl.
CPC ........... *A61K 31/517* (2013.01); *A61K 31/17* (2013.01); *A61K 31/277* (2013.01); *A61K 31/416* (2013.01); *A61K 31/4178* (2013.01); *A61K 31/4439* (2013.01); *A61K 31/454* (2013.01); *A61K 31/498* (2013.01); *A61K 31/4985* (2013.01); *A61K 31/502* (2013.01); *A61K 31/713* (2013.01); *A61K 38/1793* (2013.01); *A61K 45/06* (2013.01); *A61P 35/00* (2018.01); *C07K 16/241* (2013.01); *A61K 31/573* (2013.01); *C07K 2317/76* (2013.01)

(58) Field of Classification Search
CPC .......................... A61K 2300/00; A61K 45/06
See application file for complete search history.

(56) References Cited

U.S. PATENT DOCUMENTS

| | | | |
|---|---|---|---|
| 5,747,498 A | 5/1998 | Schnur et al. | |
| 7,947,653 B1 | 5/2011 | Sordella et al. | |
| 8,946,235 B2 | 2/2015 | Butterworth | |
| 9,180,129 B2 * | 11/2015 | Gilmer ................... | A61P 13/08 |
| 11,285,154 B2 | 3/2022 | Habib | |
| 2001/0003885 A1 | 6/2001 | Lum et al. | |
| 2004/0147428 A1 | 7/2004 | Pluenneke | |
| 2011/0301194 A1 | 12/2011 | Chan et al. | |
| 2011/0313010 A1 | 12/2011 | Recinos et al. | |
| 2012/0022098 A1 | 1/2012 | Ibrahim et al. | |
| 2012/0141479 A1 | 6/2012 | Witta et al. | |
| 2016/0136284 A1 | 5/2016 | Gill et al. | |
| 2017/0027951 A1 | 2/2017 | Klampfer | |
| 2017/0106059 A1 | 4/2017 | Modiano et al. | |
| 2017/0107577 A1 | 4/2017 | Al-Ejeh | |
| 2018/0057606 A1 | 3/2018 | Old et al. | |
| 2018/0264129 A1 | 9/2018 | Chang et al. | |
| 2019/0016808 A1 | 1/2019 | Li et al. | |
| 2019/0231778 A1 | 8/2019 | Habib | |
| 2019/0255050 A1 | 8/2019 | Habib | |
| 2020/0197397 A1 | 6/2020 | Arkin et al. | |
| 2022/0211706 A1 | 7/2022 | Habib | |
| 2022/0218682 A1 | 7/2022 | Habib | |

FOREIGN PATENT DOCUMENTS

| | | | | |
|---|---|---|---|---|
| AU | 2020100093 A4 | 2/2020 | | |
| CN | 101669941 | 11/2012 | | |
| CN | 102389424 B | 11/2013 | | |
| EP | 3528798 A1 | 8/2019 | | |
| WO | WO-2001/027268 A2 | 4/2001 | | |
| WO | WO 2007/138613 A2 | 12/2007 | | |
| WO | WO 2011/014872 A2 | 2/2011 | | |
| WO | WO 2013/152313 A1 | 10/2013 | | |
| WO | WO 2015/009879 A1 | 1/2015 | | |
| WO | WO-2015028614 A1 * | 3/2015 | ........... | C12N 5/0613 |

(Continued)

OTHER PUBLICATIONS

Liu et al (Molecular Cancer Therapetuics, 2011, vol. 10, pp. 518-530) (Year: 2011).*
Hofer et al (Clinical Cancer Research, 2016, vol. 22, pp. 5130-5140). (Year: 2016).*
Anonymous (2015) "AstraZeneca presents positive new data on anifrolumab in lupus at American College of Rheumatology Annual Scientific Meeting," Nov. 10, 2015, pp. 1-6, XP93128273.
Borden Ernest C. (2019) "Interferons [alpha] and [beta] in cancer: therapeutic opportunities from new insights," *Nature Reviews Drug Discovery* 18(3): 219-234.

(Continued)

*Primary Examiner* — Karen A. Canella
(74) *Attorney, Agent, or Firm* — Ballard Spahr LLP

(57) ABSTRACT

Provided herein are methods and pharmaceutical compositions for treating cancer, in a patient in need thereof, said method comprising administering to said patient an effective amount of an EGFR inhibitor and a TNF inhibitor.

15 Claims, 26 Drawing Sheets

Specification includes a Sequence Listing.

(56) References Cited

FOREIGN PATENT DOCUMENTS

| WO | WO 2016/191471 | A1 | 12/2016 |
| WO | WO-2017/037579 | A1 | 3/2017 |
| WO | WO 2017/106189 | | 6/2017 |
| WO | WO-2018/075823 | A1 | 4/2018 |
| WO | WO-2018/183762 | A1 | 10/2018 |
| WO | WO 2020/227676 | A1 | 11/2020 |

OTHER PUBLICATIONS

Carbone Maria et al. (2018) "Topical Plant Polyphenols Prevent Type I Interferon Signaling in the Skin and Suppress Contact Hypersensitivity," *International Journal of Molecular Sciences* 19(9): 2652.

Garrido-Laguna I. et al. (2013) "A phase I/II study of decitabine in combination with panitumumab in patients with wild-type (wt)KRASmetastatic colorectal cancer," *Investigational New Drugs* 31(5): 1257-1264.

Green Colin et al. (2007) "Combination of the vascular disrupting agent DMXAA (AS1404) with cetuximab produces synergistic antitumor activity in lung cancer xenografts," *Cancer Research*: 1-3, XP93127442.

Jae Hong No et al. (2013) "Targeting Nrf2 Signaling to Combat Chemoresistance," *Journal of Cancer Prevention* 19(2): 111-117.

Julie Bauman et al. (2011) "A phase I study of 5-azacytidine and erlotinib in advanced solid tumor malignancies," *Cancer Chemotherapy and Pharmacology* 69(2): 547-554.

Lee Ho-June et al. (2014) "Drug Resistance via Feedback Activation of Stat3 in Oncogene-Addicted Cancer Cells," *Cancer Cell* 26(2): 207-221.

Lukghele Sabelo et al. (2019) "Type I interferon signaling, regulation and gene simulation in chronic virus infection," *Seminars in Immunology* 43, XP085918268.

Nie Peipei et al. (2015) "Synergistic Induction of Erlotinib-Mediated Apoptosis by Resveratrol in Human Non-Small-Cell Lung Cancer Cells by Down-Regulating Survivin and Up-Regulating PUMA," *Cellular Physiology and Biochemistry* 35(6): 2255-2271.

Park Ji Soo et al. (2019) "A phase Ib study of the combination of afatinib and ruxolitinib in EGFR mutant NSCLC with progression on EGFR-TKIs," *Lung Cancer* 134: 46-51.

Satoshi Okazaki et al. (2017) "Predictive value of TLR7 polymorphism for cetuximab-based chemotherapy in patients with metastatic colorectal cancer," *International Journal of Cancer* 141(6): 1222-1230.

Yamadori et al. (2012) "Molecular mechanisms for the regulation of Nrf2-mediated cell proliferation in non-small-cell lung cancers," *Oncogene* 31(45): 4768-4777.

Zhang et al. (2009) "EGFR-Nrf2 pathway plays a role in cancer cell's chemoresistance," *Bioscience Hypothesis* 2(4): 261-263.

Zhu Yuanyuan et al. (2019) "STING: a master regulator in the cancer-immunity cycle," *Molecular Cancer* 18(1): 1476-1598.

Gadji, M., et al., (2009) EGF receptor inhibitors in the treatment of glioblastoma multiform: old clinical allies and newly emerging therapeutic concepts. *European Journal of Pharmacology*, 625(1-3), 23-30.

Grossman SA, et al., (2011) NABTT CNS Consortium. Immunosuppression in patients with high-grade gliomas treated with radiation and temozolomide. *Clin Cancer Res. Aug* 15;17(16):5473-80.

Hoque, M., et al., (2018). Changes in cell morphology guide identification of tubulin as the off-target for protein kinase inhibitors. Pharmacological research, 134, 166-178.

Kim, H. D., et al., (2008). Epidermal growth factor-induced enhancement of glioblastoma cell migration in 3D arises from an intrinsic increase in speed but an extrinsic matrix- and proteolysis-dependent increase in persistence. Molecular biology of the cell, 19(10), 4249-4259.

Nehoff H, et al., (2015) A combination of tyrosine kinase inhibitors, crizotinib and dasatinib for the treatment of glioblastoma multiforme. Oncotarget. 6(35):37948-64.

Acquaviva, et al. (2011) "Chronic activation of wild-type epidermal growth factor receptor and loss of Cdkn2a cause mouse glioblastoma formation" Cancer Res 71: 7198-7206.

Aggarwal, et al. (2013) "Curcumin: an orally bioavailable blocker of TNF and other pro-inflammatory biomarkers" British Journal of Pharmacology 169(8): 1672-1692.

Ahmad, et al. (2016) "Nrf2-driven TERT regulates pentose phosphate pathway in glioblastoma" Cell Death Dis 7: e2213.

Akbay,et al. (2013) "Activation of the PD-1 pathway contributes to immune escape in EGFR-driven lung tumors" Cancer Discov 3: 1355-1363.

Akbay, E. A. & Kim, J. (2018) "Autochthonous murine models for the study of smoker and never-smoker associated lung cancers" Transl Lung Cancer Res 7: 464-486.

Akhavan, et al. (2013) "De-repression of PDGFRbeta transcription promotes acquired resistance to EGFR tyrosine kinase inhibitors in glioblastoma patients" Cancer Discov 3: 534-547.

Alcazar, et al. "Augmented HR Repair Mediates Acquired Temozolomide Resistance in Glioblastoma," *Mol Cancer Res*, 23, 928-940.

Almeida, et al. (2009) Paradoxical effect of isoniazid on the activity of rifampin-pyrazinamide combination in a mouse model of tuberculosis, Antimicrob Agents Chemother 53, 4178-4184.

Altieri, et al. (2015) Glioma Surgery: Technological Advances to Achieve a Maximal Safe Resection, Surg Technol Int 27, 297-302.

An, et al. (2018) "Epidermal growth factor receptor and EGFRvIII in glioblastoma: signaling pathways and targeted therapies" Oncogene 37: 1561-1575.

Armento, et al. (2017) Molecular Mechanisms of Glioma Cell Motility, In Glioblastoma (De Vleeschouwer, S., Ed.), Brisbane (AU).

Au, et al. (1995) "Identification of a member of the interferon regulatory factor family that binds to the interferon-stimulated response element and activates expression of interferon-induced genes" Proc Natl Acad Sci U S A 92: 11657-11661.

Augustin, et al. (2013) "Quantitative Chemical Proteomics Profiling Differentiates Erlotinib from Gefitinib in EGFR Wild-Type Non-Small Cell Lung Carcinoma Cell Lines;" Mol Cancer Ther; 12(4).

Ausubel, F. M. (1987) Current protocols in molecular biology, Published by Greene Pub. Associates and Wiley-Interscience : J. Wiley, New York.

Awad, et al. (2014) "Targeting MET for Glioma Therapy" *Neurosurgical Focus*, 37, E10zhu.

Bachoo, et al. (2002) Epidermal growth factor receptor and Ink4a/Arf: convergent mechanisms governing terminal differentiation and transformation along the neural stem cell to astrocyte axis, Cancer Cell 1, 269-277.

Bae, et al. (2013) Sestrins activate Nrf2 by promoting p62-dependent autophagic degradation of Keap1 and prevent oxidative liver damage, Cell Metab 17, 73-84.

Bai, et al. (2016) "Emerging role of NRF2 in chemoresistance by regulating drug-metabolizing enzymes and efflux transporters" Drug Metab Rev 48: 541-567.

Bald, et al. (2014) "Immune cell-poor melanomas benefit from PD-1 blockade after targeted type I IFN activation" Cancer Discov 4: 674-687.

Balkwill, et al. (2009), "Tumour Necrosis Factor and Cancer," *Nat. Rev. Cancer* 9, 361-371.

Balkwill, et al. (2006) "TNF-alpha in Promotion and Progression of Cancer," *Cancer Metastasis Reviews* 25, 409-416.

Banks (2015) "Peptides and the blood-brain barrier" *Peptides* 72: 16-19.

Bansal, et al. (2012) The transcription factor Wilms tumor 1 confers resistance in myeloid leukemia cells against the proapoptotic therapeutic agent TRAIL (tumor necrosis factor alpha-related apoptosis-inducing ligand) by regulating the antiapoptotic protein Bcl-XL, J Biol Chem 287, 32875-32880.

Bansal, A., and Simon, M. C. (2018) Glutathione metabolism in cancer progression and treatment resistance, J Cell Biol 217, 2291-2298.

(56) References Cited

OTHER PUBLICATIONS

Bardella, et al. (2012) Cells lacking the fumarase tumor suppressor are protected from apoptosis through a hypoxia-inducible factor-independent, AMPK-dependent mechanism, Mol Cell Biol 32, 3081-3094.

Barkovich, et al. (2012) "Kinetics of Inhibitor Cycling Underlie Therapeutic Disparities Between EGFR-Driven Lung and Brain Cancers," Cancer Discov, 2, 450-457.

Barnes (1998) "Anti-inflammatory Actions of Glucocortiods: Molecular Mechanisms" Clinical Science 94: pp. 557-572.

Barnett, et al., "Anti-inflammatory Effects of mi-21 in the Macrophage Response to Peritonitis," J Leukoc Biol, 99, 361-371.

Bartel, (2009) "MicroRNAs: Target Recognition and Regulatory Functions," Cell, 136, 215-233.

Batra, et al. (1995) Epidermal growth factor ligand-independent, unregulated, cell-transforming potential of a naturally occurring human mutant EGFRvIII gene, Cell Growth Differ 6, 1251-1259.

Belda-Iniesta, et al. (2006) "Long Term Responses with Cetuximab Therapy in Glioblastoma Multiforme" Cancer Biol. & Ther; 5:8 pp. 912-914.

Ben-Neriah, et al. "Inflammation Meets Cancer, with NF-kappaB as the Matchmaker," Nat. Immunol, 12, 715-723.

Best, S. A., and Sutherland, K. D. (2018) "Keaping" a lid on lung cancer: the Keap1-Nrf2 pathway, Cell Cycle 17, 1696-1707.

Bhatt, et al. (2014) Pharmacokinetics of rifampin and isoniazid in tuberculosis-HIV-coinfected patients receiving nevirapine- or efavirenz-based antiretroviral treatment, Antimicrob Agents Chemother 58, 3182-3190.

Biernat, et al. (2004) Predominant expression of mutant EGFR (EGFRvIII) is rare in primary glioblastomas, Brain pathology 14, 131-136.

Birnbaum, et al. (2003) Chromosome arm 8p and cancer: a fragile hypothesis, The lancet oncology 4, 639-642.

Bivona, et al. "FAS and NF-kappaB Signaling Modulate Dependence of Lung Cancers on Mutant EGFR" Nature, 471, 523-526.

Blakely, et al. (2015) "NF-kappaB-activating complex engaged in response to EGFR oncogene inhibition drives tumor cell survival and residual disease in lung cancer," Cell Rep 11, 98-110.

Brenner, et al. Regulation of Tumour Necrosis Factor Signaling: Live or Let Die, Nat Rev Immunol, 15, 362-374.

Bronger, et al. (2005) ABCC drug efflux pumps and organic anion uptake transporters in human gliomas and the blood-tumor barrier, Cancer Res 65, 11419-11428.

Brown, et al. (2008) Phase I/II trial of erlotinib and temozolomide with radiation therapy in the treatment of newly diagnosed glioblastoma multiforme: North Central Cancer Treatment Group Study N0177, J Clin Oncol 26, 5603-5609.

Bryan, et al. (2013) The Nrf2 cell defence pathway: Keap1-dependent and -independent mechanisms of regulation, Biochem Pharmacol 85, 705-717.

Budhwani, et al. Plasticity of Type I Interferon-Mediated Responses in Cancer Therapy: From Anti-tumor Immunity to Resistance. Front Oncol 8, 322, doi:10.3389/fonc.2018.00322 (2018).

Burger, et al. (2001) "Small Cell Architecture—a Histological Equivalent of EGFR Amplification in Glioblastoma Multiforme" J. Neuropathol Exp Neurol, 60, 1099-1104.

Camp, et al. (2012) Wilms tumor gene on X chromosome (WTX) inhibits degradation of NRF2 protein through competitive binding to KEAP1 protein, J Biol Chem 287, 6539-6550.

Cancer Network (2015) "FDA grants Osimertinib accelerated approval for T790M-positive NSCLC" http://www.cancernetwork.com/view/fda-grants-osimertinib-accelerated -approval-t790m-positive-nsclc.

Carlson, et al. (2011) Establishment, maintenance and in vitro and in vivo applications of primary human glioblastoma multiforme (GBM) xenograft models for translational biology studies and drug discovery, Curr Protoc Pharmacol Chapter 14, Unit 14 16.

Chakraborty, et al. (2013) Cytoplasmic TRADD Confers a Worse Prognosis in Glioblastoma, Neoplasia 15, 888-897.

Chakraborty, S. et al. Constitutive and ligand-induced EGFR signalling triggers distinct and mutually exclusive downstream signalling networks. Nat Commun 5, 5811, doi:10.1038/ncomms6811 (2014).

Chandarlapaty, S. et al. AKT inhibition relieves feedback suppression of receptor tyrosine kinase expression and activity. Cancer Cell 19, 58-71, doi:10.1016/j.ccr.2010.10.031 (2011).

Chang, et al. (2007) Integration of somatic deletion analysis of prostate cancers and germline linkage analysis of prostate cancer families reveals two small consensus regions for prostate cancer genes at 8p, Cancer Res 67, 4098-4103.

Chatterjee, A., and Gupta, S. (2018) The multifaceted role of glutathione S-transferases in cancer, Cancer Lett 433, 33-42.

Chaudiere, et al. (1984) Mechanism of selenium-glutathione peroxidase and its inhibition by mercaptocarboxylic acids and other mercaptans, J Biol Chem 259, 1043-1050.

Chen, et al. (2009) Direct interaction between Nrf2 and p21(Cip1/WAF1) upregulates the Nrf2-mediated antioxidant response, Mol Cell 34, 663-673.

Chen, H. H., and Kuo, M. T. (2010) Role of glutathione in the regulation of Cisplatin resistance in cancer chemotherapy, Met Based Drugs 2010.

Chen, et al. (2013) Isoniazid suppresses antioxidant response element activities and impairs adipogenesis in mouse and human preadipocytes, Toxicology and applied pharmacology 273, 435-441.

Chen, et al. (2015) Erastin sensitizes glioblastoma cells to temozolomide by restraining xCT and cystathionine-gamma-lyase function, Oncology reports 33, 1465-1474.

Chen, et al. (2016) Mammalian drug efflux transporters of the ATP binding cassette (ABC) family in multidrug resistance: A review of the past decade, Cancer Lett 370, 153-164.

Chen, et al. (2011) "Elevated BCRP/ABCG2 Expression Confers Acquired Resistance to Gefitinib in Wold-Type EGFR-Expressing Cells" PLoS One, 6(6) 21428.

Cheon, H. et al. IFNbeta-dependent increases in STAT1, STAT2, and IRF9 mediate resistance to viruses and DNA damage. EMBO J 32, 2751-2763, doi:10.1038/emboj.2013.203 (2013).

Chong, C. R. & Janne, P. A. The quest to overcome resistance to EGFR-targeted therapies in cancer. Nature medicine 19, 1389-1400, doi:10.1038/nm.3388 (2013).

Chow, et al. RIG-I and Other RNA Sensors in Antiviral Immunity. Annu Rev Immunol 36, 667-694, doi:10.1146/annurev-immunol-042617-053309 (2018).

Chung, et al. (2005) Inhibition of cystine uptake disrupts the growth of primary brain tumors, J Neurosci 25, 7101-7110.

Chung, W. J., and Sontheimer, H. (2009) Sulfasalazine inhibits the growth of primary brain tumors independent of nuclear factor-kappaB, J Neurochem 110, 182-193.

Ciardiello, et al EGFR Antagonists in Cancer Treatment, N. Engl. J. Med. 358, 1160-1174.

Coll, et al. (2007) Hob3p, the fission yeast ortholog of human BIN3, localizes Cdc42p to the division site and regulates cytokinesis, EMBO J 26, 1865-1877.

Cong, et al. (2013) ERK and PI3K signaling cascades induce Nrf2 activation and regulate cell viability partly through Nrf2 in human glioblastoma cells, Oncology reports 30, 715-722.

Corcoran, R. B. et al. EGFR-mediated re-activation of MAPK signaling contributes to insensitivity of BRAF mutant colorectal cancers to RAF inhibition with vemurafenib. Cancer Discov 2, 227-235, doi:10.1158/2159-8290.CD-11-0341 (2012).

Cui et al. Low BIN3 Expression is an Independent Predictor of Unfavorable Survival in Patients With Primary Colorectal Cancer, Technol Cancer Res Treat. Dec. 26, 2017, vol. 16, No. 6, pp. 1244-1251.

Cui, et al. (2018) Modulating ROS to overcome multidrug resistance in cancer, Drug Resist Updat 41, 1-25.

Das, et al. (2014) Engulfment of Apoptotic Cells by Macrophages: a role of micro-RNA-21 in the Resolution of Wound Inflammation, j. Immunol, 192, 1120-1129.

Davis (2000) "Signal Transduction by JNK Group of MAP Kinases" Cell, 103, 239-252.

De Kreuk, B. J., and Hordijk, P. L. (2012) Control of Rho GTPase function by BAR-domains, Small GTPases 3, 45-52.

(56) References Cited

OTHER PUBLICATIONS

Deng, et al. (2003) "Thalidomide Inhibits Tumor Necrosis Factor-Alpha Production and Antigen Prosentation by Langerhans Cells," *The Journal of Investigative Dermatology*, 121, 1050-1065.

De la Iglesia, et al. (2008)"Identification of a PTEN-Regulated STAT3 Brain Tumor Suppressor Pathway," *Genes Dev*, 22, 449-462.

Dhruv, et al. (2013) Reciprocal activation of transcription factors underlies the dichotomy between proliferation and invasion of glioma cells, PLoS One 8, e72134.

Di Fiore, et al. (1987) Overexpression of the human EGF receptor confers an EGF-dependent transformed phenotype to NIH 3T3 cells, Cell 51, 1063-1070.

Dickinson, et al. (1992) Bioavailability of rifampin in experimental murine tuberculosis, Antimicrob Agents Chemother 36, 2066-2067.

Ding, et al. (2018) A Novel Signaling Complex between TROY and EGFR Mediates Glioblastoma Cell Invasion, Mol Cancer Res 16, 322-332.

Dinkova-Kostova, et al. (2002) Direct evidence that sulfhydryl groups of Keap1 are the sensors regulating induction of phase 2 enzymes that protect against carcinogens and oxidants, Proc Natl Acad Sci U S A 99, 11908-11913.

Dinkova-Kostova, A. T., and Talalay, P. (2010) NAD(P)H:quinone acceptor oxidoreductase 1 (NQO1), a multifunctional antioxidant enzyme and exceptionally versatile cytoprotector, Arch Biochem Biophys 501, 116-123.

Duarte, C. W. et al. Expression signature of IFN/STAT1 signaling genes predicts poor survival outcome in glioblastoma multiforme in a subtype-specific manner. PLoS One 7, e29653, doi:10.1371/journal. pone.0029653 (2012).

Duncan, J. S. et al. Dynamic reprogramming of the kinome in response to targeted MEK inhibition in triple-negative breast cancer. Cell 149, 307-321, doi:10.1016/j.cell.2012.02.053 (2012).

Dunn, G. P. et al. A critical function for type I interferons in cancer immunoediting. Nat Immunol 6, 722-729, doi:10.1038/ni1213 (2005).

Dutu, T. et al. Differential expression of biomarkers in lung adenocarcinoma: a comparative study between smokers and never-smokers. Ann Oncol 16, 1906-1914, doi:10.1093/annonc/mdi408 (2005).

Ebelt, et al. (2017) "A c-Jun-N-terminal Kinase Inhibitor, JNK-IN-8, Sensitttizer Triple Negative Breast Cancer Cells to Lapatinib;" Oncotarget, Vo. 8: 62, pp. 104894-104912.

Ekstrand, et al. (1991) Genes for epidermal growth factor receptor, transforming growth factor alpha, and epidermal growth factor and their expression in human gliomas in vivo, *Cancer Res 51*, 2164-2172.

Endres, N. F. et al. (2013) Conformational coupling across the plasma membrane in activation of the EGF receptor. *Cell* 152, 543-556.

Engelman, J. A. et al. MET amplification leads to gefitinib resistance in lung cancer by activating ERBB3 signaling. *Science* 316, 1039-1043, doi:1141478 [pii] 10.1126/science.1141478 (2007).

Estrada-Bernal, et al. (2011) The role of sphingosine kinase-1 in EGFRvIII-regulated growth and survival of glioblastoma cells, J Neurooncol 102, 353-366.

Fallahi-Sichani, M. et al. Systematic analysis of BRAF(V600E) melanomas reveals a role for JNK/c-Jun pathway in adaptive resistance to drug-induced apoptosis. Mol Syst Biol 11, 797, doi:10. 15252/msb.20145877 (2015).

Fan, et al. (2003) Combinatorial efficacy achieved through two-point blockade within a signaling pathway—a chemical genetic approach, Cancer Res 63, 8930-8938.

Fan, et al. (2006) A dual PI3 kinase/mTOR inhibitor reveals emergent efficacy in glioma, Cancer Cell 9, 341-349.

Fan, et al. (2011) "MET-independent Lung Cancer Cells Evading EGFR Kinase Inhibitors are Therapeutically Susceptible to BH3 Mimetic Agents," *Cancer Res.* 71, 4494-4505.

Fan, et al. (2013) EGFR Phosphorylates Tumor-Derived EGFRvIII Driving STAT3/5 and Progression in Glioblastoma, Cancer Cell 24, 438-449.

Fan, Z., et al. (2017) Nrf2-Keap1 pathway promotes cell proliferation and diminishes ferroptosis, Oncogenesis 6, e371.

Faustman, (2010) "TNF Receptor 2 Pathway: Drug Target for Autoimmune Diseases," *Nat Rev Drug Discov*, 9, 482-493.

Fitzgerald, K. A. et al. IKKepsilon and TBK1 are essential components of the IRF3 signaling pathway. Nat Immunol 4, 491-496, doi:10.1038/ni921 [pii] (2003).

Fletcher, et al. (2016) ABC transporters as mediators of drug resistance and contributors to cancer cell biology, Drug Resist Updat 26, 1-9.

Fortin (2012) "The blood-brain barrier: its influence in the treatment of brain tumors metastases" *Current Cancer Drug Targets* 12: 247-259.

Fortin Ensign, et al. (2013) Implications of Rho GTPase Signaling in Glioma Cell Invasion and Tumor Progression, Front Oncol 3, 241.

Fourquet, et al. (2010) Activation of NRF2 by nitrosative agents and H2O2 involves KEAP1 disulfide formation, J Biol Chem 285, 8463-8471.

Frank, et al. (2006) Gene expression signature of primary imatinib-resistant chronic myeloid leukemia patients, Leukemia 20, 1400-1407.

Frederick, et al. (2000) Diversity and frequency of epidermal growth factor receptor mutations in human glioblastomas, Cancer Res 60, 1383-1387.

Fruh, M., and Pless, M. (2012) EGFR IHC score for selection of cetuximab treatment: Ready for clinical practice?, Transl Lung Cancer Res 1, 145-146.

Furie, R. et al. Anifrolumab, an Anti-Interferon-alpha Receptor Monoclonal Antibody, in Moderate-to-Severe Systemic Lupus Erythematosus. Arthritis Rheumatol 69, 376-386, doi:10.1002/art. 39962 (2017).

Furnari, et al. (2007) Malignant astrocytic glioma: genetics, biology, and paths to treatment, Genes Dev 21, 2683-2710.

Furnari, et al. (2015) "Heterogeneity of Epidermal Growth Factor Receptor Signalling Networks in Glioblastoma," *Nat Rev Cancer*, 15, 302-310.

Gadea, G., and Blangy, A. (2014) Dock-family exchange factors in cell migration and disease, Eur J Cell Biol 93, 466-477.

Gadgeel, et al. (2009) "Retracted: Genistein enhances the effect of epidermal growth factor receptor tyrosine kinase inhibitors and inhibits nuclear factor kappa B in nonsmall cell lung cancer cell lines" Cancer 115(10): 2165-2176.

Gainor, J. F. et al. EGFR Mutations and ALK Rearrangements Are Associated with Low Response Rates to PD-1 Pathway Blockade in Non-Small Cell Lung Cancer: A Retrospective Analysis. Clin Cancer Res 22, 4585-4593, doi:10.1158/1078-0432.CCR-15-3101 (2016).

Galan-Cobo, et al. (2019) LKB1 and KEAP1/NRF2 Pathways Cooperatively Promote Metabolic Reprogramming with Enhanced Glutamine Dependence in KRAS-Mutant Lung Adenocarcinoma, Cancer Res 79, 3251-3267.

Gao, et al. (2005) Proliferation and invasion: plasticity in tumor cells, Proc Natl Acad Sci U S A 102, 10528-10533.

Giese, et al. (1996) Dichotomy of astrocytoma migration and proliferation, Int J Cancer 67, 275-282.

Gong, K. et al. TNF-driven adaptive response mediates resistance to EGFR inhibition in lung cancer. J Clin Invest 128, 2500-2518, doi:10.1172/JCI96148 (2018).

Gonzalez-Juarrero, et al. (2012) Mouse model for efficacy testing of antituberculosis agents via intrapulmonary delivery, Antimicrob Agents Chemother 56, 3957-3959.

Gorrini, et al. (2013) BRCA1 interacts with Nrf2 to regulate antioxidant signaling and cell survival, J Exp Med 210, 1529-1544.

Greenall, et al. (2015) "EGFvIII-Mediated Transactivation of Receptor Tyrosine Kinases in Glioma: Mechanism and Therapeutic Implications," *Oncogene*, 34, 5277-5287.

Greulich, et al. (2005) "Oncogenic Transformation by Inhibitor-Sensitive and—resistant EGFR Mutants." *PLos Med*, 2, e313.

Gross, et al. (2007) "Inhibition of Jun NH2-Terminal Kinases Suppresses the Growth of Experimental Head and Neck Squamous Cell Carcinoma" *Clin Cancer Res* 13, 5910-5917.

(56)         References Cited

OTHER PUBLICATIONS

Groves, et al. (2007) "A North American Brain Tumor Consortium (NABTC 99-04) Phase II Trial of Temozolomide Plus Thalidomide for Recurrent Glioblastoma Multiforme," *J. Neurooncol*, 81, 271-277.

Gu, et al. (2011) Determination of sulphasalazine and its main metabolite sulphapyridine and 5-aminosalicylic acid in human plasma by liquid chromatography/tandem mass spectrometry and its application to a pharmacokinetic study, Journal of chromatography. B, Analytical technologies in the biomedical and life sciences 879, 449-456.

Gullick, (1991) "Prevalence of Aberrant Expression of the Epidermal Growth Factor Receptor in Human Cancers," *Br Med Bull*, 47, 87-98.

Guo, et al. "Signaling Networks Assembled by Oncogenic EGFR and c-Met" *Proc Natl Acad Sci U*, 105, 692-697.

Guo, et al. (2009) EGFR signaling through an Akt-SREBP-1-dependent, rapamycin-resistant pathway sensitizes glioblastomas to antilipogenic therapy, Sci Signal 2, ra82.

Guo, G. et al. Ligand-Independent EGFR Signaling. Cancer Res 75, 3436-3441, doi:10.1158/0008-5472.CAN-15-0989 (2015).

Guo, G. et al. A TNF-JNK-Axl-ERK signaling axis mediates primary resistance to EGFR inhibition in glioblastoma. Nat Neurosci 20, 1074-1084, doi:10.1038/nn.4584 (2017).

Guo, et al. (2019) Efficacy of EGFR plus TNF inhibition in a preclinical model of temozolomide-resistant glioblastoma, Neuro Oncol. Jul. 31, 2019. pii: noz127. doi: 10.1093/neuonc/noz127. [Epub ahead of print].

Gupta, et al. (2016) Delineation of MGMT Hypermethylation as a Biomarker for Veliparib-Mediated Temozolomide-Sensitizing Therapy of Glioblastoma, Journal of the National Cancer Institute 108.

Habermann, B. (2004) The BAR-domain family of proteins: a case of bending and binding?, EMBO reports 5, 250-255.

Habib, et al. (2001) The Epidermal Growth Factor Receptor Engages Receptor Interacting Protein and Nuclear Factor-Kappa B (NF-Kappa B)-Inducing Kinase to Activate NF-kappa B, Identification of Novel Receptor-Tyrosine Kinase Signalosome, *J. Biol Chem*, 276,8865-8874.

Hall, et al. (2014) Inhibition of glutathione peroxidase mediates the collateral sensitivity of multidrug-resistant cells to tiopronin, J Biol Chem 289, 21473-21489.

Hammond, et al. (2010) American society of clinical oncology/college of american pathologists guideline recommendations for immunohistochemical testing of estrogen and progesterone receptors in breast cancer, J Oncol Pract 6, 195-197.

Hast, et al. (2013) Proteomic analysis of ubiquitin ligase KEAP1 reveals associated proteins that inhibit NRF2 ubiquitination, Cancer Res 73, 2199-2210.

Hatanpaa, et aBlakelyl. (2010) Epidermal growth factor receptor (EGFR) in glioma: Signal transduction, neuropathology, imaging and radioresistance Neoplasia 12, 675-684.

Hatzikirou, et al. (2012) 'Go or grow': the key to the emergence of invasion in tumour progression?, Math Med Biol 29, 49-65.

Hayes, J. D., and McMahon, M. (2009) NRF2 and KEAP1 mutations: permanent activation of an adaptive response in cancer, Trends in biochemical sciences 34, 176-188.

Hedditch, et al. (2014) ABCA transporter gene expression and poor outcome in epithelial ovarian cancer, Journal of the National Cancer Institute 106.

Hegi, et al. (2005) MGMT gene silencing and benefit from temozolomide in glioblastoma, N Engl J Med 352, 997-1003.

Higuchi, (1994) "TNF Induces Internalization of the p60 Receptor and Shedding of the p80 Receptor," *J. Immunol*, 152, 3550-3558.

Hirsch, et al. "Epidermal Growth Factor Receptor in Non-Small-Cell Lung Carcinomas: Correlation Between Gene Copy No. and Protein Expression and Impact on Prognosis," *J. Clin Onc.*, 21, 3798-3807.

Holland, et al. (1998) "A Constitutively Active Epidermal Growth Factor Receptor Cooperates with Disruption of G1 Cell-Cycle Arrest Pathways to Induce Glioma-like Lesions in Mice," *Genes Dev*, 12, 3675-3685.

Hsieh, et al. "Co-Expression of Epidermal Growth Factor Receptor and Transforming Growth Factor-Alpha is Independent of ras Mutations in mng Adenocarcinoma", *Lung Cancer*, 29, 151-157.

Hirst, et al. (2013) Systematic review and meta-analysis of temozolomide in animal models of glioma: was clinical efficacy predicted?, Br J Cancer 108, 64-71.

Honda, K. & Taniguchi, T. IRFs: master regulators of signalling by Toll-like receptors and cytosolic pattern-recognition receptors. Nat Rev Immunol 6, 644-658, doi:nri1900 [pii] 10.1038/nri1900 (2006).

Horing, et al. (2012) The "go or grow" potential of gliomas is linked to the neuropeptide processing enzyme carboxypeptidase E and mediated by metabolic stress, *Acta neuropathologica 124*, 83-87.

Holzberg et al. (2003) "Disruption of the c-JUN-JNK complex by a cell-permeable peptide containing the c-JUN delta domain induces apoptosis and affects a distinct set of interleukin-1-induced inflammatory genes" *Journal of Biological Chemistry* 278: 40213-40223.

Hsieh, et al. Co-expression of epidermal growth factor receptor and transforming growth factor-alpha is independent of ras mutations in lung adenocarcinoma. *Lung cancer* 29, 151-157 (2000).

Huang, et al. (2007) "Quantitative Analysis of EGFRvIII Cellular Signaling Networks Reveals a Combinatorial Therapeutic Stragegy for Gioblastoma," *Proc Natl Acad Sci USA*, 104, 12867-12872.

Huang, et al. (2009) Oncogenic EGFR signaling networks in glioma, *Sci Signal* 2, re6.

Hundsberger, et al. (2017) Angiogenesis inhibitors in tackling recurrent glioblastoma, *Expert Rev Anticancer Ther 17*, 507-515.

Huo, et al. (2016) Erastin Disrupts Mitochondrial Permeability Transition Pore (mPTP) and Induces Apoptotic Death of Colorectal Cancer Cells, *PLoS One 11*, e0154605.

Hutchinson, et al. (2015) Epidermal growth factor receptor immunohistochemistry: new opportunities in metastatic colorectal cancer, *J Transl Med 13*, 217.

Ichimura, et al. (2013) Phosphorylation of p62 activates the Keap1-Nrf2 pathway during selective autophagy, *Mol Cell 51*, 618-631.

Im et al., Immune-Modulation by Epidermal Growth Factor Receptor Inhibitors: Implication on Anti-Tumor Immunity in Lung Cancer. PLOS One. Jul. 28, 2016, vol. 11, No. 7, pp. 1-20.

Inda, et al. (2010) Tumor heterogeneity is an active process maintained by a mutant EGFR-induced cytokine circuit in glioblastoma, Genes Dev 24, 1731-1745.

Ivashkiv, L. B. & Donlin, L. T. Regulation of type I interferon responses. Nat Rev Immunol 14, 36-49, doi:10.1038/nri3581 (2014).

Jackson, et al. (2019) Mechanisms of immunotherapy resistance: lessons from glioblastoma, Nat Immunol 20, 1100-1109.

Jahani-Asl, et al. (2016) "Control of Glioblastoma Tumorigenesis by Feed-Forward Cytokine Signaling," *Nat. Neurosci*, 19, 798-806.

Jahangiri, et al. (2017) Cross-activating c-Met/beta1 integrin complex drives metastasis and invasive resistance in cancer, Proc Natl Acad Sci U S A 114, E8685-E8694.

Jaramillo, M. C., and Zhang, D. D. (2013) The emerging role of the Nrf2-Keap1 signaling pathway in cancer, Genes Dev 27, 2179-2191.

Jen-Yi, et al. (2011) "Curcumin Induces EGFR Degradation in Lung Adenocarcinoma and Modulates p38 Activation in Intestine: The Versatile Adjuvant for Gefitinib Therapy" PLoS One 6(8): e23756.

Jeong, et al. (2017) Role of KEAP1/NRF2 and TP53 Mutations in Lung Squamous Cell Carcinoma Development and Radiation Resistance, Cancer Discov 7, 86-101.

Ji, et al. (2018) xCT (SLC7A11)-mediated metabolic reprogramming promotes non-small cell lung cancer progression, Oncogene 37, 5007-5019.

Jia, et al. (2012) Inhibition of glutathione synthesis reverses Kruppel-like factor 4-mediated cisplatin resistance, Cancer Chemother Pharmacol 69, 377-385.

Jia, et al. (2015) Micheliolide overcomes KLF4-mediated cisplatin resistance in breast cancer cells by downregulating glutathione, Onco Targets Ther 8, 2319-2327.

Jiang, et al. (2014) PKM2 phosphorylates MLC2 and regulates cytokinesis of tumour cells, Nat Commun 5, 5566.

(56) References Cited

OTHER PUBLICATIONS

Johannessen, T. A., and Bjerkvig, R. (2019) A new chance for EGFR inhibition in glioblastoma?, Neuro Oncol. 21(12): 1487-1488.

Johnson, et al. (2001) "Relationships Between Drub Activity in NCI Preclinical in Vitro and In Vivo Modesl and Early Clinical Trials," British J. of Cancer, 84(10: 1424-1431.

Ju-Hwa, et al. (2013) "SP600125 overcomes antimitotic drug-resistance in cancer cells by increasing apoptosis with independence of P-gp inhibition," European Journal of Pharmacology, 732: 141-147.

Kanamori, et al. (2015) Activation of the NRF2 pathway and its impact on the prognosis of anaplastic glioma patients, Neuro Oncol 17, 555-565.

Kansanen, et al. (2013) The Keap1-Nrf2 pathway: Mechanisms of activation and dysregulation in cancer, Redox Biol 1, 45-49.

Karapetian, et al. (2005) Nuclear oncoprotein prothymosin alpha is a partner of Keap1: implications for expression of oxidative stress-protecting genes, Mol Cell Biol 25, 1089-1099.

Karpel-Massler, et al. (2009) Therapeutic inhibition of the epidermal growth factor receptor in high-grade gliomas: where do we stand?, Mol Cancer Res 7, 1000-. 1012.

Kathagen-Buhmann, et al. (2016) Glycolysis and the pentose phosphate pathway are differentially associated with the dichotomous regulation of glioblastoma cell migration versus proliferation, Neuro Oncol 18, 1219-1229.

Kiefer, et al. "Inhibition of NF-kappa B Activity by Thalidomide Through Suppression of IkappaB Kinase Activity," *J Biol Chem*, 276, 22382-22387.

Kerins, M. J., and Ooi, A. (2018) A catalogue of somatic NRF2 gain-of-function mutations in cancer, Sci Rep 8, 12846.

Khodarev, N. N. et al. Signal transducer and activator of transcription 1 regulates both cytotoxic and prosurvival functions in tumor cells. Cancer Res 67, 9214-9220, doi:10.1158/0008-5472.CAN-07-1019 (2007).

Khodarev, N. N. et al. STAT1 is overexpressed in tumors selected for radioresistance and confers protection from radiation in transduced sensitive cells. Proc Natl Acad Sci U S A 101, 1714-1719, doi:10.1073/pnas.0308102100 (2004).

Kim, et al. (2010) Oncogenic NRF2 mutations in squamous cell carcinomas of oesophagus and skin, The Journal of pathology 220, 446-451.

Kim, et al. (2014) "SP600125 Overcomes Antimitotic Drug-Resistance in Cancer Cells by Increasing Apoptosis with Independence of P-gp Inhibition" European Journal of Pharmacology; 723 pp. 141-147.

Kitajima, S. et al. Suppression of STING Associated with LKB1 Loss in KRAS-Driven Lung Cancer. Cancer Discov 9, 34-45, doi:10.1158/2159-8290.CD-18-0689 (2019).

Knobbe-Thomsen, et al. (2013) EGFR Phosphorylates Tumor-Derived EGFRvIII Driving STAT3/5 and Progression in Glioblastoma, *Cancer Cell 24*, 438-449.

Komatsu, et al. (2010) The selective autophagy substrate p62 activates the stress responsive transcription factor Nrf2 through inactivation of Keap1, *Nat Cell Biol 12*, 213-223.

Konstantinopoulos, et al. (2011) Keap1 mutations and Nrf2 pathway activation in epithelial ovarian cancer, *Cancer Res 71*, 5081-5089.

Krall, et al. (2017) KEAP1 loss modulates sensitivity to kinase targeted therapy in lung cancer, *Elife 6*.

Kruspig, B. et al. The ERBB network facilitates KRAS-driven lung tumorigenesis. *Sci Transl Med* 10, doi:10.1126/scitranslmed.aao2565 (2018).

Lampson (2011) "Monoclonal antibodies in neuro-oncology: Getting past the blood-brain barrier" *mAbs* 3: 153-160.

Lazzari, E. & Meroni, G. TRIM32 ubiquitin E3 ligase, one enzyme for several pathologies: From muscular dystrophy to tumours. *Int J Biochem Cell Biol* 79, 469-477, doi:10.1016/j.biocel.2016.07.023 (2016).

Le, et al. (2018) Landscape of EGFR-Dependent and- Independent Resistance Mechanisms to Osimertinib and Continuation Therapy Beyond Progression in EGFR-Mutant NSCLC, *Clin Cancer Res 24*, 6195-6203.

Lee, H. J. et al. Drug resistance via feedback activation of Stat3 in oncogene-addicted cancer cells. *Cancer Cell* 26, 207-221, doi:10.1016/j.ccr.2014.05.019 (2014).

Li, et al. (2011) KEAP1 gene mutations and NRF2 activation are common in pulmonary papillary adenocarcinoma, *J Hum Genet 56*, 230-234.

Li, et al. (2014) An EGFR wild type-EGFRvIII-HB-EGF feed-forward loop regulates the activation of EGFRvIII, *Oncogene 33*, 4253-4264.

Li, et al. (2016) beta-elemene sensitizes hepatocellular carcinoma cells to oxaliplatin by preventing oxaliplatin-induced degradation of copper transporter 1, *Sci Rep 6*, 21010.

Lim, et al. (2018) Current state of immunotherapy for glioblastoma, *Nat Rev Clin Oncol 15*, 422-442.

Lin (2015) "MicroRNA Biogenesis Pathways in Cancer," *Nat Rev Cancer*, 15, 321-333.

Liou, G. Y., and Storz, P. (2010) Reactive oxygen species in cancer, *Free Radic Res 44*, 479-496.

Liou, G. Y., and Storz, P. (2015) Detecting reactive oxygen species by immunohistochemistry, *Methods Mol Biol 1292*, 97-104.

Liu, et al. (2015) APR-246 potently inhibits tumour growth and overcomes chemoresistance in preclinical models of oesophageal adenocarcinoma, Gut 64, 1506-1516.

Liu, S. et al. Phosphorylation of innate immune adaptor proteins MAVS, STING, and TRIF induces IRF3 activation. Science 347, aaa2630, doi:10.1126/science.aaa2630 (2015).

Liu, Q. et al. EGFR-TKIs resistance via EGFR-independent signaling pathways. Mol Cancer 17, 53, doi:10.1186/s12943-018-0793-1 (2018).

Liu, Y. et al. Tumor-Repopulating Cells Induce PD-1 Expression in CD8(+) T Cells by Transferring Kynurenine and AhR Activation. Cancer Cell 33, 480-494 e487, doi:10.1016/j.ccell.2018.02.005 (2018).

Lopez-Bertoni, et al. (2016) Epigenetic modulation of a miR-296-5p:HMGA1 axis regulates Sox2 expression and glioblastoma stem cells, Oncogene 35, 4903-4913.

Lu, et al. (2005) "MicroRNA Expression Profiles Classify Human Cancers," *Nature*, 435, 834-838.

Lu, et al. (2009) Fyn and SRC are effectors of oncogenic epidermal growth factor receptor signaling in glioblastoma patients, *Cancer Res 69*, 6889-6898.

Lu, et al. (2017) NRF2 Induction Supporting Breast Cancer Cell Survival Is Enabled by Oxidative Stress-Induced DPP3-KEAP1 Interaction, *Cancer Res 77*, 2881-2892.

Lu, K. V., and Bergers, G. (2013) Mechanisms of evasive resistance to anti-VEGF therapy in glioblastoma, *CNS Oncol 2*, 49-65.

Luo, et al. (2009) Principles of cancer therapy: oncogene and non-oncogene addiction, *Cell 136*, 823-837.

Lynch, et al. (2004) Activating mutations in the epidermal growth factor receptor underlying responsiveness of non-small-cell lung cancer to gefitinib, *N Engl J Med 350*, 2129-2139.

Ma, et al. (2012) PALB2 interacts with KEAP1 to promote NRF2 nuclear accumulation and function, Mol Cell Biol 32, 1506-1517.

Ma, et al. (2019) TNFalpha inhibitor C87 sensitizes EGFRvIII transfected glioblastoma cells to gefitinib by a concurrent blockade of TNFalpha signaling, Cancer Biol Med 16, 606-617.

Mai, et al. (2017) Cytoplasmic p53 couples oncogene-driven glucose metabolism to apoptosis and is a therapeutic target in glioblastoma, Nature medicine 23, 1342--1351.

Majd, et al. (2019) The path forward for anti-programmed death-1 therapy in gliomas, Curr Opin Neurol.

Matsuda, et al. (2012) "Targeting JNK for therapeutic depletion of stem-like glioblastoma cells" *Sci Rep* 2: 516.

McDonald, et al. (2010) Ionizing radiation activates the Nrf2 antioxidant response, *Cancer Res 70*, 8886-8895.

McNeill, et al. (2015) Contemporary murine models in preclinical astrocytoma drug development, *Neuro Oncol 17*, 12-28.

Meissl, et al. The good and the bad faces of STAT1 in solid tumours. *Cytokine* 89, 12-20, doi:10.1016/j.cyto.2015.11.011 (2017).

(56) References Cited

OTHER PUBLICATIONS

Misek, et al. (2017) EGFR Signals through a DOCK180-MLK3 Axis to Drive Glioblastoma Cell Invasion, *Mol Cancer Res 15*, 1085-1095.

Mishima, et al. (1998) Heparin-binding epidermal growth factor-like growth factor stimulates mitogenic signaling and is highly expressed in human malignant gliomas, *Acta Neuropathol (Berl)* 96, 322-328.

Mohell, et al. (2015) APR-246 overcomes resistance to cisplatin and doxorubicin in ovarian cancer cells, Cell Death Dis 6, e1794.

Moll, H. P. et al. Afatinib restrains K-RAS-driven lung tumorigenesis. Sci Transl Med 10, doi:10.1126/scitranslmed.aao2301 (2018).

Moreira, (1993) Thalidomide Exerts its Inhibitory Action on Tumor Necrosis Factor Alpha by Enhancing MRNA Degradation, *J Exp Med*, 177, 1675-1680.

Muhlbauer, M. et al. PD-L1 is induced in hepatocytes by viral infection and by interferon-alpha and- gamma and mediates T cell apoptosis. J Hepatol 45, 520-528, doi:10.1016/j.jhep.2006.05.007 (2006).

Mulloy, et al. (2007) "Epidermal Growth Factor Receptor Mutants from Human Lung Cancers Exhibit Enhanced Catalytic Activity and Increased Sensitivity to Gefitinib," *Cancer Res*, 67, 2325-2330.

Murray, et al. (2014) Guanine nucleotide exchange factor Dock7 mediates HGF-induced glioblastoma cell invasion via Rac activation, Br J Cancer 110, 1307-1315.

Nair, A. B., and Jacob, S. (2016) A simple practice guide for dose conversion between animals and human, J Basic Clin Pharm 7, 27-31.

Nakamuta, et al. (2017) Dual role for DOCK7 in tangential migration of interneuron precursors in the postnatal forebrain, J Cell Biol 216, 4313-4330.

Nathanson, et al. (2014) Targeted therapy resistance mediated by dynamic regulation of extrachromosomal mutant EGFR DNA, Science 343, 72-76.

Nau, et al. (2010) Penetration of drugs through the blood-cerebrospinal fluid/blood-brain barrier for treatment of central nervous system infections, Clin Microbiol Rev 23, 858-883.

Negishi, et al. The Interferon (IFN) Class of Cytokines and the IFN Regulatory Factor (IRF) Transcription Factor Family. Cold Spring Harb Perspect Biol 10, doi:10.1101/cshperspect.a028423 (2018).

Nelson, et al. (2013) "Afatinib: Emerging Next-Generation Tyrosine Kinase Inhibitor for NSCLC" OncoTargets and Therapy 2013:6 pp. 135-143.

Nelson, et al., (2006) "Protocol for the Fast Chromatin Immunoprecipitation," (ChOP) Method, *Nat Protoc*, 1, 179-185.

Newman, et al. (2017) Interleukin-13 receptor alpha 2 cooperates with EGFRvIII signaling to promote glioblastoma multiforme, Nat Commun 8, 1913.

Nishikawa, et al. (1994) A mutant epidermal growth factor receptor common in human glioma confers enhanced tumorigenicity, Proc Natl Acad Sci U S A 91, 7727-7731.

Nishikawa, et al. (2004) Immunohistochemical analysis of the mutant epidermal growth factor, deltaEGFR, in glioblastoma, Brain Tumor Pathol 21, 53-56.

O'Reilly, M. A. (2005) Redox activation of p21Cip1/WAF1/Sdi1: a multifunctional regulator of cell survival and death, Antioxid Redox Signal 7, 108-118.

Ohashi, et al. (2013) "Epidermal Growth Factor Receptor Tyrosine Kinase Inhibitor-Resistant Disease." *J Clin Oncol*, 31, 1070-1080.

Ohgaki, et al. (2007) "Genetic Pathways to Primary and Secondary Gioblastoma," *Am J. Pathol*, 170, 1445-1453.

Ooi, et al. (2013) CUL3 and NRF2 mutations confer an NRF2 activation phenotype in a sporadic form of papillary renal cell carcinoma, Cancer Res 73, 2044-2051.

Orcutt, et al. (2011) Erlotinib-mediated inhibition of EGFR signaling induces metabolic oxidative stress through NOX4, *Cancer Res 71*, 3932-3940.

Padmanabhan, et al. (2006) Structural basis for defects of Keap1 activity provoked by its point mutations in lung cancer, *Mol Cell 21*, 689-700.

Padmanabhan, et al. (2008) Structural analysis of the complex of Keap1 with a prothymosin alpha peptide, *Acta Crystallogr Sect F Struct Biol Cryst Commun 64*, 233-238.

Paez, et al. (2004) EGFR mutations in lung cancer: correlation with clinical response to gefitinib therapy, *Science 304*, 1497-1500.

Pardrige (2015) "Targeted delivery of protein and gene medicines through the blood-brain barrier" *Clinical Pharmacology & Therapeutics* 97: 347-361.

Park, et al. (2009) The receptor interacting protein 1 inhibits p53 induction through NF-kappaB activation and confers a worse prognosis in glioblastoma, *Cancer Res 69*, 2809-2816.

Park, et al. (2018) Resistance to gefitinib and cross-resistance to irreversible EGFR-TKIs mediated by disruption of the Keap1-Nrf2 pathway in human lung cancer cells, *FASEB J*, fj201800011R.

Pathania, et al. (2018) Drug metabolizing enzymes and their inhibitors' role in cancer resistance, *Biomed Pharmacother 105*, 53-65.

Pao, et al. (2004) "EGF Receptor Gene Mutations are Common in Lung Cancers from "Never Smokers" and are associated with Sensitivity of Tumors to Gefitinib and Erlotinib," *Proc Natl Acad Sci USA*, 1010, 13306-13311.

Peereboom, et al. (2010) Phase II trial of erlotinib with temozolomide and radiation in patients with newly diagnosed glioblastoma multiforme, *J Neurooncol 98*, 93-99.

Pelosof, et al. (2017) GPX3 promoter methylation predicts platinum sensitivity in colorectal cancer, *Epigenetics 12*, 540-550.

Peng, et al. (2016) Suppression of NRF2-ARE activity sensitizes chemotherapeutic agent-induced cytotoxicity in human acute monocytic leukemia cells, *Toxicology and applied pharmacology 292*, 1-7.

Peter, et al. (2004) BAR domains as sensors of membrane curvature: the amphiphysin BAR structure, *Science 303*, 495-499.

Pillay, et al. (2009) "The Plasticity of Oncogene Addiction : Implications for Targeted Therapies Directed to Receptor Tyrosine Kinases," *Neoplasia*, 11, 448-458.

Pingle, et al. "In Silico Modeling Predicts Drug Sensitivity of Patient-Derived Cancer Cells," *J. Transl Med*, 12, 128.

Polewski, et al. (2016) Increased Expression of System xc- in Glioblastoma Confers an Altered Metabolic State and Temozolomide Resistance, *Mol Cancer Res 14*, 1229-1242.

Polewski, et al. (2017) SLC7A11 Overexpression in Glioblastoma Is Associated with Increased Cancer Stem Cell-Like Properties, *Stem Cells Dev 26*, 1236-1246.

Polonen, et al. (2019) Nrf2 and SQSTM1/p62 jointly contribute to mesenchymal transition and invasion in glioblastoma, *Oncogene*.

Prahallad, A. et al. Unresponsiveness of colon cancer to BRAF(V600E) inhibition through feedback activation of EGFR. Nature 483, 100-103, doi:10.1038/nature10868 (2012).

Prendergast, et al. (2009) BAR the door: cancer suppression by amphiphysin-like genes, Biochim Biophys Acta 1795, 25-36.

Puchalski, et al. (2018) An anatomic transcriptional atlas of human glioblastoma, Science 360, 660-663.

Puliyappadamba V.T. et al. Opposing effect of EGFRwt on EGFRvIII mediated NF-kappaB activation with RIP1 as a cell death switch. Cell Reports 4, 764-775. 2013.

Qian, et al. (2009) Erlotinib activates mitochondrial death pathways related to the production of reactive oxygen species in the human non-small cell lung cancer cell line A549, Clin Exp Pharmacol Physiol 36, 487-494.

Raizer, et al. (2010) "A phase II trial of erlotinib in patients with recurrent malignant gliomas and nonprogressive glioblastoma multiforme postradiation therapy," *Neuro Oncol* 12, 95-103.

Ramalingam, et al. (2008) Bin3 deletion causes cataracts and increased susceptibility to lymphoma during aging, Cancer Res 68, 1683-1690.

Ramnarain, et al. (2006) Differential gene expression analysis reveals generation of an autocrine loop by a mutant epidermal growth factor receptor in glioma cells, Cancer Res 66, 867-874.

Rasmussen, et al. (2016) BRCA1-regulated RRM2 expression protects glioblastoma cells from endogenous replication stress and promotes tumorigenicity, Nat Commun 7, 13398.

Reardon, et al. (2010) Phase 2 trial of erlotinib plus sirolimus in adults with recurrent glioblastoma, J Neurooncol 96, 219-230.

Rich, et al. (2004) Phase II trial of gefitinib in recurrent glioblastoma, J Clin Oncol 22, 133-142.

(56) References Cited

OTHER PUBLICATIONS

Rickardson, L. et al. Identification of molecular mechanisms for cellular drug resistance by combining drug activity and gene expression profiles. Br J Cancer 93, 483-492, doi:10.1038/sj.bjc.6602699 (2005).

Robert, et al. (2015) SLC7A11 expression is associated with seizures and predicts poor survival in patients with malignant glioma, Sci Transl Med 7, 289ra286.

Rocha, et al. (2016) NRF2 and glutathione are key resistance mediators to temozolomide in glioma and melanoma cells, Oncotarget 7, 48081-48092.

Rojo de la Vega, et al. (2018) NRF2 and the Hallmarks of Cancer, Cancer Cell.

Romero, et al. (2017) Keap1 loss promotes Kras-driven lung cancer and results in dependence on glutaminolysis, Nature medicine 23, 1362-1368.

Roos, et al. (2018) EGFRvIII-Stat5 Signaling Enhances Glioblastoma Cell Migration and Survival, Mol Cancer Res 16, 1185-1195.

Roth, P., and Weller, M. (2014) Challenges to targeting epidermal growth factor receptor in glioblastoma: escape mechanisms and combinatorial treatment strategies, Neuro Oncol 16 Suppl 8, viii14-19.

Rubio-Moscardo, et al. (2005) Characterization of 8p21.3 chromosomal deletions in B-cell lymphoma: TRAIL-R1 and TRAIL-R2 as candidate dosage-dependent tumor suppressor genes, Blood 106, 3214-3222.

Rusch, V. et al. Differential expression of the epidermal growth factor receptor and its ligands in primary non-small cell lung cancers and adjacent benign lung. Cancer Res 53, 2379-2385 (1993).

Russell, et al. (2017) Sex as a biological variable in response to temozolomide, Neuro Oncol.

Russell, et al. (2018) PTEN expression by an oncolytic herpesvirus directs T-cell mediated tumor clearance, Nat Commun 9, 5006.

Rusthoven, et al. (2016) Combined-Modality Therapy With Radiation and Chemotherapy for Elderly Patients With Glioblastoma in the Temozolomide Era: A National Cancer Database Analysis, JAMA Neurol 73, 821-828.

Sabharwal, S. S., and Schumacker, P. T. (2014) Mitochondrial ROS in cancer: initiators, amplifiers or an Achilles' heel?, Nat Rev Cancer 14, 709-721.

Santosh, V., and Sravya, P. (2017) Glioma, glutamate (SLC7A11) and seizures—a commentary, Ann Transl Med 5, 214.

Sarkaria, et al. (2006) Use of an orthotopic xenograft model for assessing the effect of epidermal growth factor receptor amplification on glioblastoma radiation response, Clin Cancer Res 12, 2264-2271.

Sathornsumetee, et al. (2010) Phase II trial of bevacizumab and erlotinib in patients with recurrent malignant glioma, Neuro Oncol 12, 1300-1310.

Sato, et al. (2018) The ferroptosis inducer erastin irreversibly inhibits system xc- and synergizes with cisplatin to increase cisplatin's cytotoxicity in cancer cells, Sci Rep 8, 968.

Sausville, et al. (2006) "Contributions of Human Tumor Xenografts to Anticancer Drug Development," Cancer Research, vol. 66, pp. 3351-3354.

Schnell, et al. (2014) Pharmacokinetics of afatinib in subjects with mild or moderate hepatic impairment, Cancer Chemother Pharmacol 74, 267-275.

Schuster, et al. (2015) "A Phase II, Multicenter rial of rindopepimut (CDX-110) in Newly Diagnoses Glioblastoma: the Act III Study," Neuro Oncol, 17, 854-861.

Sedger, et al. (2014) TNF and TNF-receptors: From Mediators of Cell Death and Inflammation to Therapeutic Giants—Past, Present, and Future, Cytokine Growth Factor Rev , 25, 453-472.

Seike, et al. (2009) MiR-21 is an EGFR-Regulated Anti-Apoptopic Factor in Lung Cancer in Never-Smokers, Pro Natl Acad Sci USA, 106, 12085-12090.

Sethi, et al. (2008) "TNF: A Master Switch for Inflammation to Cancer." Frontiers in Bioscience: a Journal and Virtual Library 13, 5094-5107.

Shah, et al. (2016) Survival Trends in Elderly Patients with Glioblastoma in the United States: a Population-based Study, Anticancer Res 36, 4883-4886.

Sharma, et al. Epidermal growth factor receptor mutations in lung cancer. Nat Rev Cancer 7, 169-181, doi:10.1038/nrc2088 (2007).

Shi, et al. (2017) All-trans retinoic acid enhances temozolomide-induced autophagy in human glioma cells U251 via targeting Keap1/Nrf2/ARE signaling pathway, Oncol Lett 14, 2709-2714.

Shibata, et al. (2008) Cancer related mutations in NRF2 impair its recognition by Keap1-Cul3 E3 ligase and promote malignancy, Proc Natl Acad Sci U S A 105, 13568-13573.

Shingu, et al. (2015) "Abstract 3483: Synergistic combination therapy with molecular targeted drugs in glioma stem-like cells," Cancer Research. AACR 106th Annual Meeting, 2015, Philadelphia, PA.

Shukla, et al. (2011) Inhibition of xc(-) transporter-mediated cystine uptake by sulfasalazine analogs, Bioorg Med Chem Lett 21, 6184-6187.

Silva-Islas, C. A., and Maldonado, P. D. (2018) Canonical and non-canonical mechanisms of Nrf2 activation, Pharmacol Res 134, 92-99.

Simionescu-Bankston, et al. (2013) The N-BAR domain protein, Bin3, regulates Rac1- and Cdc42-dependent processes in myogenesis, Dev Biol 382, 160-171.

Singh, et al. (2006) Dysfunctional KEAP1-NRF2 interaction in non-small-cell lung cancer, PLoS Med 3, e420.

Singh, et al. (2016) Small Molecule Inhibitor of NRF2 Selectively Intervenes Therapeutic Resistance in KEAP1-Deficient NSCLC Tumors, ACS chemical biology 11, 3214-3225.

Sivanand, et al. (2012) A validated tumorgraft model reveals activity of dovitinib against renal cell carcinoma, Sci Transl Med 4, 137ra175.

Sleire, et al. (2015) Drug repurposing: sulfasalazine sensitizes gliomas to gamma knife radiosurgery by blocking cystine uptake through system Xc-, leading to glutathione depletion, Oncogene 34, 5951-5959.

Snell, et al. Type I Interferon in Chronic Virus Infection and Cancer. Trends Immunol 38, 542-557, doi:10.1016/j.it.2017.05.005 (2017).

Solis, et al. (2010) Nrf2 and Keap1 abnormalities in non-small cell lung carcinoma and association with clinicopathologic features, Clin Cancer Res 16, 3743-3753.

Song, G. et al. E3 ubiquitin ligase RNF128 promotes innate antiviral immunity through K63-linked ubiquitination of TBK1. Nat Immunol 17, 1342-1351, doi:10.1038/ni.3588 (2016).

Sontheimer, H., and Bridges, R. J. (2012) Sulfasalazine for brain cancer fits, Expert Opin Investig Drugs 21, 575-578.

Sordella, et al. (2004) "Gefitinib-Sensitizing EGFR Mutations in Lung Cancer Activate Anti-Apoptotic Pathways." Science, 305, 1163-1167.

Sorensen, et al. (2018) High expression of cystine-glutamate antiporter xCT (SLC7A11) is an independent biomarker for epileptic seizures at diagnosis in glioma, J Neurooncol 138, 49-53.

Starheim, et al. (2016) Intracellular glutathione determines bortezomib cytotoxicity in multiple myeloma cells, Blood Cancer J 6, e446.

Strommel, et al. (2007) "Coactivation of Receptor Tyrosine Kinases Affects the Response of Tumor Cells to Targeted Therapies," Science, 318, 287-290.

Stupp, et al. (2005) Radiotherapy plus concomitant and adjuvant temozolomide for glioblastoma, N Engl J Med 352, 987-996.

Sullins, A. K., and Abdel-Rahman, S. M. (2013) Pharmacokinetics of antibacterial agents in the CSF of children and adolescents, Paediatr Drugs 15, 93-117.

Sun, et al. (1998) Epidermal Growth Factor Activation of NF-kappaB is Mediated Through IkappaBalpha Degradation and Intracellular Free Calcium, Oncogene, 16, 2095-2102.

Sun, C. & Bernards, R. Feedback and redundancy in receptor tyrosine kinase signaling: relevance to cancer therapies. Trends in biochemical sciences 39, 465-474, doi:10.1016/j.tibs.2014.08.010 (2014).

(56) References Cited

OTHER PUBLICATIONS

Sun, C. et al. Intrinsic resistance to MEK inhibition in KRAS mutant lung and colon cancer through transcriptional induction of ERBB3. Cell Rep 7, 86-93, doi:10.1016/j.celrep.2014.02.045 (2014).

Talasila, et al. (2013) EGFR wild-type amplification and activation promote invasion and development of glioblastoma independent of angiogenesis, Acta neuropathologica 125, 683-698.

Tamura, et al. (2017) Bevacizumab for malignant gliomas: current indications, mechanisms of action and resistance, and markers of response, Brain Tumor Pathol 34, 62-77.

Tan, et al. (2016) Stress-Induced EGFR Trafficking: Mechanisms, Functions, and Therapeutic Implications, Trends Cell Biol 26, 352-366.

Tang, et al. (1997) The autocrine loop of TGF-alpha/EGFR and brain tumors, J Neurooncol 35, 303-314.

Tang, et al. Jak/Stat3 signaling promotes somatic cell reprogramming by epigenetic regulation. Stem Cells, Dec. 2012, vol. 30, No. 12, pp. 2645-2656.

Tang, et al. (2014) Cdk5-dependent Mst3 phosphorylation and activity regulate neuronal migration through RhoA inhibition, J Neurosci 34, 7425-7436.

Taylor, Te et al. "Targeting EGFR for Treatment of Glioblastoma: Molecular Basis to Overcome Resistance," *Current Cancer Drug Targets.* Mar. 2021, 12, No. 3.

Terai, H. et al. ER Stress Signaling Promotes the Survival of Cancer "Persister Cells" Tolerant to EGFR Tyrosine Kinase Inhibitors. *Cancer Res* 78, 1044-1057, doi:10.1158/0008-5472.CAN-17-1904 (2018).

The Cancer Genome Atlas Research Network (2008) Comprehensive genomic characterization defines human glioblastoma genes and core pathways, *Nature 455*, 1061-1068.

Thungappa, S. et al. Immune checkpoint inhibitors in lung cancer: the holy grail has not yet been found. *ESMO Open* 2, e000162, doi:10.1136/esmoopen-2017-000162 (2017).

Trinchieri, G. Type I interferon: friend or foe? *J Exp Med* 207, 2053-2063, doi:10.1084/jem.20101664 (2010).

Trudgian, D. C. et al. Comparative evaluation of label-free SINQ normalized spectral index quantitation in the central proteomics facilities pipeline. *Proteomics* 11, 2790-2797 (2011).

Tsai, M. H. et al. Gene expression profiling of breast, prostate, and glioma cells following single versus fractionated doses of radiation. Cancer Res 67, 3845-3852, doi:10.1158/0008-5472.CAN-06-4250 (2007).

Tsao, et al. "Erlotinib in Lung Cancer—Molecular and Clinical Predictors of Outcome," *N Engl J Med*, 353, 133-144.

Tsuchihashi, et al. (2016) The EGF Receptor Promotes the Malignant Potential of Glioma by Regulating Amino Acid Transport System xc(-), Cancer Res 76, 2954-2963.

Tsunoda, et al. (1999) "Estimating Transcription Factor Bindability on DNA," *Bioinformatics*, 15, 622-630.

Tu, D. et al. Structure and ubiquitination-dependent activation of TANK-binding kinase 1. Cell Rep 3, 747-758, doi:10.1016/j.celrep. 2013.01.033 (2013).

Velu, et al. (1987) Epidermal-growth-factor-dependent transformation by a human EGF receptor proto-oncogene, *Science 238*, 1408-1410.

Venere, et al. (2015) The mitotic kinesin KIF11 is a driver of invasion, proliferation, and self-renewal in glioblastoma, *Sci Transl Med 7*, 304ra143.

Verhaak, et al. (2010) Integrated genomic analysis identifies clinically relevant subtypes of glioblastoma characterized by abnormalities in PDGFRA, IDH1, EGFR, and NF1, *Cancer Cell 17*, 98-110.

Verma, et al. (2015) Isoniazid prevents Nrf2 translocation by inhibiting ERK1 phosphorylation and induces oxidative stress and apoptosis, *Redox Biol 6*, 80-92.

Volante, M. et al. Epidermal growth factor ligand/receptor loop and downstream signaling activation pattern in completely resected nonsmall cell lung cancer. *Cancer* 110, 1321-1328, doi:10.1002/cncr.22903 (2007).

Wainwright, et al. (2014) Durable therapeutic efficacy utilizing combinatorial blockade against IDO, CTLA-4 and PD-L1 in mice with brain tumors, Clin Cancer Res.

Wajant, et al. (2003) "Tumor Necrosis Factor Signaling," *Cell Death Differ*, 10, 45-65.

Wang, et al. (2015) Identification of proteins responsible for adriamycin resistance in breast cancer cells using proteomics analysis, Sci Rep 5, 9301.

Wang, et al. (2016) "A single-center, single-arm phase II trial: Efficacy and safety of thalidomide on advanced NSCLC patients with secondary drub resistance of first generation EGRF-TKI" Anti-Tumor Pharmacy 20160628 Editorial Department of Anti-Tumor Pharmacy CHN, 6(3): 193-197.

Wang, et al. (2017) "Use of erlotinib and thalidomide in advanced NSCLC patients with acquired resistance to erlotinib: A pilot study," Pathology—Research and Practice 214(2): 263-267.

Wang, L., Li, S. & Dorf, M. E. NEMO binds ubiquitinated TANK-binding kinase 1 (TBK1) to regulate innate immune responses to RNA viruses. PLoS One 7, e43756, doi:10.1371/journal.pone. 0043756 (2012).

Warta, R., and Herold-Mende, C. (2017) Helping EGFR inhibition to block cancer, *Nat Neurosci 20*, 1035-1037.

Weichselbaum, R. R. et al. An interferon-related gene signature for DNA damage resistance is a predictive marker for chemotherapy and radiation for breast cancer. *Proc Natl Acad Sci U S A* 105, 18490-18495, doi:10.1073/pnas.0809242105 (2008).

Weinstein, (2002) Cancer. Addition to Oncogenes—the Achilles Heel of Cancer, Science 297, 63-64.

Weller, et al. (2017) Rindopepimut with temozolomide for patients with newly diagnosed, EGFRvIII-expressing glioblastoma (ACT IV): a randomised, double-blind, international phase 3 trial, *The lancet oncology 18*, 1373-1385.

Westpal (2017) "EGFR as a Target for Glioblastoma Treatment: An Unfulfilled Promise" DNS Drugs 31:723-735.

Wind, et al. (2017) Clinical Pharmacokinetics and Pharmacodynamics of Afatinib, *Clin Pharmacokinet 56*, 235-250.

Wolff, et al. (2007) American Society of Clinical Oncology/College of American Pathologists guideline recommendations for human epidermal growth factor receptor 2 testing in breast cancer, J Clin Oncol 25, 118-145.

Wong, et al. (1992) Structural alterations of the epidermal growth factor receptor gene in human gliomas, Proc Natl Acad Sci U S A 89, 2965-2969.

Worley, et al. (2018) GPx3 supports ovarian cancer progression by manipulating the extracellular redox environment, Redox Biol.

Wykosky, et al. (2015) A urokinase receptor-Bim signaling axis emerges during EGFR inhibitor resistance in mutant EGFR glioblastoma, Cancer Res 75, 394-404.

Xie, et al. (2014) Targeting adaptive glioblastoma: an overview of proliferation and invasion, Neuro Oncol 16, 1575-1584.

Xie, et alD. (2017) The Tumor Suppressor p53 Limits Ferroptosis by Blocking DPP4 Activity, *Cell Rep 20*, 1692-1704.

Yamada, et al. (2013) High expression of ATP-binding cassette transporter ABCC11 in breast tumors is associated with aggressive subtypes and low disease-free survival, *Breast cancer research and treatment 137*, 773-782.

Yamamoto, et al. (2013) DOCK7 is a critical regulator of the RAGE-Cdc42 signaling axis that induces formation of dendritic pseudopodia in human cancer cells, *Oncology reports 29*, 1073-1079.

Yan, Y et al. "Targeting autophagy to sensitive glioma to temozolomide treatment," *Journal of Experimental and Clinical Cancer Research.* Feb. 2, 2016, 35, No. 23.

Yanaihara, et al. (2006) Unique MicroRNA Molecular Profiles in Lung Cancer Diagnosis and Prognosis, *Cancer Cell*, 9, 189-198.

Ye, et al. (2007) Genomic assessments of the frequent loss of heterozygosity region on 8p21.3-p22 in head and neck squamous cell carcinoma, *Cancer Genet Cytogenet 176*, 100-106.

Ye, M. et al. Activation of the Aryl Hydrocarbon Receptor Leads to Resistance to EGFR TKIs in Non-Small Cell Lung Cancer by Activating Src-mediated Bypass Signaling. *Clin Cancer Res* 24, 1227-1239, doi:10.1158/1078-0432.CCR-17-0396 (2017).

(56) References Cited

OTHER PUBLICATIONS

Ye, Z. et al. Prevalent Homozygous Deletions of Type I Interferon and Defensin Genes in Human Cancers Associate with Immunotherapy Resistance. *Clin Cancer Res* 24, 3299-3308, doi:10.1158/1078-0432. CCR-17-3008 (2018).

Yoneyama, et al. Control of IRF-3 activation by phosphorylation. *J Interferon Cytokine Res* 22, 73-76, doi:10.1089/107999002753452674 (2002).

Yoshida, T. et al. Tyrosine phosphoproteomics identifies both codrivers and cotargeting strategies for T790M-related EGFR-TKI resistance in non-small cell lung cancer. Clin Cancer Res 20, 4059-4074, doi:10.1158/1078-0432.CCR-13-1559 (2014).

Yu et al. (2013) "Afatinib-new therapy option for EGFR-mutant lung cancer," Nature Reviews/Clinical Oncology 10: 551-552.

Yu, H. A. et al. Analysis of tumor specimens at the time of acquired resistance to EGFR-TKI therapy in 155 patients with EGFR-mutant lung cancers. Clin Cancer Res 19, 2240-2247, doi:10.1158/1078-0432.CCR-12-2246 (2013).

Yuan, et al. (2012) A positive/negative ion-switching, targeted mass spectrometry-based metabolomics platform for bodily fluids, cells, and fresh and fixed tissue, Nat Protoc 7, 872-881.

Yun, et al. (2007) Structures of Lung Cancer-Derived EGFR Mutants and Inhibitor Complexes: mechanism of Activation and Insights into Differential Inhibitor Sensitivity, *Cancer Cell*, 11, 217-227.

Zhang, et al. (2012) "MicroRNA 21 Modulates the Levels of Reactive Oxygen Species by Targeting SOD3 and TNFalpha," *Cancer Res*, 72, 4707-4713.

Zanca, et al. (2017) Glioblastoma cellular cross-talk converges on NF-kappaB to attenuate EGFR inhibitor sensitivity, Genes Dev 31, 1212-1227.

Zhang, et al. TRIM32 protein modulates type I interferon induction and cellular antiviral response by targeting MITA/STING protein for K63-linked ubiquitination. J Biol Chem 287, 28646-28655, doi:10.1074/jbc.M112.362608 (2012).

Zhang, Z. et al. Activation of the AXL kinase causes resistance to EGFR-targeted therapy in lung cancer. Nat Genet 44, 852-860, doi:10.1038/ng.2330 (2012).

Zhang, et al. (2016) ROS and ROS-Mediated Cellular Signaling, Oxid Med Cell Longev 2016, 4350965.

Zhang, et al. (2017) Efficacy of afatinib, an irreversible ErbB family blocker, in the treatment of intracerebral metastases of non-small cell lung cancer in mice, Acta Pharmacol Sin 38, 233-240.

Zhang, L., and Wang, H. (2017) FTY720 inhibits the Nrf2/ARE pathway in human glioblastoma cell lines and sensitizes glioblastoma cells to temozolomide, Pharmacol Rep 69, 1186-1193.

Zheng, et al. (1993) Toxicokinetics of sulfasalazine (salicylazosulfapyridine) and its metabolites in B6C3F1 mice, Drug Metab Dispos 21, 1091-1097.

Zhou, et al. (2009) Dynamic near-infrared optical imaging of 2-deoxyglucose uptake by intracranial glioma of athymic mice, *PLoS One* 4, e8051.

Zhu, et al. (2013) Nrf2 is required to maintain the self-renewal of glioma stem cells, *BMC Cancer* 13, 380.

Zhu, et al. (2014) "Multiple Lesions in Receptor Tyrosine Kinase Pathway Determine Glioblastoma Response to Pan-ERBB Inhibitor PF-00299804 and P13K/mTOR Dual Inhibitor PF-05212384" *Cancer Biol Ther*, 15, 815-822.

Zhu, et al. (2018) Glutathione reductase mediates drug resistance in glioblastoma cells by regulating redox homeostasis, *J Neurochem* 144, 93-104.

Zhu, M., and Fahl, W. E. (2001) Functional characterization of transcription regulators that interact with the electrophile response element, *Biochem Biophys Res Commun 289*, 212-219.

Zitka, et al. (2012) Redox status expressed as GSH:GSSG ratio as a marker for oxidative stress in paediatric tumour patients, *Oncol Lett 4*, 1247-1253.

Zitvogel, et al. Type I interferons in anticancer immunity. *Nat Rev Immunol* 15, 405-414, doi:10.1038/nri3845 (2015).

Boehringer Ingelheim (Sep. 28, 2016), LUX-Lung 7: A Phase IIb Trial of Afatinib (BIBW2992) Versus Gefitinib for the Treatment of 1st Line EGFR Mutation Positive Adenocarcinoma of the Lung, Version 58, NCT1466660.

Keith RL, Miller YE. Lung cancer chemoprevention: current status and future prospects. Nat Rev Clin Oncol. Jun. 2013;10(6):334-43.

Lee HY, Kim JW, Yeo CD. A case of tuberculosis reactivation suspected of cancer progression during oral tyrosine kinase inhibitor treatment in a patient diagnosed as non-small cell lung cancer. J Thorac Dis. Aug. 2017;9(8):E709-E713.

Lopes et al. ((2015), Identifying activating mutations in the EGFR gene: prognostic and therapeutic implications in non-small cell lung cancer*, J Bras Pneumol, 41, 365-375.

Pickup (1979), Clinical Pharmacokinetics of Prednisone and Prednisolone, Clinical Pharmacokinetics, 4, 111-128.

Shields et. al. (Jun. 27, 2016), Dexamethasone Effects in Patients With Refractory Non-Small Cell Lung Cancer Using FLT Positron Emission Tomography, Version 1, NCT02819024.

Tani et. al. (2016), Successful treatment of non-small-cell lung cancer with afatinib and a glucocorticoid following gefitinib- and erlotinib-induced interstitial lung disease: A case report, Molecular and Clinical Oncology, 5, 488-490.

"Causes, Risk Factors, and Prevention of Cancer in Children" [Online]. American Cancer Society. Published online on Jan. 14, 2024. <URL: https://www.cancer.org/cancer/childhood-cancer/causes-risk-factors-prevention.html> (Year: 2024).

"Dealing with chronic cancer" [Online] MedlinePlus. Published online on Mar. 31, 2024. <URL: https://medlineplus.gov/ency/patientinstructions/000933.htm> (Year: 2024).

Coussens NP, Braisted JC, Peryea T, Sittampalam GS, Simeonov A, Hall MD. Small-Molecule Screens: A Gateway to Cancer Therapeutic Agents with Case Studies of Food and Drug Administration-Approved Drugs. Pharmacol Rev. Oct. 2017;69(4):479-496.

Gridelli C, et al., First-line erlotinib followed by second-line cisplatin-gemcitabine chemotherapy in advanced non-small-cell lung cancer: the TORCH randomized trial. J Clin Oncol. Aug. 20, 2012;30(24):3002-11.

Jazieh AR, et al., Prognostic factors in patients with surgically resected stages I and II non-small cell lung cancer. Ann Thorac Surg. Oct. 2000;70(4):1168-71.

Kankia IH, et al., NRF2 Regulates HER1 Signaling Pathway to Modulate the Sensitivity of Ovarian Cancer Cells to Lapatinib and Erlotinib. Oxid Med Cell Longev. 2017;2017:1864578.

Kawano Y, et al., Blocking IFNAR1 inhibits multiple myeloma-driven Treg expansion and immunosuppression. J Clin Invest. Jun. 1, 2018;128(6):2487-2499.

Li H, Stokes W, Chater E, Roy R, de Bruin E, Hu Y, Liu Z, Smit EF, Heynen GJ, Downward J, Seckl MJ, Wang Y, Tang H, Pardo OE. Decreased glutathione biosynthesis contributes to EGFR T790M-driven erlotinib resistance in non-small cell lung cancer.

Peng H, et al., Suppression of NRF2-ARE activity sensitizes chemotherapeutic agent-induced cytotoxicity in human acute monocytic leukemia cells. Toxicol Appl Pharmacol. Feb. 1, 2016;292:1-7.

Shepherd FA, et al., Erlotinib in previously treated non-small-cell lung cancer. N Engl J Med. Jul. 14, 2005;353(2):123-32.

Song S, et al., The Hippo Coactivator YAP1 Mediates EGFR Overexpression and Confers Chemoresistance in Esophageal Cancer. Clin Cancer Res. Jun. 1, 2015;21(11):2580-90.

Verma AK, et al., Isoniazid induces apoptosis: Role of oxidative stress and inhibition of nuclear translocation of nuclear factor (erythroid-derived 2)-like 2 (Nrf2). Life Sci. Apr. 15, 2018;199:23-33.

Wang Q, et al., Akt/mTOR and AMPK signaling pathways are responsible for liver X receptor agonist GW3965-enhanced gefitinib sensitivity in non-small cell lung cancer cell lines. Transl Cancer Res. Feb. 2019;8(1):66-76.

Whittington PJ, etal., DNA vaccination controls Her-2+ tumors that are refractory to targeted therapies. Cancer Res. Sep. 15, 2008568(18):7502-11.

Yamadori, T, et al., Interaction between Nrf2 and EGFR signaling in the proliferation of NSCLC cells. Journal of Clinical Oncology vol. 28, No. 15_suppl Meeting Abstract: 2010 ASCO Annual Meeting I e21062 May 2010.

(56)     References Cited

OTHER PUBLICATIONS

"Non-Small Cell Lung Cancer Treatment (PDQ®)-Patient Version" [Online]. National Cancer Institute. Published on May 16, 2025. Retrieved from Internet on Dec. 11, 2025. <URL: https://www.cancer.gov/types/lung/patienUnon-small-cell-lung-treatment-pdq> (Year: 2025).

"Small Cell Lung Cancer Treatment (PDQ®)-Patient Version" [Online]. National Cancer Institute. Published on May 8, 2025. Retrieved from Internet on Dec. 11, 2025. <URL: https://www.cancer.gov/types/lung/patienUsmall-cell-lung-treatment-pdq> (Year: 2025).

He et al. (2013) Blockade of Glioma Proliferation Through Allosteric Inhibition of JAK2. Sci Signal. Jul. 9, 2013;6(283):ra55.

Keith, R.L. et al. (2010) Chemoprevention of murine lung cancer by gefitinib in combination with prostacyclin synthase overexpression. Lung Cancer, 2010. vol. 70(1):37-42.

Keith, R.L. et al. (2013) Lung cancer chemoprevention: current status and future prospects. Nat Rev Clin Oneal, 2013. vol. 10(6): 334-343.

Sattler, M. et al. (2023) A Closer Look at EGFR Inhibitor Resistance in Non-Small Cell Lung Cancer through the Lens of Precision Medicine. J Clin Med, 2023. vol. 12(5): 1936. Published Mar. 1, 2023.

Tan et al. (2019) A STAT3-based gene signature stratifies glioma patients for targeted therapy. Nat Commun 10, 3601 (2019).

Wang et al. (2012) "Successful Erlotinib Rechallenge in a Non-Small Cell Lung Cancer Patient With Erlotinib-Induced Interstitial Lung Disease (ILD)," Chest. 142(4_MeetingAbstracts): 654A.

Wen et al. (2015) Synergistic anti-tumor effect of combined inhibition of EGFR and JAK/STAT3 pathways in human ovarian cancer. Molecular Cancer (2015) 14: 100.

* cited by examiner

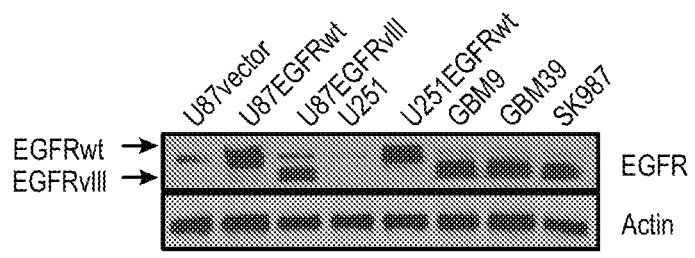
FIG. 1A
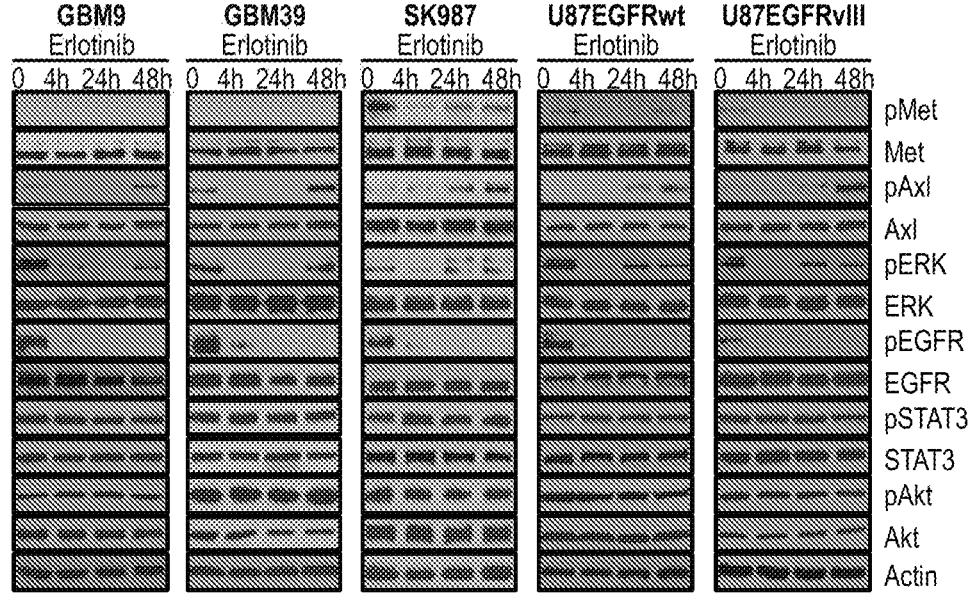
FIG. 1B    FIG. 1C    FIG. 1D    FIG. 1E    FIG. 1F
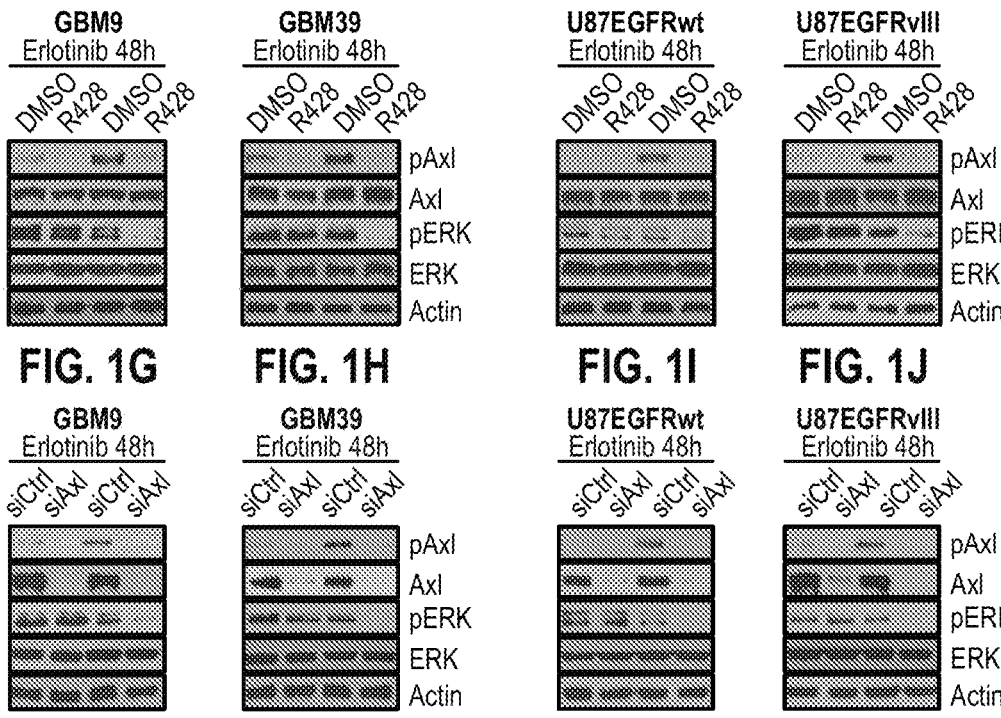
FIG. 1G    FIG. 1H    FIG. 1I    FIG. 1J
FIG. 1K    FIG. 1L    FIG. 1M    FIG. 1N

U251EGFR
Erlotinib
0 4h 24h 48h pMet
Met
pAxl
Axl
pERK
ERK
pEGFR
EGFR
pJNK
JNK
pSTAT3
STAT3
pAkt
Akt
Actin

FIG. 8A

GBM9
Afatinib
0 4h 24h 48h pAxl
Axl
pERK
ERK
pSTAT3
STAT3
pAkt
Akt
Actin

FIG. 8B

GBM9
Erlotinib(10uM)
0 4h 24h 48h

FIG. 8C

GBM39
Erlotinib(10uM)
0 4h 24h 48h pSTAT3
STAT3
pAkt
Akt
Actin

FIG. 8D

U87EGFRwt
Erlotinib(10uM)
0 4h 24h 48h pSTAT3
STAT3
pAkt
Akt
Actin

FIG. 8E

U87EGFRvIII
Erlotinib(10uM)
0 4h 24h 48h pSTAT3
STAT3
pAkt
Akt
Actin

FIG. 8F

GBM9
Afatinib
0 4h 24h 48h pSTAT3
STAT3
pAkt
Akt
Actin

FIG. 8G

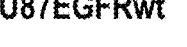

U87EGFRwt

S  SF  SF+DMSO pEGFR
EGFR
pERK
ERK
Actin

FIG. 8H

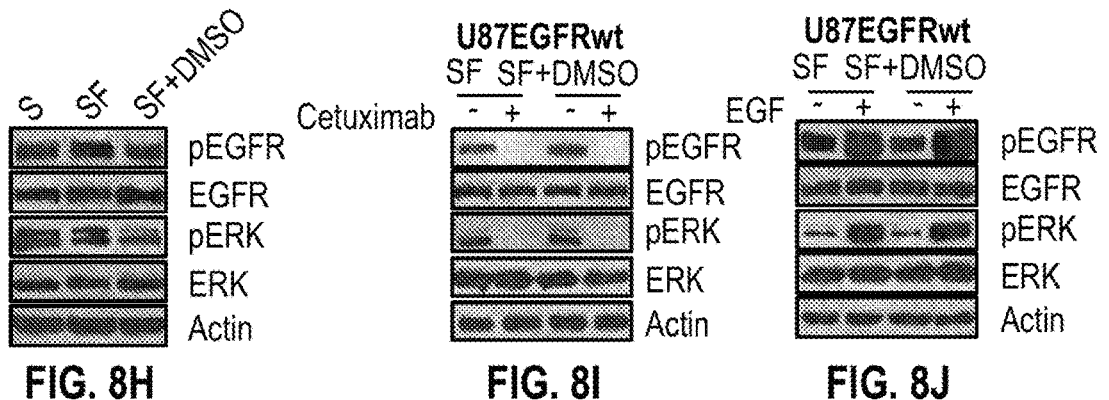

U87EGFRwt
SF  SF+DMSO
Cetuximab  -  +  -  + pEGFR
EGFR
pERK
ERK
Actin

FIG. 8I

U87EGFRwt
SF  SF+DMSO
EGF  -  +  -  + pEGFR
EGFR
pERK
ERK
Actin

FIG. 8J

GBM9

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggatctgacc tcagtgtatc                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tggttgtctt cactagcgat                                              20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
cccagggacc tctctctaat ca                                           22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gctacaggct tgtcactcgg                                              20

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
catcaacaag tatgggtctc cgt                                          23

<210> SEQ ID NO 6
<211> LENGTH: 23
<212> TYPE: DNA
```

```
<213> ORGANISM: Artificial Sequence
<220> FEATURE:
<223> OTHER INFORMATION: primer

<400> SEQUENCE: 6
gttctcctgg ctgcattcgt tga                                            23

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gtgaaggtcg gagtcaacgg                                                20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tgatgacaag cttcccgttc tc                                             22
```

METHODS AND COMPOSITIONS FOR TREATING CANCER

CROSS REFERENCE TO RELATED APPLICATIONS

This application is a division of U.S. application Ser. No. 15/940,802, filed Mar. 29, 2018, which claims the benefit of U.S. Provisional Application No. 62/478,500, filed Mar. 29, 2017, the content of which are incorporated herein by reference in their entireties

STATEMENT REGARDING FEDERALLY SPONSORED RESEARCH

This invention was made with government support under grant nos. R01 NS062080, 1R01CA149461, 1R01CA197796, 1R01CA194578, and 1R21CA202403 awarded by the National Institutes of Health (NIH), grant no. 101BX092559 awarded by the Office of Medical Research, Department of Veterans Affairs, and in part by grant no. NNX16AD78G awarded by the National Aeronautics and Space Administration. The government has certain rights in the invention.

REFERENCE TO SEQUENCE LISTING

The Sequence Listing submitted Mar. 22, 2022 as a text file named "37759_0231U1_ST25.txt," created on Mar. 22, 2022, and having a size of 1,780 bytes is hereby incorporated by reference pursuant to 37 C.F.R. § 1.52(e)(5).

FIELD OF THE INVENTION

The present invention is related to pharmaceutical compositions and methods for treating cancer.

BACKGROUND OF THE INVENTION

The identification of genetic abnormalities that are specific to cancer cells has made it possible to develop targeted treatments. The EGFR is a prime target in this therapeutic approach, since it is overexpressed in many types of cancers and may be a key driver of the malignant phenotype. An exciting development in recent years was the identification of EGFR activating mutations in a significant subset of lung cancers that render cells harboring such mutations to become oncogene addicted and very sensitive to the effects of EGFR tyrosine kinase inhibitors (TKIs). However, the inevitable development of secondary resistance has limited the effectiveness of EGFR inhibition in lung cancer. The development of secondary resistance in lung cancer has spurred intense investigation into mechanisms of EGFR TKI resistance and resulted in important insights into secondary resistance to EGFR TKIs in lung cancer. The major mechanisms identified in lung cancer include the emergence of EGFR mutations such as the T790M mutation and activation of other receptor tyrosine kinases such as Met or Axl that confer resistance to EGFR TKIs. In addition to genetic and delayed mechanisms, rapid feedback loops with activation of STAT3 have also been invoked to mediated EGFR TKI resistance in lung cancer cells with EGFR activating mutations. However, most EGFR expressing tumors both in the lung and the brain do not appear to be oncogene addicted and EGFR TKIs, so far, have not been effective in such cancers.

EGFR gene amplification and increased EGFR expression are detected in 40-50% GBMs, the most common primary malignant adult brain tumor. EGFRvIII is the most common oncogenic EGFR mutant in GBM and may be more sensitive to EGFR inhibition. There has been a substantial, and thus far, unsuccessful effort to inhibit the EGFR as a therapeutic strategy in GBM. While not much is known about what mediates primary resistance to EGFR inhibition in GBMs expressing EGFR wild type, a number of studies have provided key insights into mechanisms that mediate secondary resistance to erlotinib in EGFRvIII expressing glioma cells after an initial period of responsiveness. For example, prolonged EGFR inhibition leads to an increased expression of PDGFRβ that mediates a secondary resistance to erlotinib. In another study, it was demonstrated that secondary resistance to erlotinib in GBM is mediated via a dynamic downregulation of EGFRvIII. A comparison of erlotinib sensitivity of lung cancer mutants vs. EGFRvIII suggested that EGFRvIII is resistant to erlotinib because of lower kinase-site occupancy and rapid cycling compared to lung cancer mutants. Another study has identified a Urokinase receptor-Bim signaling axis as mediating EGFR inhibitor resistance.

Accordingly, improved methods and compositions for treating cancer are needed.

SUMMARY OF THE INVENTION

Provided herein are methods for treating cancer, in a patient in need thereof, said method comprising administering to said patient an effective amount of an EGFR inhibitor and one or more additional inhibitors selected from the group consisting of a JNK inhibitor, an ERK inhibitor and an AXL inhibitor.

The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, and necitumumab The JNK inhibitor can selected from the group consisting of: upstream kinase inhibitor CEP-1347, small chemical inhibitors SP600125 and AS601245, peptide inhibitors of the interaction between JNK and its substrates D-JNKI and I-JIP, AEG 3482; BI 78D3; c-JUN peptide; CC 401 dihydrochloride; CEP 1347; IQ 1S; IQ 3; JIP-1 (153-163); SP 600125; SR 3576; SU 3327; TCS JNK 5a; and TCS JNK 6o.

The ERK inhibitor is selected from the group consisting of: U0126, MK-8353, KO-947, AX 15836, BIX 02189, ERK5-IN-1, FR 180204, Pluripotin, TCS ERK 11e, TMCB, XMD 8-92, BVD-523, GDC-099, SCH772984, DEL-22379, VX-11e, ERK5-IN-1, XMD8-92, LY3214996, SC1, Trametinib, Ulixertinib, GDC-0994, pyrazolylpyrrole, pyrimidinylpyrrole, FR148083, FR180204, and FR180289.

The AXL inhibitor is selected from the group consisting of: R428, bemcentinib, YW327.652, GL21.T, TP-0903, LY2801653, amuvatinib, bosutinib, MGCD 265, ASP2215, cabozantinib, foretinib, SGI-7079, MGCD516, ASLAN002, and gilteritinib.

In a particular embodiment, the EGFR inhibitor is erlotinib in combination with one or more of the JNK inhibitor SP600125, the ERK inhibitor U0126, and the AXL inhibitor R428. In other embodiments, the combination is selected from the group of combinations consisting of: erlotinib and SP600125 combination; erlotinib and U0126 combination; erlotinib and R428 combination; erlotinib, SP600125 and U0126 combination; erlotinib, SP600125 and R428 combination; erlotinib, U0126 and R428 combination In one embodiment, the EGFR is either EGFR wild type or contains at least one EGFR activating mutation.

In a further embodiment, the invention method further comprises administering to said patient an effective amount of a TNF inhibitor, such that there are at least 3 inhibitors including an EGFR inhibitor; at least one of a JNK inhibitor, an ERK inhibitor and an AXL inhibitor; and a TNF inhibitor.

The TNF inhibitor is selected from the group consisting of: thalidomide, pomalidomide, lenalidomide, apremilast, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In a particular embodiment, the TNF inhibitor is selected from the group consisting of: thalidomide; prednisone; and etanercept. Thus, in one embodiment, the TNF inhibitor is thalidomide. In another embodiment, the TNF inhibitor is prednisone. In yet another embodiment, the TNF inhibitor is etanercept.

In certain embodiments of the invention methods, the cancer is resistant to EGFR inhibition. In other embodiments, the cancer is a brain cancer selected from the group consisting of: Acoustic Neuroma, Astrocytoma, Pilocytic Astrocytoma, Low-grade Astrocytoma, Anaplastic Astrocytoma, Glioblastoma (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Rhabdoid Tumor. In a particular embodiment, the brain cancer is glioblastoma multiforme (GBM). In certain embodiment for treating brain cancer, each inhibitor is capable of crossing the blood-brain barrier.

In other embodiments of the invention methods, the cancer is selected from the group consisting of: lung cancer, cervical cancer, ovarian cancer, cancer of CNS, skin cancer, prostate cancer, sarcoma, breast cancer, leukemia, colorectal cancer, colon cancer, head and neck cancer, endometrial and kidney cancer, non-small cell lung cancer, human epithelial carcinoma, basal cell carcinoma, squamous cell carcinoma, renal cell carcinoma (RCC), ductal carcinoma in situ (DCIS), and invasive ductal carcinoma.

Also provided herein, are methods of treating a tumor resistant to EGFR inhibition, in a patient in need thereof, comprising administering an agent that inhibits EGFR activity in combination with an agent that inhibits activity of one or more selected from the group consisting of JNK activity, ERK activity and AXL activity. In another embodiment, this particular method can further comprise administering and agent that inhibits TNF activity.

Also provided herein, are pharmaceutical compositions comprising a therapeutically effective amount of an EGFR inhibitor and one or more additional inhibitors selected from the group consisting of a JNK inhibitor, an ERK inhibitor and an AXL inhibitor. The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, and necitumumab. The JNK inhibitor is selected from the group consisting of: upstream kinase inhibitor CEP-1347, small chemical inhibitors SP600125 and AS601245, peptide inhibitors of the interaction between JNK and its substrates D-JNKI and I-JIP, AEG 3482; BI 78D3; c-JUN peptide; CC 401 dihydrochloride; CEP 1347; IQ 1S; IQ 3; JIP-1 (153-163); SP 600125; SR 3576; SU 3327; TCS JNK 5a; and TCS JNK 6o. The ERK inhibitor is selected from the group consisting of: U0126, MK-8353, KO-947, AX 15836, BIX 02189, ERK5-IN-1, FR 180204, Pluripotin, TCS ERK 11e, TMCB, XMD 8-92, BVD-523, GDC-099, SCH772984, DEL-22379, VX-11e, ERK5-IN-1, XMD8-92, LY3214996, SC1, Trametinib, Ulixertinib, GDC-0994, pyrazolylpyrrole, pyrimidinylpyrrole, FR148083, FR180204, and FR180289. The AXL inhibitor is selected from the group consisting of: R428, bemcentinib, YW327.652, GL2I.T, TP-0903, LY2801653, amuvatinib, bosutinib, MGCD 265, ASP2215, cabozantinib, foretinib, SGI-7079, MGCD516, ASLAN002, and gilteritinib.

In a particular embodiment of the invention composition, the EGFR inhibitor is erlotinib in combination with one or more of the INK inhibitor SP600125, the ERK inhibitor U0126, and the AXL inhibitor R428. In other embodiments, the combination is selected from the group of combinations consisting of: erlotinib and SP600125 combination; erlotinib and U0126 combination; erlotinib and R428 combination; erlotinib, SP600125 and U0126 combination; erlotinib, SP600125 and R428 combination; erlotinib, U0126 and R428 combination.

In particular embodiments, the composition further comprises an effective amount of a TNF inhibitor. The TNF inhibitor is selected from the group consisting of: thalidomide, pomalidomide, lenalidomide, apremilast, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In a particular embodiment of the invention composition, the TNF inhibitor is selected from the group consisting of: thalidomide; prednisone; and etanercept. Thus, in one embodiment of the composition, the TNF inhibitor is thalidomide. In another embodiment of the composition, the TNF inhibitor is prednisone. In yet another embodiment of the invention composition, the TNF inhibitor is etanercept.

Aberrant EGFR signaling is widespread in cancer, making the EGFR an important target for therapy. EGFR gene amplification and mutation are common in glioblastoma (GBM), but EGFR inhibition has not been effective in treating this tumor. In accordance with the present invention, it has been found that primary resistance to EGFR inhibition in glioma cells results from a rapid compensatory response to EGFR inhibition that mediates cell survival. In accordance with the present invention, it has been found that in glioma cells expressing either EGFR wild type or the mutant EGFRvIII, EGFR inhibition triggers a rapid adaptive response driven by increased TNF secretion that leads to activation of a TNF-JNK-Axl-ERK signaling axis. Inhibition of this adaptive axis, preferably at one or multiple nodes, renders glioma cells with primary resistance sensitive to EGFR inhibition, and thus to therapeutic treatment with the invention methods and compositions. In accordance with the present invention, the multiple failures of anti-EGFR therapy in GBM is elucidated and a new approach for the treatment of EGFR expressing GBM is provided herein using a combination of EGFR and TNF-JNK-Axl-ERK signaling axis inhibition.

BRIEF DESCRIPTION OF THE DRAWINGS

FIG. 1A-FIG. 1N—EGFR Inhibition Triggers an Adaptive Response in Glioma Cells

FIG. 1A Western blot showing EGFR levels in established GBM cell lines and patient derived primary GBM neurospheres.

FIG. 1B Patient derived primary GBM neurospheres (GBM9) were exposure to erlotinib (1 μM) for the indicated times followed by Western blot with the indicated antibodies.

FIG. 1C-FIG. 1D A similar experiment in patient derived GBM neurospheres from two different patients (GBM39 and SK987).

FIG. 1E U87EGFR cells were treated with erlotinib (1 μM) for the indicated times followed by Western blot with the indicated antibodies.

FIG. 1F Similar experiment was conducted in U87EGFRvIII cells.

FIG. 1G-FIG. 1J Axl was inhibited using R428 (1 μM), a specific inhibitor of Axl. Cells were exposed to Erlotinib followed by Western blot. Erlotinib-induced ERK activation is inhibited when the Axl inhibitor is used in both established GBM cell lines as well as patient derived neurospheres.

FIG. 1K-FIG. 1N siRNA knockdown of Axl results in an inhibition of erlotinib induced ERK activation in both established cell lines as well as patient derived neurospheres. Control siRNA or Axl siRNA was transfected into cells (for 48 h), followed by addition of erlotinib for 48 h and WB with indicated antibodies. Western blots shown in FIG. 1A-FIG. 1N are representative of at least three independent replicates.

FIG. 2C-FIG. 2D U87EGFRwt or U87EGFRvIII cells were exposed to erlotinib for 48 hours in the presence or absence of SP600125 or SB203580 followed by Western blot with the indicated antibodies.

FIG. 2E-FIG. 2F siRNA knockdown for JNK1 and JNK2 was conducted in GBM9 and GBM39 neurospheres followed by exposure to erlotinib for 48 h and Western blot with the indicated antibodies.

FIG. 2G A similar experiment was done in U87EGFRwt cells.

FIG. 2H-FIG. 2K shows that JNK is activated in response to erlotinib in patient derived primary neurospheres as well as established GBM cell lines as determined by the phosphorylation of JNK. Western blots shown in FIG. 2A-FIG. 2K are representative of at least three independent replicates.

FIG. 2L A luciferase reporter assay shows that EGFR inhibition with erlotinib results in an increase in AP-1 transcriptional activity in GBM9 and U87EGFRwt cells. Erlotinib was used for 24 h (1 μM). GBM9: Ctrl vs erlotinib: P=0.0056, t=5.43, d.f.=4 P<0.01; U87EGFRwt: Ctrl vs erlotinib: P=0.0061, t=5.31, d.f.=4. P<0.01. Data are presented as mean±s.e.m. Significant difference analyzed by an unpaired Student's t-test (n=3 biologically independent experimental replicates).

FIG. 3B Ctrl vs erlotinib: P=0.0006, t=9.83, d.f.=4; erlotinib vs erlotinib+SP600125: P=0.0007, t=9.48, d.f.=4.

FIG. 3C Ctrl vs erlotinib: P=0.0011, t=8.39, d.f.=4; erlotinib vs erlotinib+SP600125: P=0.0018, t=7.32, d.f.=4.

FIG. 3D Ctrl vs erlotinib: P=0.0012, t=8.20, d.f.=4; erlotinib vs erlotinib+SP600125: P=0.0022, t=6.97, d.f.=4.

FIG. 3E An ELISA showing the erlotinib (1 μM for 24 h) induced increase in GAS6 levels at a protein level. U87EGFRwt: Ctrl vs erlotinib: P=0.0175, t=3.90, d.f.=4; U87EGFRvIII: Ctrl vs erlotinib: P=0.0030, t=6.45, d.f.=4; GBM9: Ctrl vs erlotinib: P=0.0087, t=4.80, d.f.=4. Data are presented as mean±s.e.m; *P<0.05, P<0.01, *P<0.001 from two-tailed unpaired Student's t-test (n=3 biologically independent experimental replicates).

FIG. 3F Western blot showing increase of GAS6 protein in both GBM9 and U87EGFRwt cells upon erlotinib treatment Western blots shown in a-k are representative of at least three independent replicates.

FIG. 3G A schematic of the GAS6 promoter showing AP-1 sites.

FIG. 3H-FIG. 3I ChIP assay showing the presence of c-Jun on the GAS6 promoter in response to erlotinib (1 μM for 24 h) in GBM9 neurospheres and in U87EGFRwt cells. ChIP results are representative of at least three independent replicates.

FIG. 4A 0 vs 24 h: P=0.0019, t=7.22, d.f.=4. FIG. 4B 0 vs 4 h: P=0.0102, t=4.58, d.f.=4; 0 vs 24 h: P=0.0021, t=7.10, d.f.=4.

FIG. 4C-FIG. 4D A similar experiment was conducted in U87EGFRwt and U87EGFRvIII cells using an erlotinib concentration of 1 μM. FIG. 4C 0 vs 4 h: P=0.0018, t=7.41, d.f.=4; 0 vs 24 h: P=0.0012, t=8.20, d.f.=4. FIG. 4D 0 vs 4 h: P=0.0030, t=6.46, d.f.=4; 0 vs 24 h: P=0.0054, t=5.47, d.f.=4.

FIG. 4E A TNF ELISA was performed on supernatants from erlotinib treated U87EGFRwt and U87EGFRvIII cells (1 μM) and GBM9 and GBM39 neurospheres (100 nM). U87EGFRwt: 0 vs 24 h: P=0.0056, t=5.42, d.f.=4; 0 vs 48 h: P=0.0006, t=10.4, d.f.=4; U87EGFRVIII: 0 vs 24 h: P=0.0022, t=6.98, d.f.=4; 0 vs 48 h: P=0.0083, t=4.86, d.f=4; GBM9: 0 vs 24 h: P=0.01, t=4.6, d.f.=4; 0 vs 48 h: P=0.0043, t=5.84, d.f.=4; GBM39: 0 vs 24 h: P=0.0189, t=3.82, d.f.=4; 0 h vs 48 h: P=0.0024, t=6.81, d.f.=4. Data are presented as mean±s.e.m; *P≤0.05, P≤0.01, *P≤0.001 from two-tailed unpaired Student's t-test (n=3 biologically independent experimental replicates).

FIG. 4F Time course of TNF upregulation in mouse tumors exposed to erlotinib 50 mg/kg for the indicated time points after formation of subcutaneous tumors (n=3). Tumors were removed following erlotinib exposure followed by TNF ELISA on protein extracts. 0 vs 1d: P=0.0045, t=5.77, d.f.=4; 0 vs 2d: P=0.0002, t=13.92, d.f.=4; 0 vs 7d: P=0.0245, t=3.52, d.f=4. Data are presented as mean±s.e.m; * P<0.05, P<0.01, *P<0.001 from a two-tailed unpaired Student's t-test.

FIG. 4G Shows signal transduction in tumors exposed to erlotinib (50 mg/kg) for the indicated time points.

FIG. 4H A neutralizing antibody to TNF (1 μg/ml) blocked erlotinib induced activation of Axl, ERK and JNK in GBM9 and GBM39 neurospheres and U87EGFRwt and U87EGFRvIII cell lines, while a control antibody had no effect.

FIG. 4I siRNA knockdown of TNFR1 blocked erlotinib induced activation of Axl, ERK and JNK in GBM9 and GBM39 neurospheres and also U87EGFRwt and U87EGFRvIII cell lines, while control (scrambled siRNA) had no effect. Western blots shown in FIG. 4G-FIG. 4I are representative of at least three independent replicates.

FIG. 5A-FIG. 5N—Inhibition of JNK and ERK Renders Glioma Cells Sensitive to EGFR Inhibition FIG. 5A AlamarBlue assay in established GBM cell lines exposed to erlotinib (10 μM). Cells are completely resistant to the effects of EGFR inhibition.

FIG. 5B-FIG. 5C Patient derived GBM9 or GBM39 neurospheres were exposed to erlotinib (100 nM) with or without JNK inhibitor SP600125 (1 μM), p38 inhibitor SB203580 (10 μM), or ERK inhibitor U0126 (1 μM), followed by Alamarblue Cell Survival Assay after 72 h of inhibitor exposure. FIG. 5B Erlotinib vs erlotinib+SP600125: P=0.0015, t=7.75, d.f=4; erlotinib vs erlotinib+U0126: P=0.0013, t=8.10, d.f=4. FIG. 5C erlotinib vs erlotinib+SP600125: P=0.0057, t=5.41, d.f.=4; Erlotinib vs Erlotinib+U0126: P=0.0023, t=6.93, d.f.=4.

FIG. 5D-FIG. 5E A similar experiment was conducted in U87EGFRwt and U87EGFRvIII cells. FIG. 5D erlotinib vs erlotinib+SP600125: P=0.0016, t=7.61, d.f=4; Erlotinib vs Erlotinib+U0126: P=0.0017, t=7.48, d.f.=4. FIG. 5E erlotinib vs erlotinib+SP600125: P=0.0003, t=12.23, d.f=4; erlotinib vs erlotinib+U0126: P=0.0014, t=7.87, d.f.=4.

FIG. 5F siRNA knockdown of JNK1 and JNK2 in GBM9 neurospheres results in an enhanced sensitivity to erlotinib, whereas control siRNA has no effect. Erlotinib+siCtrl vs erlotinib+siJNK1/2: P=0.0002, t=13.96, d.f.=4.

FIG. 5G siRNA knockdown of JNK1 and JNK2 in GBM39 neurosphere cells has a similar effect. Erlotinib+siCtrl vs Erlotinib+siJNK1/2: P=0.0003, t=11.86, d.f.=4.

FIG. 5H U87EGFRwt cells results in an enhanced sensitivity to erlotinib, whereas control siRNA has no effect. Erlotinib+siCtrl vs erlotinib+siJNK1/2: P=0.0017, t=7.52, d.f.=4.

FIG. 5I-FIG. 5J Patient derived GBM9 or GBM39 neurospheres were exposed to erlotinib (100 nM) with or without Axl inhibitor R428 (1 μM) followed by Alamarblue Cell Survival Assay after 72 h. FIG. 5I Erlotinib vs erlotinib+R428: P=0.0025, t=6.75, d.f.=4. FIG. 5I Erlotinib vs erlotinib+R428: P=0.0023, t=6.93, df=4.

FIG. 5K A similar experiment was done in U87EGFRwt cells using an erlotinib concentration of 104. Erlotinib vs erlotinib+R428: P=0.0094, t=4.69, d.f.=4.

FIG. 5L-FIG. 5N siRNA knockdown of Axl in GBM9 and GBM39 neurospheres or U87EGFRwt cells sensitizes cells to the effect of erlotinib but not control siRNA as determined by Alamarblue Cell Viability Assay. FIG. 5L Erlotinib+ siCtrl vs erlotinib+siAxl: P=0.0004, t=11.23, d.f.=4. FIG. 5M Erlotinib+siCtrl vs erlotinib+siAxl: P=0.0003, t=12.80, d.f.=4. FIG. 5N Erlotinib+siCtrl vs erlotinib+R428: P=0.0058, t=5.38, d.f.=4. Data are presented as mean±s.e.m; P<0.01, *P<0.001 from two-tailed unpaired Student's t-test (n=3 biologically independent experimental replicates).

FIG. 6A-FIG. 6N—TNF Inhibition Sensitizes Glioma Cells to EGFR Inhibition FIG. 6A-FIG. 6B AlamarBlue cell viability assay in GBM9 or GBM39 neurospheres. Enbrel (100 nM) sensitizes cells to EGFR inhibition with erlotinib. Enbrel and erlotinib were added to GBM9 or GBM39 neurospheres concurrently and AlamarBlue assay was done after 72 h. FIG. 6A Erlotinib vs Erlotinib+Enbrel: P=0.0027, t=6.59, d.f.=4. FIG. 6B Erlotinib vs erlotinib+enbrel: P=0.0044, t=6.59, d.f=4.

FIG. 6C A similar experiment was performed in U87EGFRwt cells. Erlotinib vs Erlotinib+Enbrel: P=0.0056, t=5.41, d.f.=4.

FIG. 6D-FIG. 6 ETNFR1 was silenced using siRNA in GBM9 and GBM39 cells and cells were exposed to erlotinib for 72 h in stem cell medium without EGF for 72 h followed by Alamarblue Assay. FIG. 6D Erlotinib+siCtrl vs erlotinib+siTNFR1: P=0.0014, t=7.95, d.f.=4.

FIG. 6E Erlotinib+siCtrl vs erlotinib+siTNFR1: P=0.0041, t=5.90, d.f.=4.

FIG. 6F A similar experiment was done in U87EGFRwt cells. Erlotinib+siCtrl vs erlotinib+siTNFR1: P=0.0021, t=7.11, d.f=4.

FIG. 6G-FIG. 6I Thalidomide sensitizes GBM9 and GBM39 cells to EGFR inhibition with erlotinib. Thalidomide (1 μM) and erlotinib were added to GBM9 and GBM39 neurospheres (100 nM) or U87EGFRwt cells (1 uM) concurrently and AlamarBlue assay was done after 72 h. FIG. 6G Erlotinib vs erlotinib+thalidomide: P=0.0030, t=6.42, d.f.=4. FIG. 6H Erlotinib vs erlotinib+thalidomide: P=0.0027, t=6.59, d.f.=4. FIG. 6I Erlotinib vs erlotinib+thalidomide: P=0.0013, t=8.11, d.f.=4.

FIG. 6J-FIG. 6K Enbrel or thalidomide block erlotinib induced activation of JNK, Axl and ERK in GBM9 and GBM39 neurospheres as shown in the Western blot.

FIG. 6L A similar experiment was conducted in U87EGFRwt cells. Western blots shown in FIG. 6J-FIG. 6L are representative of at least three independent replicates.

FIG. 6M-FIG. 6N show that exogenous TNF protects GBM9 and GBM39 neurospheres from erlotinib induced cell death. TNF (ing/nil) and erlotinib (1 μM) were added to cells concurrently and AlamarBlue cell viability assay was done after 72 h. FIG. 6M Erlotinib vs erlotinib+TNF: P=0.0018, t=7.41, d.f.=4. FIG. 6N Erlotinib vs erlotinib+TNF: P=0.0087, t=4.79, d.f.=4. Data are presented as mean±s.e.m; P<0.01, *P<0.001 from two-tailed unpaired Student's t-test (n=3 biologically independent experimental replicates).

FIG. 7B Treatment of subcutaneous tumors with a combination of erlotinib and thalidomide. The tumor growth did not decrease in mice treated erlotinib (50 mg/kg) or thalidomide (150 mg/kg) alone, whereas the combination of erlotinib and thalidomide was found to decrease tumor growth significantly. Unpaired t-test, Erlotinib vs erlotinib+thalidomide: ****P<0.0001, t=6.1, d.f.=14.

FIG. 7C Combined treatment of erlotinib and thalidomide prolonged survival and suppressed tumor growth in an orthotopic model. Kaplan-Maier survival curves were calculated using GraphPad Prism 7. Statistical significance verified by the log rank test, P=0.0008, ***P<0.001.

FIG. 7D Representative bioluminescence images from erlotinib and erlotinib plus thalidomide group at day 1, 10 and 20 post-treatment. Since all the mice in vehicle and thalidomide group died within 20 days after transplant, images at day 20 post-treatment were not available.

FIG. 7E Time course of TNF upregulation in mouse tumors exposed to erlotinib 50 mg/kg for the indicated time points (n=3). Tumors were removed following erlotinib exposure followed by TNF ELISA on protein extracts. 0 vs 1d: P=0.0091, t=4.73, d.f.=4; 0 vs 2d: P=0.0005, t=10.36, d.f.=4; 0 vs 7d: P=0.0181, t=3.86, d.f.=4. Data are presented as mean±s.e.m; *P<0.05, P<0.01, *P<0.001 from a two-tailed unpaired Student's t-test.

FIG. 7F Shows signal transduction in intracranial tumors exposed to erlotinib (50 mg/kg) for the indicated time points.

FIG. 7G Western blots of intracranial tumor lysates obtained from erltinib and/or thalidomide treated mice. The animals without treatment were considered as Ctrl (control, 0-day treatment). Western blots shown in FIG. 7F and FIG. 7G are representative of three independent replicates.

FIG. 8 A-FIG. 8J—EGFR Inhibition Activates Signaling Pathways

FIG. 8A-FIG. 8B EGFR inhibition activates signaling pathways FIG. 8A U251EGFR cells were treated with erlotinib (1 μM) for the indicated times followed by Western blot with the indicated antibodies. FIG. 8B GBM9 neurospheres were treated with afatinib (100 nM) for the indicated time points followed by Western blot with the indicated antibodies. Western blots are representative of at least three independent replicates.

FIG. 8C-FIG. 8G EGFR inhibition decreases pSTAT3 and pAKT activation. Glioma cells were treated with high dosage of erlotinib (10 μM) or afatinib (10 μM). Western blot showing that pSTAT3 and pAKT decrease upon treatment with erlotinib or afatinib. Western blots are representative of at least three independent replicates.

FIG. 8H-FIG. 8J pERK is activated in U87EGFRwt and blocked by cetuximab. FIG. 8H U87EGFRwt cells were cultured in medium with (10%) or without serum in DMEM. pERK is activated under both conditions. FIG. 8I Cells were serum starved and treated overnight with cetuximab (100 μg/ml). Cetuximab treatment blocks both EGFR and ERK activation. FIG. 8J Cells were treated with EGF (50 ng/ml) for 15 min. EGF increases pERK level in U87EGFRwt cells. SF: Serum free. Western blots are representative of at least three independent replicates.

FIG. 9A A luciferase reporter assay shows that EGFR inhibition with erlotinib does not result in an increase in NF-κB reporter activity in GBM9 neurospheres and U87EGFRwt cells. Erlotinib was used for 24 h at a concentration of 100 nM for GBM9 neurospheres and 1 uM for U87EGFRwt cells. GBM9: Ctrl vs erlotinib: P=0.88, t=0.16, d.f.=4; U87EGFRwt: Ctrl vs erlotinib: P=0.60, t=0.57, d.f.=4. FIG. 9B As a positive control we used LPS (1 μg/ml) which activates the NF-κB reporter. Renilla luciferase was used as an internal control. Ctrl vs LPS: P=0.0012, t=8.27, d.f.=4. Data are presented as mean±s.e.m; **P<0.01 from two-tailed unpaired Student's t-test (n=3 biologically independent experimental replicates). n.s. not significant.

FIG. 9C-FIG. 9D Upregulation of TNF in response to EGFR inhibition in multiple patient derived samples and established cell lines. FIG. 9C SK987, SK748. SK1422, and GBM622 are patient derived primary GBM cells cultured as neurospheres and treated with erlotinib (100 nM) for 24 h followed by extraction of RNA and qRT-PCR for TNF. SB19vIII and U251EGFRwt cells are established GBM cell lines that were treated with erlotinib (1 μM) for 24 h followed by qRT-PCR for TNF. SB19vIII: Ctrl vs Erlotinib: P=0.0014, t=7.88, d.f.=4; SK987: Ctrl vs erlotinib: P=0.0024, t=6.83, d.f.=4; SK748: Ctrl vs Erlotinib: P=0.0019, t=7.32, d.f.=4; SK1422: Ctrl vs erlotinib: P=0.0030, t=6.45, d.f.=4; GBM622: Ctrl vs erlotinib: P=0.21, t=1.5, df=4; U251EGFRwt: Ctrl vs erlotinib: P=0.0005, t=10.4, d.f.=4. Data are presented as mean±s.e.m; P<0.01, *P<0.001 from two-tailed unpaired Student's t-test (n=3 biologically independent experimental replicates). n.s. not significant. FIG. 9D Western blot showing EGFR levels in various neurospheres and cell lines. No increase in TNF is detected in GBM622 cells expressing a very low level of EGFR. Western blots are representative of at least three independent replicates.

FIG. 9E Downregulation of TNFR1 in response to EGFR inhibition in patient derived primary GBM neurosphere cultures and established cell lines. GBM9, SK987 and U87EGFRwt cells were treated with erlotinib for the indicated time points followed by Western blot with TNFR1 antibodies. Erlotinib was used at a concentration of 100 nM for GBM9 and SK987 and 1 uM for U87EGFRwt cells. Western blots are representative of at least three independent replicates.

FIG. 9F EGFR inhibition induced effects on cell viability are influenced by specific inhibitors of downstream signaling pathways. In this experiment primary GBM9 neurospheres were exposed to various inhibitors alone or in combination with erlotinib (1 μM) for 72 h followed by Alamarblue Cell Viability assay. The concentrations of the various drugs were: SB203850 (10 uM), SP600125 (1 uM), U0126 (1 uM), BMS-345541 (10 uM), XL765 (10 uM), Necrostatin-1 (300 nM). Erlotinib vs erlotinib+SP600125: P=0.0001, t=14.96, d.f.=4; Erlotinib vs erlotinib+U0126: P=0.0018, t=7.42, d.f.=4. Data are presented as mean±s.e.m; P<0.01, *P<0.001 from two-tailed unpaired Student's t-test (n=3 biologically independent experimental replicates).

FIG. 9G-FIG. 9I Western blot showing efficient silencing of JNK1/2, Axl and TNFR1. For cell viability experiments involving siRNA knockdown of JNK1/2, Axl and TNFR1, we confirmed silencing by Western blot. Western blots are representative of at least three independent replicates.

FIG. 10A Erlotinib vs erlotinib+thalidomide: P=0.0015, t=7.77, d.f=4. FIG. 10B Erlotinib vs erlotinib+thalidomide: P=0.0008, t=8.98, d.f=4. Data are presented as mean±s.e.m; P<0.01, *P<0.001 from two-tailed unpaired Student's t-test (n=3 biologically independent experimental replicates).

FIG. 10C-FIG. 10D A neutralizing antibody to TNF sensitizes cells to EGFR inhibition. Patient derived GBM9 neurospheres or established GBM cell line U87EGFRwt cells were exposed to erlotinib plus either control antibody or a neutralizing antibody to TNF. The TNF neutralizing antibody sensitizes cells to EGFR inhibition as shown by the Alamarblue Cell Viability assay. FIG. 10C Erlotinib vs erlotinib+TNF Ab: P=0.0013, t=8.07, d.f.=4. FIG. 10D Erlotinib vs erlotinib+TNF Ab: P=0.0012, t=8.13, d.f.=4. Data are presented as mean±s.e.m; **P<0.01 from two-tailed unpaired Student's t-test (n=3 biologically independent experimental replicates).

FIG. 10E-FIG. 10F Thalidomide sensitizes patient derived primary GBM9 and GBM39 neurospheres to EGFR inhibitor. GBM9 or GBM39 neurospheres were exposed to EGFR inhibition using afatinib (100 nM) and thalidomide (1 μM) alone or in combination concurrently for 72 h followed by Alamarblue Cell Viability Assay. FIG. 10E Afatinib vs afatinib+thalidomide: P=0.0001, t=14.47, d.f.=4. (f) Afatinib vs afatinib+thalidomide: P=0.0005, t=10.4, d.f.=4. Data are presented as mean±s.e.m; ***P<0.001 from two-tailed unpaired Student's t-test (n=3 biologically independent experimental replicates).

FIG. 11B Unstained: Erlotinib vs Erlotinib+SP600125: P=0.0008, t=9.10, d.f.=4; Erlotinib vs erlotinib+U0126: P=0.0036, t=6.14, d.f.=4. Annexin+PI: Erlotinib vs erlotinib+SP600125: P=0.0003, t=11.37, d.f=4; Erlotinib vs erlotinib+U0126: P=0.0021, t=7.04, d.f.=4.

FIG. 11C-FIG. 11D A similar experiment was conducted in U87EGFR cells with a similar result. FIG. 11D Unstained: Erlotinib vs erlotinib+SP600125: P=0.0045, t=5.77, d.f.=4; Erlotinib vs erlotinib+U0126: P=0.0013, t=8.06, d.f.=4. Annexin+PI: Erlotinib vs erlotinib+SP600125: P=0.0017, t=7.53, d.f.=4; Erlotinib vs erlotinib+U0126: P=0.0006, t=10.04, d.f.=4. Data are presented as mean±s.e.m; P<0.01, *P<0.001 using two-tailed unpaired Student's t-test (n=3 biologically independent experimental replicates).

FIG. 12B Unstained: Erlotinib vs erlotinib+R428: P=0.0051, t=5.58, d.f.=4; Erlotinib vs erlotinib+thalidomide: P=0.0009, t=8.75, d.f.=4. Annexin+PI: Erlotinib vs erlotinib+R428: P=0.015, t=4.10, d.f=4; Erlotinib vs erlotinib+thalidomide: P=0.0011, t=8.32, d.f.=4.

FIG. 12C-FIG. 12D A similar experiment was conducted in U87EGFR cells with a similar result. FIG. 12D

Unstained: Erlotinib vs erlotinib+R428: P=0.0045, t=5.71, d.f=4; Erlotinib vs erlotinib+thalidomide: P=0.0036, t=6.13, d.f.=4. Annexin+PI: Erlotinib vs erlotinib+R428: P=0.0014, t=7.83, d.f.=4; Erlotinib vs erlotinib+thalidomide: P=0.0022, t=6.98, d.f.=4. Data are presented as mean±s.e.m; *P<0.05, P<0.01, *P<0.001 using two-tailed unpaired Student's t-test (n=3 biologically independent experimental replicates).

Figure 13A:
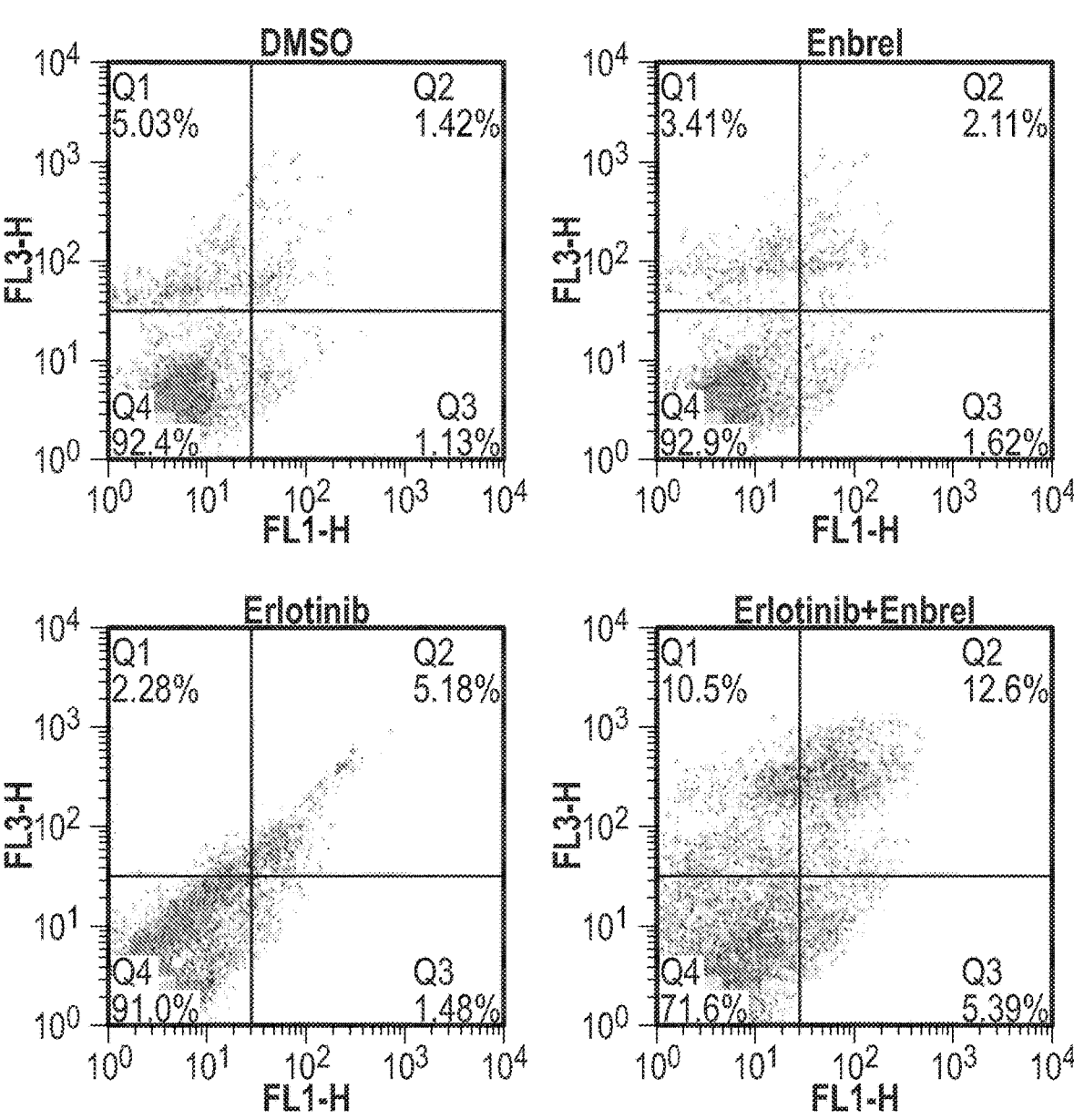
Figure 13B:
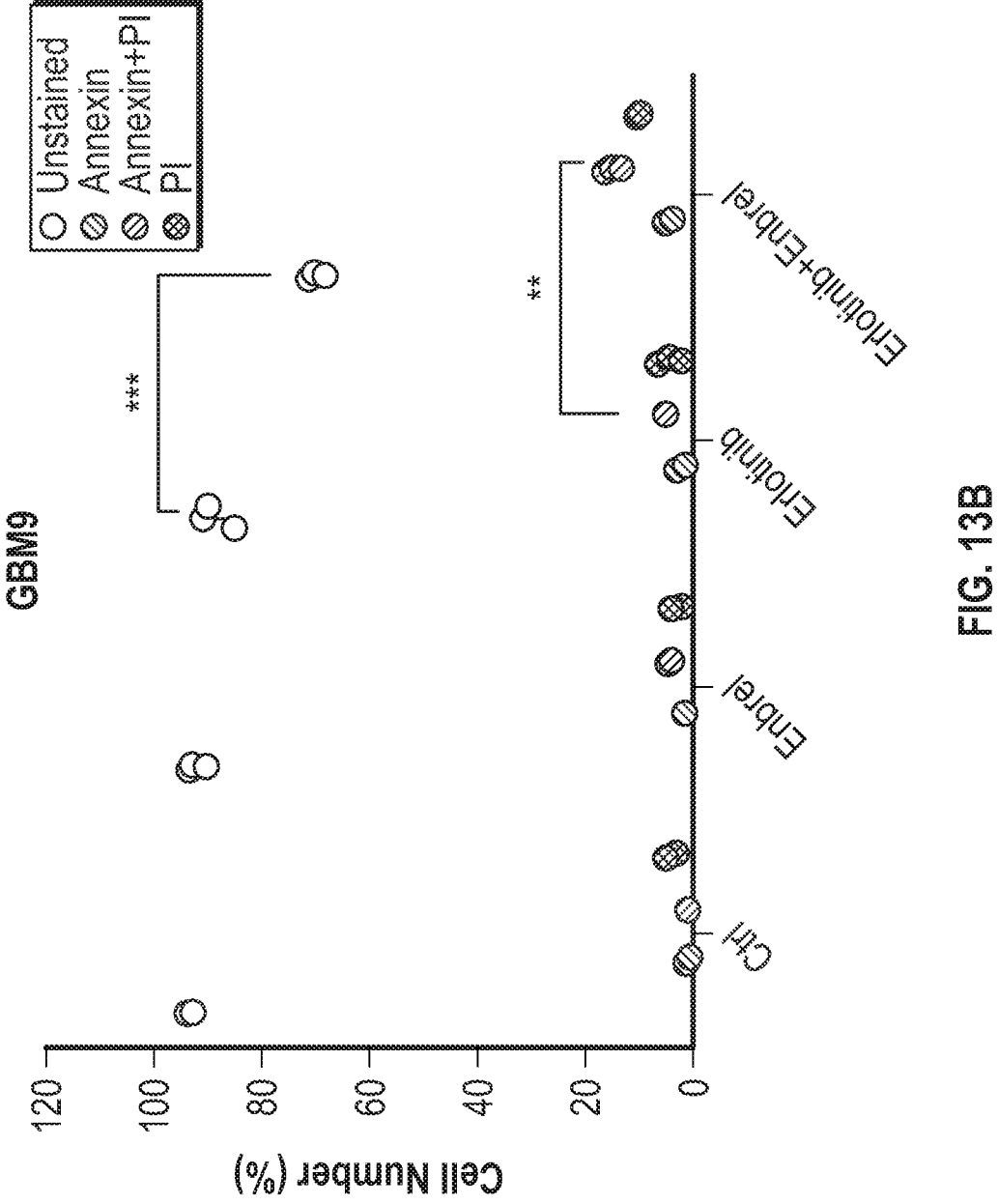

FIG. 13A-FIG. 13D—Etanercept Renders Glioma Cells Sensitive to EGFR Inhibition FIG. 13A-FIG. 13B GBM9 cells were treated with erlotinib and/or enbrel (1 μM) for 72 hours followed by Annexin-FACS assay. Unstained cells represent viable cells. Annexin positive cells are undergoing apoptosis. PI (Propidium iodide) positive cells are undergoing late apoptosis. In "Control" cells are treated with control vehicle (DMSO). The combination treatment decreases the number of viable cells and there is an increase in double stained cells (Annexin+PI Positive). FIG. 13B Unstained: Erlotinib vs erlotinib+Enbrel: P=0.0008, t=9.11, d.f=4; Annexin+PI: Erlotinib vs erlotinib+Enbrel: P=0.0012, t=8.18, d.f.=4.

Figure 13C:
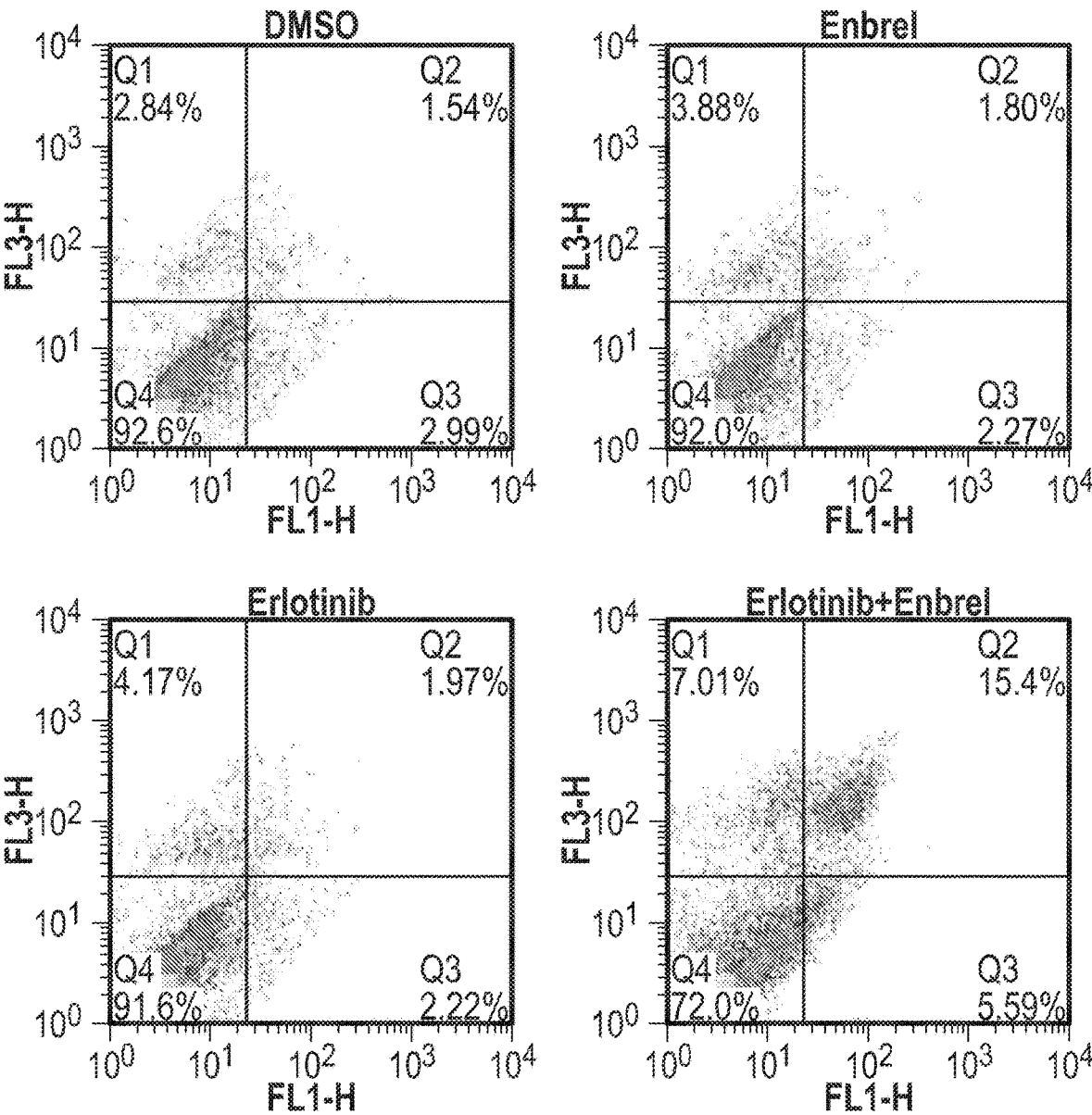
Figure 13D:
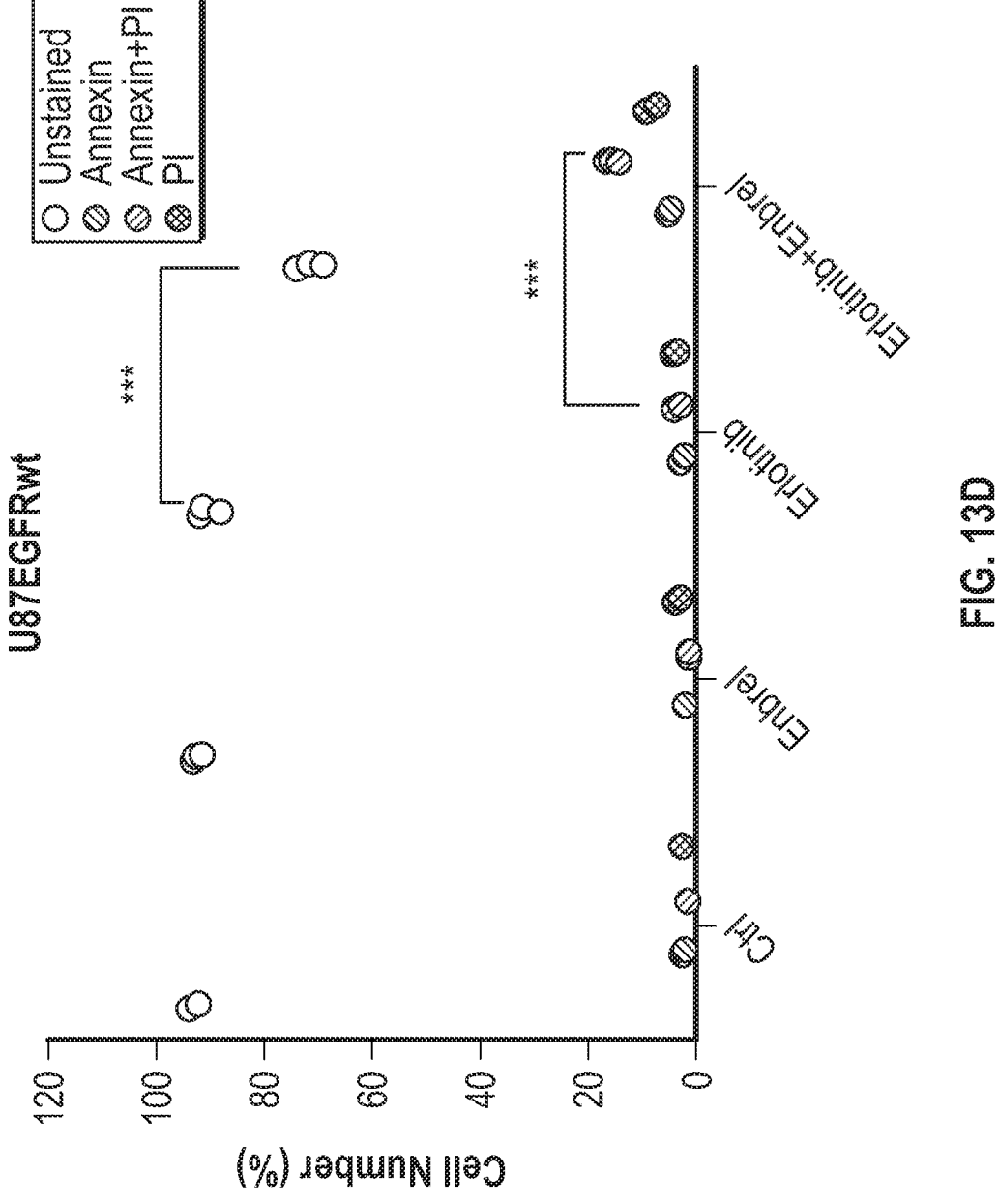

FIG. 13C-FIG. 13D A similar experiment was conducted in U87EGFRwt cells with a similar result. FIG. 13D Unstained: Erlotinib vs erlotinib+Enbrel: P=0.0006, t=9.6, d.f.=4; Annexin+PI: Erlotinib vs erlotinib+Enbrel: P=0.0003, t=11.34, d.f.=4. Data are presented as mean±s.e.m; P<0.01, *P<0.001 using two-tailed unpaired Student's t-test (n=3 biologically independent experimental replicates).

Figures 14A, 14B, 14C, 14D, 14E, 14F:
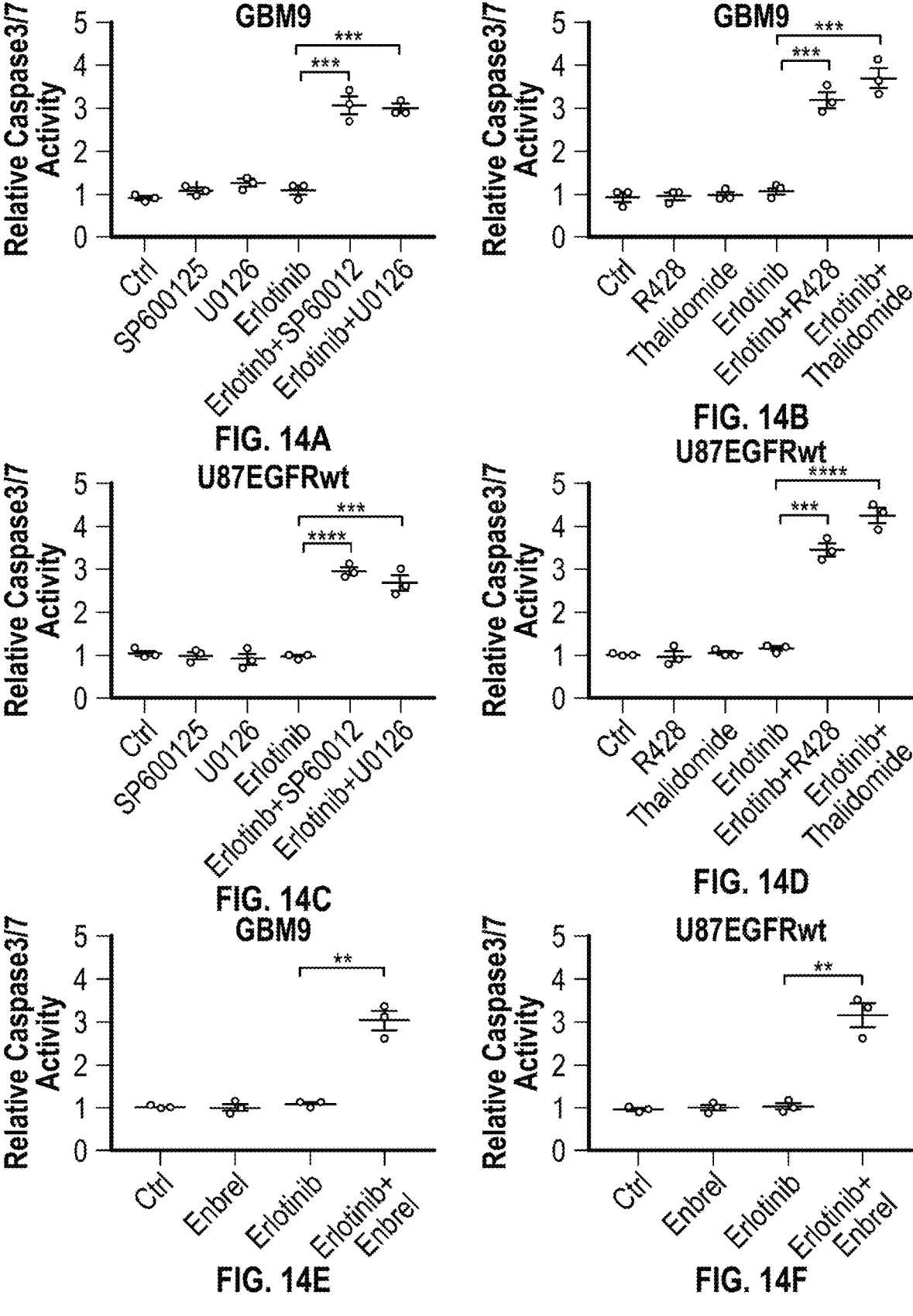

FIG. 14A-FIG. 14F—Combination Treatment Increases Caspase3/7 Activity in Glioma Cells FIG. 14A GBM9 cells were treated by erlotinib and/or SP600125, U1026 for 72 hours followed by Caspase-Glo 3/7 Assay. Caspase3/7 activity was evaluated in GBM9 cells exposed to erlotinib plus SP600125. Similar results were obtained using a combination of erlotinib and U1026. Erlotinib vs erlotinib+SP600125: P=0.001, t=8.66, d.f.=4; Erlotinib vs erlotinib+U0126: P=0.0002, t=13.24, d.f=4. Similar procedures were performed in FIG. 14B-FIG. 14F and similar results were obtained.

FIG. 14B Erlotinib vs erlotinib+R428: P=0.0004, t=10.76, d.f.=4; Erlotinib vs erlotinib+thalidomide: P=0.0004, t=10.64, d.f.=4.

FIG. 14C Erlotinib vs erlotinib+SP600125: P<0.0001, t=21.41, d.f.=4; Erlotinib vs erlotinib+U1026: P=0.0007, t=9.49, d.f.=4.

FIG. 14D Erlotinib vs erlotinib+R428: P=0.0001, t=14.8, d.f.=4; Erlotinib vs erlotinib+T: P<0.0001, t=16.77, d.f.=4.

FIG. 14E Erlotinib vs erlotinib+enbrel: P=0.0096, t=8.72, d.f.=4.

FIG. 14F Erlotinib vs erlotinib+enbrel: P=0.0017, t=7.43, d.f.=4. Data are presented as mean±s.e.m; P<0.01, *P<0.001, ****P<0.0001 from two-tailed unpaired Student's t-test (n=3 biologically independent experimental replicates).

Figures 15A, 15B, 15C, 15D, 15E, 15F:
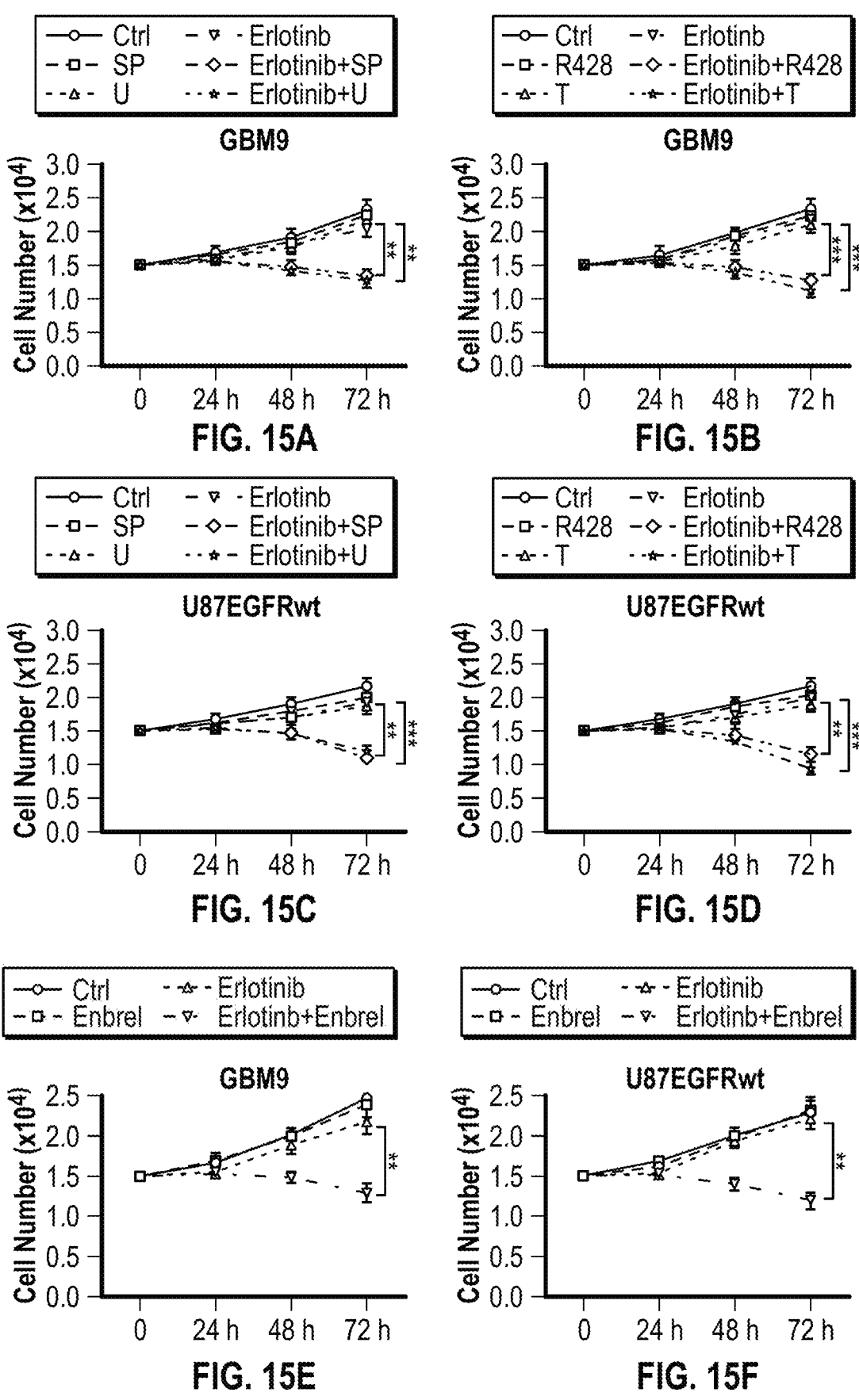

FIG. 15A-FIG. 15F—Combination Treatment Inhibits Glioma Cell Proliferation FIG. 15A GBM9 cells were plated in 6 well plated and treated with drugs as indicated. Cell proliferation was measured through cell counting using the trypan blue dye exclusion test. A combination of erlotinib and SP600125 (SP) significantly reduces cell growth after 72 hours. Similar results were shown using a combination of erlotinib and U1026 (U). Erlotinib vs erlotinib+SP: P=0.0016, t=7.60, d.f.=4; Erlotinib vs erlotinib+U: P=0.0012, t=8.24, d.f.=4. Similar procedures were performed in FIG. 15B-FIG. 15F and similar results were obtained.

FIG. 15B Erlotinib vs erlotinib+R428: P=0.0008, t=9.24, d.f.=4; Erlotinib vs erlotinib+T: P=0.0004, t=11.18, d.f.=4.

FIG. 15C Erlotinib vs erlotinib+SP: P=0.0004, t=10.78, d.f.=4; Erlotinib vs erlotinib+U: P=0.0014, t=7.85, d.f=4.

FIG. 15D Erlotinib vs erlotinib+R428: P=0.001, t=8.62, d.f.=4; Erlotinib vs erlotinib+T: P=0.0003, t=11.58, d.f=4.

FIG. 15E Erlotinib vs erlotinib+enbrel: P=0.0014, t=7.85, d.f.=4.

FIG. 15F Erlotinib vs erlotinib+enbrel: P=0.0005, t=10.37, d.f.=4. SP: SP600125; U:U0126; T: Thalidomide. Data are presented as mean±s.e.m; P<0.01, *P<0.001 from two-tailed unpaired Student's t-test (n=3 biologically independent experimental replicates).

Figures 16A, 16B, 16C, 16D, 16E, 16F:
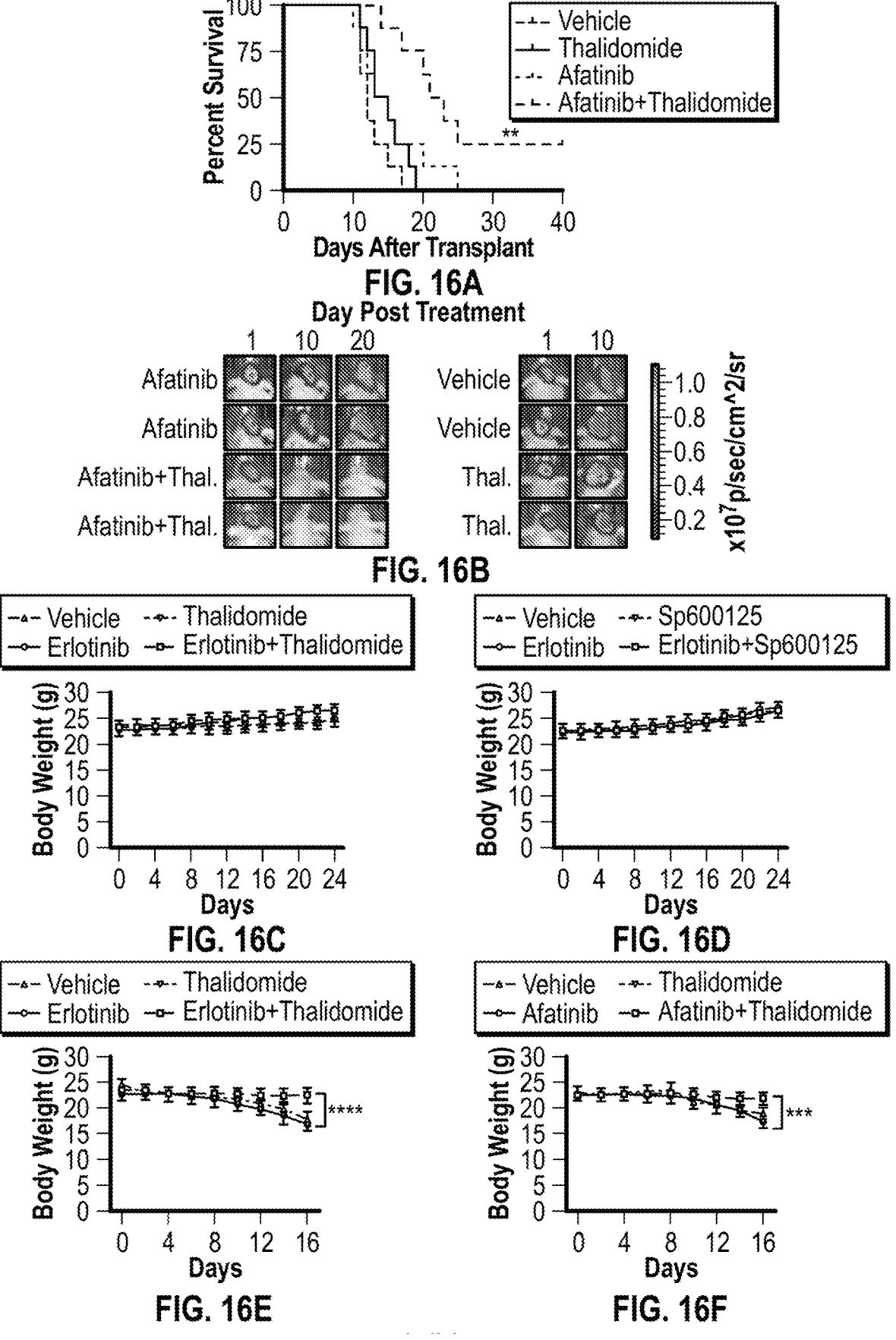

FIG. 16A-FIG. 16F—TNF Inhibition Sensitizes Mouse Tumors to EGFR Inhibition with Afatinib In Vivo FIG. 16A Combined treatment of afatinib and thalidomide prolonged survival and suppressed tumor growth in an orthotropic model. Kaplan-Maier survival curves were calculated using GraphPad Prism 7. Statistical significance verified by the log rank test, P=0.0015,**P<0.01.

FIG. 16B Representative bioluminescence images from afatinib and afatinib plus thalidomide group at day 1, 10 and 20 post-treatment. Since all mice in vehicle and thalidomide group died within 20 days after transplant, images at day 20 post-treatment were not available.

FIG. 16C-FIG. 16D Body weight of xenograft mice were monitored regularly and recorded every 2 days. No significant change of body weight was observed in subcutaneous mouse model between groups.

FIG. 16E Body weight of orthotopic models. Body weight losses are found in vehicle, erlotinib and thalidomide group but not in combination therapy (erlotinib+thalidomide). Erlotinib vs erlotinib+thalidmoide: P<0.0001, t=6.32, d.f.=14;

FIG. 16F Similar results were obtained in orthotopic models treated by afatinib and/or thalidmide. Afatinib vs afatinib+thalidomide: P=0.0003, t=4.79, d.f.=14.

Figures 17A, 17B, 17C, 17D:
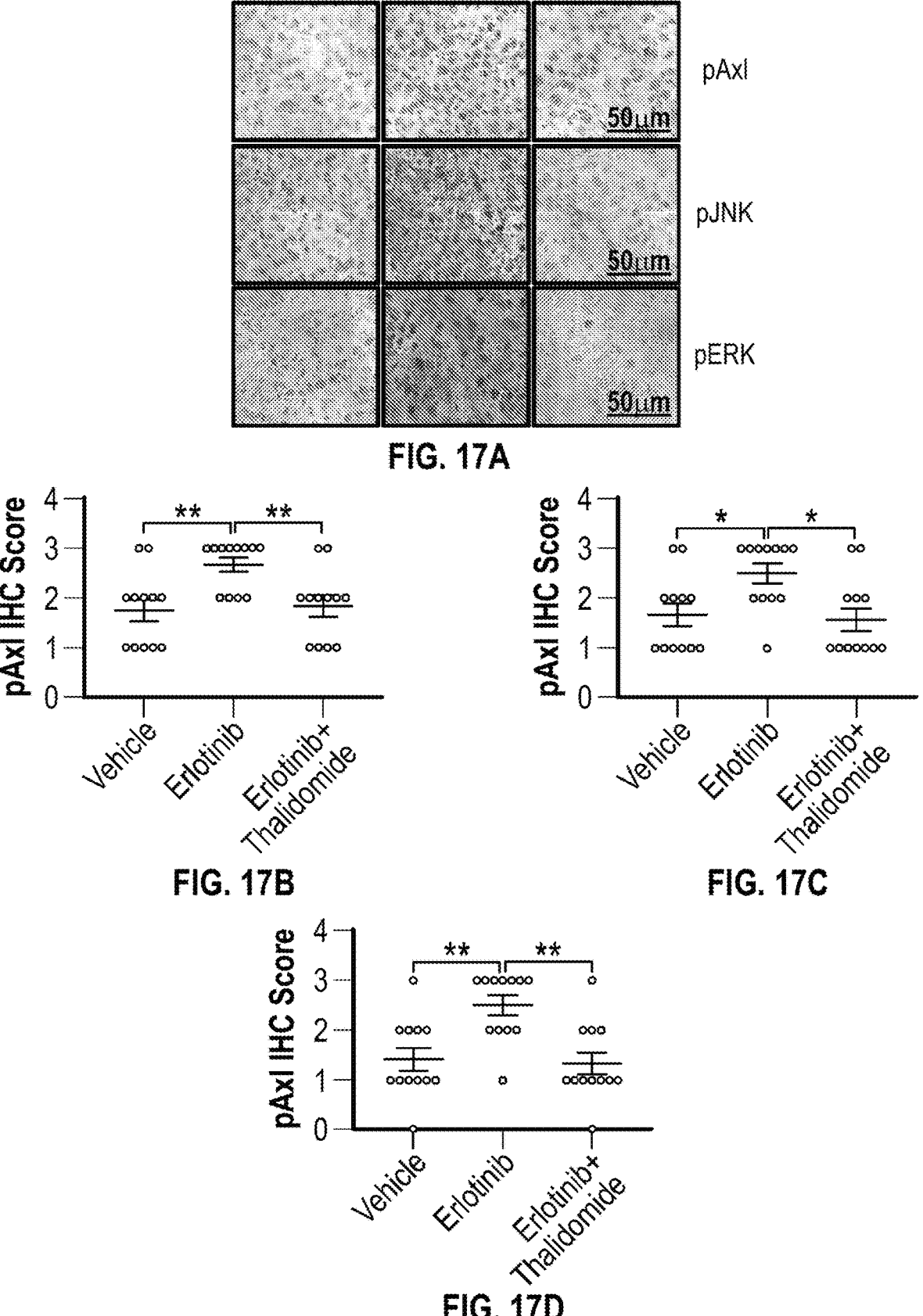

FIG. 17A-FIG. 17D—Erlotinib Treatment Activates pAxl-pJNK-pERK Signaling in Orthotopic Models which was Suppressed by TNF Inhibition FIG. 17A Immunostainig of pAXL, pJNK and pERK proteins from a representative brain section from vehicle, erlotinb and erlotinib plus thalidomide group. Cells with brown staining are considered as positive. Erlotinib group shows higher expression of pAxl, pJNK and pERK compared to vehicle group, whereas thaldimide inhibits erlotinib induced pAxl-pJNK-pERK activation.

FIG. 17B-FIG. 17D Semi-quantitative analysis of pAxl, pJNK and pERK immunostaining. Four random fields in 3 tissue blocks at ×200 magnification were scored semiquantitatively as: 0=No positive staining; 1=1-25% tumor cells stained, 2=26%-75% tumor cells stained and 3=>75% tumor cells stained. Differences between treatment groups were analyzed by the Mann-Whitney U test (n=12). FIG. 17B pAXL: Erlotinib vs. vehicle, p=0.0062, U=26; Erlotinib vs. erlotinib+thalidomide, p=0.0093, U=28. FIG. 17C pJNK: Erlotinib vs. vehicle, p=0.022, U=32; Erlotinib vs. erlotinib+thalidomide, p=0.014, U=29.5. FIG. 17D pERK: Erlotinib vs. vehicle, p=0.0040, U=23.5; Erlotinib vs. erlotinib+thalidomide, p=0.0026, U=21.

DETAILED DESCRIPTION

Provided herein are methods for treating cancer, in a patient in need thereof, said method comprising administering to said patient an effective amount of an EGFR inhibitor and one or more additional inhibitors selected from the group consisting of a INK inhibitor, an ERK inhibitor and an AXL inhibitor.

The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, and necitumumab The INK inhibitor can selected from the group consisting of: upstream kinase inhibitor CEP-1347, small chemical inhibitors SP600125 and AS601245, peptide inhibitors of the interaction between JNK and its substrates D-JNKI and I-JIP, AEG 3482; BI 78D3; c-JUN peptide; CC 401 dihydrochloride; CEP 1347; IQ 1S; IQ 3; JIP-1 (153-163); SP 600125; SR 3576; SU 3327; TCS INK 5a; and TCS INK 6o.

The ERK inhibitor is selected from the group consisting of: U0126, MK-8353, KO-947, AX 15836, BIX 02189, ERK5-IN-1, FR 180204, Pluripotin, TCS ERK 11e, TMCB, XMD 8-92, BVD-523, GDC-099, SCH772984, DEL-22379, VX-11e, ERK5-IN-1, XMD8-92, LY3214996, SC1, Trametinib, Ulixertinib, GDC-0994, pyrazolylpyrrole, pyrimidinylpyrrole, FR148083, FR180204, and FR180289.

The AXL inhibitor is selected from the group consisting of: R428, bemcentinib, YW327.6S2, GL2I.T, TP-0903, LY2801653, amuvatinib, bosutinib, MGCD 265, ASP2215, cabozantinib, foretinib, SGI-7079, MGCD516, ASLAN002, and gilteritinib.

In a particular embodiment, the EGFR inhibitor is erlotinib in combination with one or more of the JNK inhibitor SP600125, the ERK inhibitor U0126, and the AXL inhibitor R428. In other embodiments, the combination is selected from the group of combinations consisting of: erlotinib and SP600125 combination; erlotinib and U0126 combination; erlotinib and R428 combination; erlotinib, SP600125 and U0126 combination; erlotinib, SP600125 and R428 combination; erlotinib, U0126 and R428 combination In one embodiment, the EGFR is either EGFR wild type or contains at least one EGFR activating mutation.

In a further embodiment, the invention method further comprises administering to said patient an effective amount of a TNF inhibitor, such that there are at least 3 inhibitors including an EGFR inhibitor; at least one of a INK inhibitor, an ERK inhibitor and an AXL inhibitor; and a TNF inhibitor.

The TNF inhibitor is selected from the group consisting of: thalidomide, pomalidomide, lenalidomide, apremilast, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In a particular embodiment, the TNF inhibitor is selected from the group consisting of: thalidomide; prednisone; and etanercept. Thus, in one embodiment, the TNF inhibitor is thalidomide. In another embodiment, the TNF inhibitor is prednisone. In yet another embodiment, the TNF inhibitor is etanercept.

In certain embodiments of the invention methods, the cancer is resistant to EGFR inhibition. In other embodiments, the cancer is a brain cancer selected from the group consisting of: Acoustic Neuroma, Astrocytoma, Pilocytic Astrocytoma, Low-grade Astrocytoma, Anaplastic Astrocytoma, Glioblastoma (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Rhabdoid Tumor. In a particular embodiment, the brain cancer is glioblastoma multiforme (GBM). In certain embodiment for treating brain cancer, each inhibitor is capable of crossing the blood-brain barrier.

In other embodiments of the invention methods, the cancer is selected from the group consisting of: lung cancer, cervical cancer, ovarian cancer, cancer of CNS, skin cancer, prostate cancer, sarcoma, breast cancer, leukemia, colorectal cancer, colon cancer, head and neck cancer, endometrial and kidney cancer, non-small cell lung cancer, human epithelial carcinoma, basal cell carcinoma, squamous cell carcinoma, renal cell carcinoma (RCC), ductal carcinoma in situ (DCIS), and invasive ductal carcinoma.

Also provided herein, are methods of treating a tumor resistant to EGFR inhibition, in a patient in need thereof, comprising administering an agent that inhibits EGFR activity in combination with an agent that inhibits activity of one or more selected from the group consisting of JNK activity, ERK activity and AXL activity. In another embodiment, this particular method can further comprise administering and agent that inhibits TNF activity.

Also provided herein, are pharmaceutical compositions comprising a therapeutically effective amount of an EGFR inhibitor and one or more additional inhibitors selected from the group consisting of a JNK inhibitor, an ERK inhibitor and an AXL inhibitor. The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, and necitumumab. The INK inhibitor is selected from the group consisting of: upstream kinase inhibitor CEP-1347, small chemical inhibitors SP600125 and AS601245, peptide inhibitors of the interaction between INK and its substrates D-JNKI and I-JIP, AEG 3482; BI 78D3; c-JUN peptide; CC 401 dihydrochloride; CEP 1347; IQ 1S; IQ 3; JIP-1 (153-163); SP 600125; SR 3576; SU 3327; TCS INK 5a; and TCS JNK 6o. The ERK inhibitor is selected from the group consisting of: U0126, MK-8353, KO-947, AX 15836, BIX 02189, ERK5-IN-1, FR 180204, Pluripotin, TCS ERK 11e, TMCB, XMD 8-92, BVD-523, GDC-099, SCH772984, DEL-22379, VX-11e, ERK5-IN-1, XMD8-92, LY3214996, SC1, Trametinib, Ulixertinib, GDC-0994, pyrazolylpyrrole, pyrimidinylpyrrole, FR148083, FR180204, and FR180289. The AXL inhibitor is selected from the group consisting of: R428, bemcentinib, YW327.6S2, GL21.T, TP-0903, LY2801653, amuvatinib, bosutinib, MGCD 265, ASP2215, cabozantinib, foretinib, SGI-7079, MGCD516, ASLAN002, and gilteritinib.

In a particular embodiment of the invention composition, the EGFR inhibitor is erlotinib in combination with one or more of the JNK inhibitor SP600125, the ERK inhibitor U0126, and the AXL inhibitor R428. In other embodiments, the combination is selected from the group of combinations consisting of: erlotinib and SP600125 combination; erlotinib and U0126 combination; erlotinib and R428 combination; erlotinib, SP600125 and U0126 combination; erlotinib, SP600125 and R428 combination; erlotinib, U0126 and R428 combination.

In particular embodiments, the composition further comprises an effective amount of a TNF inhibitor. The TNF inhibitor is selected from the group consisting of: thalidomide, pomalidomide, lenalidomide, apremilast, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In a particular embodiment of the invention composition, the TNF inhibitor is selected from the group consisting of: thalidomide; prednisone; and etanercept. Thus, in one embodiment of the composition, the TNF inhibitor is thalidomide. In another embodiment of the composition, the TNF inhibitor is prednisone. In yet another embodiment of the invention composition, the TNF inhibitor is etanercept.

In accordance with the present invention, it has been found that EGFR inhibition in glioma cells results in triggering of a rapid adaptive response that mediates resistance to EGFR inhibition. If this adaptive response is blocked, glioma cells with primary or intrinsic resistance become sensitive to EGFR inhibition and undergo cell death following cessation of EGFR signaling. Previous studies have shown that inhibition of specific tyrosine kinases or key downstream signals in cancer cells leads to a feedback mediated escape from pathway inhibition by reprogramming of signaling pathways that frequently lead to a resumption of previously suppressed signals or activation of alternative signals that are functionally similar. Thus, the cancer cell tries to maintain homeostasis and it is likely that such mechanisms are an important contributor to drug resistance. In accordance with the present invention, it has been found that a TNF-JNK-Axl-ERK signaling axis mediates an adaptive response to EGFR inhibition in glioma cells that is triggered in response to EGFR inhibition. Inhibition of this adaptive response in combination with EGFR inhibition is effective in treatment of glioma tumors in a mouse model.

EGFR gene amplification and overexpression are found in 40-50% of GBMs and about half of these tumors express the constitutively active oncogenic mutant EGFRvIII. EGFRvIII does not bind ligand and is considered constitutively active, although recent studies have revealed a role of co-expressed EGFRwt in the activation of EGFRvIII. A number of studies have demonstrated that EGFRvIII has a greater oncogenic potential compared to EGFRwt. Recent studies have provided key insights into EGFRvIII downstream signaling and elucidated a role of STAT3 as a key downstream signal. However, EGFRwt may also have an oncogenic role in GBM. Activation of EGFRwt may be mediated by co-expression of EGFR ligands in the tumor and a number of studies have documented the presence of EGFR ligands in GBM. In addition, overexpression of EGFRwt may also result in a ligand-independent constitutive signaling. Thus, EGFR signaling is likely to be active in GBM cells that express either constitutively active EGFR mutants or EGFRwt. Furthermore, EGFR signaling in patient derived primary GBM neurospheres as well as in established GBM cell lines appears to have a role in cell survival, since EGFR inhibition in combination with a block of the TNF-JNK-Axl-ERK adaptive response results in cell death in both patient derived primary GBM cells and in established GBM cell lines. Inhibition of the TNF-JNK-Axl- ERK axis in the absence of EGFR inhibition has no significant effect on GBM cell viability.

Multiple efforts to inhibit the EGFR have failed in GBM, the most recent being the failure of a vaccine against EGFRvIII. The first study of targeted EGFR TKI in GBMs involved a single-arm phase II trial of gefitinib in GBM patients at first recurrence. No radiographic responses were noted and median overall survival (OS) was about 39 weeks. Subsequent studies with erlotinib in recurrent GBM patients were also not effective. Trials of EGFR TKIs in combination with temozolomide and XRT in the newly-diagnosed GBM patient population have not demonstrated significantly improved outcomes. Another treatment strategy involves targeting the EGFRvIII mutation, with a vaccine (rindopepimut) conjugated to keyhole limpet hemocyanin (KLH) designed to generate a specific immune response against tumor cells with EGFRvIII mutations. A phase II multicenter trial of rindopepimut in newly-diagnosed GBM patients demonstrated median OS of 21.8 months and 3-year survival of 26%, suggesting some early promise of efficacy. However, interim analysis of the subsequent phase III study of rindopepimut plus temozolomide in newly-diagnosed GBM patients (ACT IV) demonstrated no difference in median OS compared to temozolomide plus control KLH injections, and thus the trial was discontinued early (Clinicaltrials.gov identifier: NCT01480479).

Tumor heterogeneity may also limit the effectiveness of EGFR inhibition. In accordance with the present invention, it has been found that the multiple failures of anti-EGFR therapy in GBM may have resulted, at least in part because of a rapid adaptive response triggered by an increase in TNF signaling. TNF is a central player in the inflammatory response and also in the pathogenesis of cancer. Depending on the cellular context, TNF signaling may promote cell survival or cell death. In accordance with the present invention, it has been found that TNF is the primary mediator of intrinsic resistance to EGFR inhibition and promotes cell survival in response to a loss of EGFR signaling via activation of JNK. JNK, in turn, increases expression of GAS6, a ligand for the Axl receptor. Inhibition of TNF or JNK blocks Erlotinib induced Axl activaton. Axl activation, in turn leads to ERK activation. Thus, in accordance with the present invention, it has been found that interruption of the TNF-JNK-Axl-ERK axis at any node results in increased sensitivity to EGFR inhibition. Our data indicate that in GBM xenograft tumors, erlotinib induces an upregulation of TNF in about 24 hours and the TNF level subsides in about a week, while the JNK-ERK-Axl activation subsides in about 2 weeks. It is thus not feasible to detect EGFR inhibition-induced TNF upregulation or JNK-ERK-Axl activation in archival tissue from patients following erlotinib treatment since tissue is not sampled at early time points following TKI treatment. It is likely that key mechanisms of secondary resistance such as a downregulation of EGFRvIII or upregulation of PDGFRB also contribute to the failure of anti-EGFR treatment. Similarly, a Urokinase receptor-Bim signaling axis may also contribute to EGFR inhibition resistance.

GBM is a devastating and intractable disease. Temozolomide is the first line chemotherapy drug used in GBM, and in combination with surgery and radiation, results in a modest increase in overall survival of patients. No targeted treatment has proven effective in GBM. Our data indicate that EGFR inhibition may be effective, if combined with an inhibition of a component of the TNF-JNK-Axl-ERK signaling axis. Remarkably, the combined inhibition of EGFR and TNF-pathway is effective even in established GBM cell lines which are otherwise completely resistant to EGFR inhibition. The identification of this TNF-JNK-Axl-ERK signaling axis suggests that it may be possible to target and inhibit this adaptive response at multiple nodes, alone or in combination. We have found that EGFR inhibition in conjunction with JNK inhibition is effective in an animal model. Additionally, a combination of EGFR inhibition and thalidomide is also very effective in suppressing the growth of GBM tumors in both a subcutaneous as well as an intracranial animal model. Thalidomide crosses the blood brain barrier and, indeed, has been previously used clinically in GBM without success. This is consistent with our results that show no effect of thalidomide in the absence of EGFR inhibition. Importantly, this approach is effective in EGFRwt as well as mutant EGFRvIII expressing tumors. EGFR expression is detected in the majority of GBMs and thus this approach could be broadly applicable in this disease. Furthermore, a rapid translation of these findings to the clinic is possible, given the wealth of TNF inhibiting drugs and biologicals in clinical practice, including drugs such as thalidomide, pomalidomide, lenalidomide, and apremilast, that penetrate the blood brain barrier.

Primary resistance to EGFR inhibition in cancer cells expressing EGFRwt or non-responsive EGFR mutants may occur because the EGFR does not drive survival/proliferation of these cells; or because adaptive signals prevent cell death. In accordance with the present invention, it has been found that primary resistance in EGFR expressing glioma cells is mediated by a rapid adaptive signaling pathway that is triggered by inhibition of EGFRwt or mutant EGFR. It has been found that a TNF-JNK-Axl-ERK signaling pathway mediates this adaptive response. Inhibition of this pathway in EGFR expressing glioma cells confers sensitivity to EGFR inhibition in cell culture as well as in a mouse model. Because it has been found that resistance is mediated via an early adaptive response, we provide herein methods and compositions of inhibiting this adaptive response and overcoming primary resistance to EGFR inhibition in various cancers, including brain cancers, such as glioblastoma multiforme, and the like.

As used herein, the phrase "EGFR inhibitor" (also referred to as EGFR TKI) or an "agent that inhibits EGFR activity" refers to any agent (molecule) that functions to reduce or inactivate the biological activity of epidermal growth factor receptor (EGFR). Exemplary EGFR inhibitors include erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, and the like.

As used herein, the phrase "JNK inhibitor" or an "agent that inhibits JNK activity" refers to any of the well-known agents (molecules/compounds) that function to reduce or inactivate the biological activity of c-Jun amino terminal kinase (JNK).

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease.

Exemplary INK inhibitors include e.g. upstream kinase inhibitors (for example, CEP-1347), small chemical inhibitors of INK (SP600125 and AS601245), which directly affect kinase activity e.g. by competing with the ATP-binding site of the protein kinase, and peptide inhibitors of the interaction between INK and its substrates (D-JNKI and I-JIP) (see e.g. Kuan et al., Current Drug Targets—CNS & Neurological Disorders, February 2005, vol. 4, no. 1, pp. 63-67(5)).

The upstream kinase inhibitor CEP-1347 (KT7515) is a semisynthetic inhibitor of the mixed lineage kinase family. CEP-1347 (KT7515) promotes neuronal survival at dosages that inhibit activation of the c-Jun amino-terminal kinases (JNKs) in primary embryonic cultures and differentiated PC12 cells after trophic withdrawal and in mice treated with 1-methyl-4-phenyl tetrahydropyridine. Further, CEP-1347 (KT7515) can promote long term-survival of cultured chick embryonic dorsal root ganglion, sympathetic, ciliary and motor neurons (see e.g. Borasio et al., Neuroreport. 9(7): 1435-1439, May 11, 1998).

A third class of inhibitors of the INK signaling pathway represent peptide inhibitors of the interaction between INK and its substrates, as set forth in U.S. Pat. No. 8,080,517, incorporated herein by reference in its entirety for all purposes. As a starting point for construction of such INK inhibitor peptides a sequence alignment of naturally occurring INK proteins may be used. Typically, these proteins comprise INK binding domains (JBDs) and occur in various insulin binding (IB) proteins, such as D31 or IB2. The results of such an exemplary sequence alignment is e.g. a sequence alignment between the INK binding domains of D31, IB2, c-Jun and ATF2 (see e.g. FIGS. 1A-1C of U.S. Pat. No. 8,080,517). Such an alignment reveals a partially conserved 8 amino acid sequence (see e.g. FIG. 1A). A comparison of the JBDs of D31 and IB2 further reveals two blocks of seven and three amino acids that are highly conserved between the two sequences.

Sequences constructed on basis of such an alignment are e.g. disclosed in WO 01/27268. Particularly, WO 01/27268 discloses small cell permeable fusion peptides, comprising a TAT cell permeation sequence derived from the basic trafficking sequence of the HIV-TAT protein and a minimum 20 amino acid inhibitory sequence of D31. Both components are covalently linked to each other. Exemplary inhibitors of the MAPK-JNK signaling pathway disclosed in WO 01/27268, are e.g. L-JNKI1 (INK-inhibitor peptide composed of L amino acids) or the protease resistant D-JNKI1 peptides (INK-inhibitor peptide composed of non-native D amino acids). These INK-inhibitor (JNKI) peptides are specific for INK (JNK1, JNK2 and JNK3). In contrast to those small compound inhibitors as discussed above, the inhibitor sequences in WO 01/27268, e.g. JNKI1, rather inhibit the interaction between INK and its substrate. By its trafficking sequence derived from TAT, the fusion peptide is efficiently transported into cells. Due to the novel properties obtained by the trafficking component the fusion peptides are actively transported into cells, where they remain effective until proteolytic degradation.

Other exemplary JNK inhibitors include AEG 3482; BI 78D3; c-JUN peptide; CC 401 dihydrochloride; CEP 1347; IQ 1S; IQ 3; JIP-1 (153-163); SP 600125; SR 3576; SU 3327; TCS JNK 5a; and TCS JNK 6o; and the like.

As used herein, the phrase "ERK inhibitor" or an "agent that inhibits ERK activity" refers to any of the well-known agents (molecules/compounds) that function to reduce or inactivate the biological activity of "extracellular-signal-regulated kinase" (ERK). ERK1 and ERK2 (collectively "ERK1/2") are related protein-serine/threonine kinases that participate in, amongst others, the Ras-Raf-MEK-ERK signal transduction pathway, which is sometimes denoted as the mitogen-activated protein kinase (MAPK) pathway. This pathway is thought to play a central role in regulating a number of fundamental cellular processes including one or more of cell proliferation, survival, adhesion, cycle progression, migration, differentiation, metabolism, and transcription. The activation of the MAPK pathway has been reported in numerous tumor types including lung, colon, pancreatic, renal, and ovarian cancers. Accordingly, substances that could reduce activation could be of interest for possible treatments.

ERK1/2 appear to be activated by MEK through phosphorylation of both a threonine and a tyrosine residue, namely at Tyr204/187 and Thr202/185. Once activated, ERK1/2 catalyze the phosphorylation of serine/threonine residues of more than 100 substrates and activate both cytosolic and nuclear proteins that are linked to cell growth, proliferation, survival, angiogenesis and differentiation, all hallmarks of the cancer phenotype. Thus it may be beneficial to target ERK to develop and use ERK1/2 inhibitors as a way to inhibit tumor growth.

Exemplary ERK inhibitors are well-known in the art and include those set forth in U.S. Pat. Nos. 9,624,228, 6,743,941, 8,546,404, Yap et al., ChemMedChem. 2011 Jan. 3; 6(1): 38-48, and the like. In particular embodiments, exemplary ERK inhibitors include those selected from the group consisting of: MK-8353 (Merck), KO-947 (Kura Oncology), AX 15836, BIX 02189, ERK5-IN-1, FR 180204, Pluripotin, TCS ERK 11e, TMCB, XMD 8-92, BVD-523, GDC-099, SCH772984, DEL-22379, VX-11e, ERK5-IN-1, XMD8-92, LY3214996, SC1, Trametinib, Ulixertinib (BVD-523, VRT752271), GDC-0994, pyrazolylpyrrole, pyrimidinylpyrrole, FR148083, FR180204, FR180289, and the like.

As used herein, the phrase "Axl inhibitor" or an "agent that inhibits Axl activity" refers to any of the well-known agents (molecules/compounds) that function to reduce or inactivate the biological activity of AXL. O'Bryan et al identified an overexpressed, transforming complementary DNA (cDNA) in human myeloid leukemia cells that they called AXL, a name derived from the Greek anexelekto, meaning uncontrolled (O'Bryan J P, et al., (1991) AXL, a transforming gene isolated from primary human myeloid leukemia cells, encodes a novel receptor tyrosine kinase. Mol Cell Biol 11(10): 5016-5031).

AXL is a receptor tyrosine kinase that transduces signals from the extracellular matrix into the cytoplasm by binding growth factor GAS6 and thus regulates many physiological processes including cell survival, cell proliferation, migration and differentiation. Ligand binding to AXL at the cell surface induces dimerization and autophosphorylation of AXL. Following activation by ligand, AXL binds and induces tyrosine phosphorylation of PI3-kinase subunits PIK3R1, PIK3R2 and PIK3R3; and also GRB2, PLCG1, LCK and PTPN11. Other downstream substrate candidates for AXL include CBL, NCK2, SOCS1 and TNS2. Recruitment of GRB2 and phosphatidylinositol 3 kinase regulatory subunits by AXL leads to the downstream activation of the AKT kinase. GAS6/AXL signaling plays a role in various processes such as endothelial cell survival during acidification by preventing apoptosis, optimal cytokine signaling during human natural killer cell development, hepatic regeneration, gonadotropin-releasing hormone neuron survival and migration, platelet activation, or regulation of thrombotic responses.

AXL can be activated by a variety of mechanisms, the most common being the ligand dependent activation in which AXL binds with GAS6 to form a dimer complex consisting of two AXL molecules bound to two GAS6 molecules. Other activation mechanisms can occur such as ligand independent activation, which tends to happen when AXL is greatly overexpressed or under oxidative stress, e.g., ligand independent AXL activation in vascular smooth muscle cells.

Exemplary AXL inhibitors are well-known in the art and include: bemcentinib (also referred to as BGB324 or R428), an anti-AXL monoclonal antibody (YW327.6S2), an AXL decoy receptor (GL2I.T), an oral AXL inhibitor (TP-0903). Other AXL inhibitors contemplated herein include: LY2801653, amuvatinib (MP-470), bosutinib (SKI-606), MGCD 265, ASP2215, cabozantinib (XL184), foretinib (GSK1363089/XL880), SGI-7079, MGCD516, ASLAN002, and gilteritinib (ASP2215).

In particular embodiments, the EGFR, JNK, ERK, AXL, and/or TNF inhibitors provided for use herein are preferably those that are well-known in the art to cross the blood brain barrier, such as erlotinib, small molecule organic compounds, and the like.

In one embodiment, exemplary brain cancers contemplated for treatment herein can be selected from the group consisting of: glioblastoma multiforme (GBM), neuroblastoma, neuroendocrine tumor, Acoustic Neuroma, Astrocytoma, Pilocytic Astrocytoma, Low-grade Astrocytoma, Anaplastic Astrocytoma, Glioblastoma (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Rhabdoid Tumor, and the like. In a particular embodiment, the brain cancer is glioblastoma multiforme (GBM). In certain embodiment for treating brain cancer, each inhibitor is capable of crossing the blood-brain barrier.

As used herein, the phrase "capable of crossing the blood-brain barrier" refers to the well-known barrier that is formed by special tight junctions between the epithelial cells that surround the brain tissue. All tissue is separated by this layer of epithelial cells, however only the brain epithelial cells have these tight junctions that do not allow larger molecules to pass between them. The main function of the blood-brain barrier is to protect the brain and keep it isolated from harmful toxins that are potentially in the blood stream. The tight junctions between the endothelial cells prevent large molecules as well as many ions from passing between the junction spaces.

Numerous methods are well known in the art for transporting therapeutic molecules through the blood-brain barrier and include: Exosomes (Alvarez-Erviti et al., (2011) Nat Biotechnol. 2011 April; 29(4):341-5; EL Andaloussi et al., (2013) Extracellular vesicles: biology and emerging therapeutic opportunities. Nat Rev Drug Discov. 2013 May; 12(5):347-57); Receptor-mediated permabilitizers (El-Andaloussi et al., (2011) Nat Protoc. 2012 December; 7(12): 2112-26. doi: 10.1038/nprot.2012.131); Nanoparticles (Dadparvar et al., (2011). HI 6 human serum albumin nanoparticles—Development and transport over an in vitro blood-brain barrier model. Toxicology Letters, 206(1), 60-66).

In other embodiments, exemplary cancers contemplated for treatment herein can be selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of non-small cell lung cancer (NSCLC), small cell lung cancer, breast cancer, acute leukemia, chronic leukemia, colorectal cancer, colon cancer, carcinoma, ovarian cancer, or endometrial cancer, carcinoid tumors, metastatic colorectal cancer, islet cell carcinoma, metastatic renal cell carcinoma, adenocarcinomas, bronchoalveolar lung cancers, and non-Hodgkin's lymphoma. In another aspect, the cancer is ovarian, colon, colorectal or endometrial cancer.

The terms "treatment" or "treating" of a subject includes the application or administration of a compound of the invention to a subject (or application or administration of a compound or pharmaceutical composition of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "in combination with" refers to the concurrent administration of a combination of EGFR and either one or both of a JNK inhibitor or ERK inhibitor compounds; or the administration of either one of the compounds prior to the administration of the other inhibitory compound.

Also contemplated herein is the concurrent administration of a combination of EGFR and either one or both of a INK inhibitor or ERK inhibitor; and the concurrent administration of TNF inhibitor compounds; or the administration of either one of the compounds prior to the administration of the other inhibitory compound(s).

As used herein an "effective amount" of a compound or composition for treating a particular disease, such as cancer, is an amount that is sufficient to ameliorate, or in some manner reduce the symptoms associated with the disease. Such amount can be administered as a single dosage or can be administered according to a regimen, whereby it is effective. The amount can cure the disease but, in certain embodiments, is administered in order to ameliorate the symptoms of the disease. In particular embodiments, repeated administration is required to achieve a desired amelioration of symptoms. A "therapeutically effective amount" or "therapeutically effective dose" can refer to an agent, compound, material, or composition containing a compound that is at least sufficient to produce a therapeutic effect. An effective amount is the quantity of a therapeutic agent necessary for preventing, curing, ameliorating, arresting or partially arresting a symptom of a disease or disorder.

As used herein, "patient" or "subject" to be treated includes humans and or non-human animals, including mammals. Mammals include primates, such as humans, chimpanzees, gorillas and monkeys; and domesticated animals.

As used herein, the phrase "EGFR activating mutation(s)" refers to at least one mutation within the protein sequence of EGFR that results in constitutive signaling, which signaling and has been shown to be transforming. Compared to EGFRwt, it is well-known that EGFR activating mutations lead to activation of extensive networks of signal transduction that, in turn, lead to dependence of tumor cells on continuous EGFR signaling for survival.

As used herein, the phrase "EGFR wild type" or EGFRwt refers to epidermal growth factor receptor in its native un-mutated form.

As used herein, the phrase "cancer is resistant to EGFR inhibition" or variations thereof, refers to the well-known mechanism whereby cancer or tumor cells are initially resistant to EGFR inhibition; or have acquired such resistance after initially being susceptible to treatment by a well-known EGFR inhibitor. For example, most EGFR expressing tumors both in the lung and the brain do not appear to be oncogene addicted and EGFR TKIs, so far, have not been effective in such cancers. EGFR gene amplification and increased EGFR expression are detected in 40-50% GBMs, the most common primary malignant adult brain tumor. There has been a substantial, and thus far, unsuccessful effort to inhibit the EGFR as a therapeutic strategy in GBM.

As used herein, a combination refers to any association between two or among more items. The association can be spatial or refer to the use of the two or more items for a common purpose.

As used herein, a pharmaceutical composition refers to any mixture of two or more products or compounds (e.g., agents, modulators, regulators, etc.). It can be a solution, a suspension, liquid, powder, a paste, aqueous or non-aqueous formulations or any combination thereof.

Pharmaceutical compositions containing the invention EGFR and TNF inhibitors, either as separate agents or in combination in a single composition mixture can be formulated in any conventional manner by mixing a selected amount of the respective inhibitor with one or more physiologically acceptable carriers or excipients. Selection of the carrier or excipient is within the skill of the administering profession and can depend upon a number of parameters. These include, for example, the mode of administration (i.e., systemic, oral, nasal, pulmonary, local, topical, or any other mode) and disorder treated. The pharmaceutical compositions provided herein can be formulated for single dosage (direct) administration or for dilution or other modification. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed, or otherwise mixed in a selected vehicle at an effective concentration such that the treated condition is relieved or ameliorated.

Generally, pharmaceutically acceptable compositions are prepared in view of approvals for a regulatory agency or other prepared in accordance with generally recognized pharmacopeia for use in animals and in humans. Pharmaceutical compositions can include carriers such as a diluent, adjuvant, excipient, or vehicle with which an isoform is administered. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions.

It is understood that appropriate doses depend upon a number of factors within the level of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the therapeutic agent to have upon the subject. Exemplary doses include milligram or microgram amounts of the therapeutic agent per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays known in the art. When one or more of these compounds is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of compound of the invention calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a compound of the invention for the treatment of the disease.

Examples

Materials & Methods
Plasmids, Transfection and Generation of Cell Lines

The methods employed herein are substantially as described in Guo et al., Nature Neuroscience, published online 06/12/17; doi:10.1038/nn.4584, which is incorporated herein by reference in its entirety for all purposes.

Primary GBM neurosphere cultures were generated directly from human GBM tumor specimens. Cells were cultured in DMEM F12 supplemented with B27 without Vitamin A, and with EGF (20 ng/ml) and bFGF (20 ng/ml). Cell lines were authenticated using a Promega StemElite ID system which is an STR based assay. NF-kB-LUC plasmid was provided by Dr. Ezra Burstein (UT Southwestern). The 3xAP1pGL3 reporter plasmid was obtained from Addgene (#40342).

Luciferase Assays

Cells were plated in 48 well dishes to 70%-80% confluence followed by with NF-αB-LUC or 3xAP1pGL3 reporter plasmid using lipofectamine 2000. A dual-luciferase reporter assay system was used according to manufacturer's instructions (Promega, Madison WI). Firefly luciferase activity was measured in a luminometer and normalized on the basis of Renilla luciferase activity. Experiments were done in triplicate and 3 independent experiments were done.

RNA Interference

For transient silencing we used a pool of siRNA sequences directed against human TNFR1, Axl, JNK1, JNK2 or control (scrambled) obtained from Santa Cruz. siRNAs were introduced into cells using the Lipofectamine2000 (Invitrogen Carlsbad, CA) according to the manufacturer's instructions. Experiments were conducted 48 h after siRNA transfection. Knockdown efficiency was confirmed by Western blotting.

Antibodies, Reagents and Western Blotting

Western blot analysis was performed according to standard protocols. In all experiments, before the addition of EGF or erlotinib established cells were cultured overnight in serum free DMEM and primary GBM neurospheres were EGF starved overnight. Cells not treated with EGF or erlotinib were also serum or EGF starved. EGFR (06-847, 1 μg/ml) antibody was from Millipore. pEGFR-1068 (2236), pERK (4376) ERK (4695), p34 (9251), JNK (9252), STAT3 (9139), pAkt (0915) and pSTAT3 (9131) antibodies were from Cell Signaling Technology (Danvers, MA) were used a 1/1000 dilution; TNFR1 (sc-8436), ERK2 (sc-154). Akt (sc-1619), and β-Actin (sc-47778) were from Santa Cruz Biotechnology (Dallas, TX) were used at a concentration of 1 μg/ml. GAS6 (AF885), pAxl (AF2228) and Axl (AF154) were from R&D Biosystems (Minneapolis, MN) were used at a concentration of 1 μg/ml c-JUN antibody (ab31419) was from Abcam (Cambridge, MA) and was used at 2 μg per chromatin IP reaction.

Reagents: Recombinant human TNF and EGF were obtained from Peprotech (Rocky Hill, NJ). Erlotinib and XL765 was purchased from SelleckChem (Houston, TX). Afatinib was bought from AstaTech, Inc. (Bristol, PA). Axl inhibitor R428, ERK inhibitor (U0126) and thalidomide were from Cayman Chemical (Ann Arbor, MI). Enbrel (Etanercept) was purchased from Mckesson Medical y (San Francisco CA). The JNK inhibitor SP600125, p38 Inhibitor SB203580, and NF-αB inhibitor BMS-345541 were obtained from EMD Millipore (Billerica, MA). Necrostatin-1 was obtained from Fisher Scientific (Pittsburgh, PA). LPS was purchased from Sigma (St. Louis, MO). Cetuximab was provided by Imclone and used at a concentration of 10 μg/ml overnight.

Chromatin Immunoprecipitation Assay

GBM9 and U87EGFRwt cells were cultured in 15 cm plate per reaction for assay. ChIP assays were carried out using ChIP chromatin immunoprecipitation kit (Millipore) following manufacturer's instructions. The ChIP-enriched DNA samples were quantified by PCR using Platinum Taq DNA polymerase (Invitrogen). Putative AP-1 binding sites on GAS6 promoter were predicted by Using TFBIND program. The following primer pairs covering AP-1 sites were used: 5'-GGATCTGACCTCAGTGTATC-3' (SEQ ID NO:1) and 5'-TGGTTGTCTTCACTAGCGAT-3' (SEQ ID NO:2).

cDNA Synthesis and Real Time PCR

Total RNA was isolated by TRIzol Reagent (Ambion). cDNA Reverse Transcription were performed by using High-Capacity cDNA Reverse Transcription Kit (Applied Biosystems). PCR primers were synthesized by IDT (Coralville, IA). Each PCR was carried out in triplicate in a 20 μl volume using SYBR Green Master Mix (Applied Biosystems) for 15 minutes at 95° C. for initial denaturing, followed by 40 cycles of 95° C. for 15 s and 60° C. for 60 s in ViiA 7 Real-Time PCR System (Applied Biosystems). At least two independent experiments were done. Values for each gene were normalized to expression levels of GAPDH mRNA. The following primers were used: TNF, 5'-CCCAGGGACCTCTCTCTAATCA-3' (SEQ ID NO:3) and 5'-GCTACAGGCTTGTCACTCGG-3' (SEQ ID NO:4); GAS6, 5'-CATCAACAAGTATGGGTCTCCGT-3' (SEQ ID NO:5) and 5'-GTTCTCCTGGCTGCATTCGTTGA-3' (SEQ ID NO:6); GAPDH, 5'-GTGAAGGTCGGAGT-CAACGG-3' (SEQ ID NO:7) and 5'-TGATG-ACAAGCTTCCCGTTCTC-3' (SEQ ID NO:8).

ELISA $2 \times 10^6$ cells were incubated in serum-free or EGF free medium containing different concentrations of erlotinib or DMSO. After 48 hours, supernatant and cell lysates were collected. Supernatant medium was concentrated 5-10-fold with Pierce protein concentrator (ThermoFisher). TNF protein concentration in supernatant, cell lysates and tissue extracts was determined by ELISA using a commercial TNF detection kit (ThermoFisher) according to manufacturer's instructions. Additionally, GAS6 protein concentration in supernatant was measured by ELISA kit (LifeSpan BioSciences).

Cell Viability Assay

Cell viability assay was conducted using AlamarBlue cell viability assay kit (ThermoFisher) following manufacturer's protocol. Cells were cultured in Corning 96-well black plates with clear bottom (5000 cells/well). Drugs were added to cells for 72 hour following detection using POLARstar Omega Microplate Reader (excitation at 544 nm and emission at 590 nm) (BMG LABTECH, Germany).

Animal Studies 4 to 6 weeks old female athymic nude mice were purchased from Charles River Laboratories. The mice were housed in plastic cages (4-5 mice per cage) in a room with a 12 hour day-night cycle. $1 \times 10^6$ GBM9 cells were subcutaneously injected into the right flank of each nude mouse. After about 10 days post injection, all mice had developed subcutaneous tumors. The mice were randomly divided into control and treatment groups, mice were treated with drugs using the indicated doses. For combination treatment, both drugs were given concurrently for indicated periods. Tumor dimensions were measured by caliper every two days and tumor volumes calculated by the formula: volume=length× width×width/2. Mice were sacrificed when tumors reached over 2000 m$^3$ or 24 days from the first day of treatment.

For the orthotropic model, $1 \times 10^5$ GBM9 cells expressing firefly luciferase were injected into the right corpus striatum of the brains of 6-8-week-old nude mice using a stereotactic frame. When tumors became apparent on BLI (7 days after injection), mice were randomly divided into four groups (control gavage group, afatinib group, thalidomide group and afatinib plus thalidomide group, n=8). The mice were treated with erlotinib 50 mg/kg by oral gavage and/or intraperitoneal (i.p.) injection of 150 mg/kg thalidomide for 10 consecutive days. Bioluminescence imaging (BLI) was performed to record the growth of tumor every 5 days. Kaplan-Maier survival curves were calculated using Graph-Pad Prism 7.0 software. Mice were monitored and sacrificed when neurological signs appeared or after 40 days.

To detect the in vivo levels of TNF, $1 \times 10^6$ GBM9 cells were injected into the right flanks of nude mice. When the subcutaneous tumor reached a volume of around 200 mm$^3$, the mice were treated with erlotinib to monitor the upregulation of TNF protein. The animals were dosed consecutively for 1, 2, 7 or 14 days and then sacrificed. The animals without treatment were considered as control (0-day treatment). Tumor tissues were rinsed in PBS and protein was extracted to analyze the TNF levels using ELISA and also used for western blot. To detect the protein expression in mice brain tumor tissues upon drug treatment, the same procedure was performed in orthotopic models. Additionally, with orthotopic models, mice were divided into four groups (control gavage group, erlotinib group, thalidomide group and erlotinib plus thalidomide, n=3). After 48 hours treatment tumors were harvested and subjected to Western blot and immunostaining.

All animal studies were done under Institutional Animal Care and Use Committee-approved protocols.

Immunohistochemistry

Tumors from nude mice brains were fixed in 10% formalin and embedded in paraffin. Paraffin-embedded sections were cut at five-micrometer thickness. Immunohistochemical staining was performed using the ABC streptavidin-biotin method with the Vectastain ABC kit (Vector Laboratories, Burlingame, CA, USA) according to the manufacturer's protocol. Briefly, after deparaffinization and rehydration, endogenous peroxidase activity was quenched by a 10 min incubation in 3% $H_2O_2$. For antigen retrieval, the tissue sections were boiled in 10 mM sodium citrate buffer (pH 6.0) for 20 minutes. Binding of primary anti-pERK (1:100, Cell Signaling Technology, 4376) or anti-pJNK antibody (1:200, Cell signaling Technology, 4668) or anti-pAXL(1:400, R&D, AF2228) was carried out overnight at 4° C. The signal was detected by using the Sigmafast 3,3'-Diaminobenzidine tablets (DAB; Sigma, St. Louis MO). The sections were counterstained lightly with hematoxylin. The IHC staining intensity was scored semiquantitatively as: 0=No positive staining; 1=1-25% tumor cells stained, 2=26%-75% tumor cells stained and 3=>75% tumor cells stained.

Cell Death/Annexin Assay

Annexin assay was performed by using Annexin—V-FLUOS Staining kit (Roche applied Science). Cells ($1 \times 10^6$) were plated in 6 well plates and treated with drugs or vehicle alone. After 72 hours cells were trypsinized and washed 2 times with 1×PBS. The cells were incubated for 15 minutes at room temperature with Propidium Iodide and Annexin—V-FLUOS labeling solution in incubation buffer. Annexin and/or PI positive cells were detected by Flow Cytometry.

Caspase-3/7 Activity

Caspase activity in the supernatant was measured using the Caspase-Glo 3/7 Assay (Promega, G8091) following manufacturer's instructions. Briefly, 72 hours after treatments, cells were washed by cold PBS and total cell lysates were prepared. 50 μg of total protein per sample was added per well of a 96 well plate and was incubated with 100 μl Caspase 3/7 reagent for 30 minutes. The luminescence of each sample was measured using a luminometer. All experiments included at least 3 replicates per group and were repeated 3 times.

Statistical Analysis

All data were analyzed for significance using GraphPad Prism 7.0 software. Error bars represent the means±s.e.m of three independent experiments if not indicated. We used 8 mice per group based on power analysis. This sample size calculation is based upon tumor volume measured at 4 weeks after drug administration. Specifications and assumptions for this calculation are: 1, a tumor volume change of 50% for the treated group as compared with the control group, 2, a standard deviation of 30% for tumor volume in each of the comparison groups, 3, power of 85% and two-sided type I error rate of 5%, 4, use of two-sample t-test. (Total mice:32). Two-tailed unpaired Student's t-test were used for comparison of two data sets. The Mann-Whitney U test was applied to test the significant differences in IHC staining intensity between different groups. Data distribution was assumed to be normal, but this was not formally tested. Samples and animals were randomized for experimentation, data collection and analysis were not performed blind to the conditions of the experiments. At least 3 independent molecular and biochemical analyses were performed unless otherwise indicated. P<0.05 was considered statistically significant. * means that P<0.05,  means that P<0.01, * means that <0.001 and **** indicates any P value less than 0.0001.

Results

Erlotinib Induces a Feedback Activation of ERK in Glioma Cells

In order to elucidate mechanisms of EGFR inhibition resistance in glioma cells, we examined signal transduction events following erlotinib exposure in glioma cells. We used EGFR expressing patient derived primary GBM neurospheres as well as established glioblastoma cell lines expressing EGFRwt or EGFRvIII as shown in FIG. 1A. Signaling from EGFRvIII is constitutive, while signaling from overexpressed EGFRwt may be constitutive or ligand induced. GBM9, GBM39 and SK987 neurospheres express EGFRvIII and also EGFRwt and have been described previously. We started our investigation by examining activation of Akt, STAT3 and ERK, since these pathways play an important role in cancer cell survival. Exposure of GBM9 neurospheres to erlotinib demonstrated ERK activation in untreated cells that decreased after addition of erlotinib suggesting that EGFR was driving the activation of ERK. A reactivation of ERK is seen at 24-48 h in erlotinib treated cells, likely triggered by a feedback mechanism, since the EGFR remains inactivated (FIG. 1B). However, we did not detect an increase in Akt or STAT3 activation (FIG. 1B). Similar results were found in patient derived primary GBM39 and SK987 cells (FIG. 1C-D). We also examined signal transduction in established glioblastoma cell lines U87EGFRwt, U87EGFRvIII and U251EGFRwt and found a similar feedback activation of ERK in response to EGFR inhibition (FIGS. 1E-F and FIG. 8A). Also, similar results were found with afatinib, an irreversible inhibitor of EGFR kinase, (FIG. 8B). If we use a higher concentration of erlotinib, STAT3 and Akt activation are suppressed. However, we do not detect any reactivation of STAT3 or Akt in the presence of continuing EGFR inhibition (FIG. 8C-G). Thus, of the three pathways examined, only ERK became activated in response to EGFR inhibition. In U87EGFRwt cells, ERK and EGFR activation are similar in serum or serum free conditions (FIG. 8H). Basal EGFR and ERK activation could be inhibited by Cetuximab, which blocks ligand binding to the EGFR, suggesting autocrine activation of EGFR under serum starved conditions (FIG. 8I). As expected, further increases in EGFR and ERK activation were detected when exogenous EGF was added (FIG. 8J).

Inhibition of Axl Blocks EGFR Inhibition Mediated ERK Activation

Activation of other receptor tyrosine kinases such as Met or Axl has been identified as a major mechanism of secondary resistance to EGFR inhibition in lung cancer cells. In glioma, EGFRvIII expression leads to coactivation of multiple RTKs, such as Met and a combined inhibition of EGFR and Met or Akt/mTOR is more effective than inhibition of the EGFR alone. Increased expression of PDGFRβ has been described in response to prolonged EGFR inhibition in glioma cells. We detected phosphorylation of the RTK Axl following exposure of cells to erlotinib for 48 h in patient derived GBM neurospheres and in all cell lines examined (FIGS. 1B-F and FIG. 8A). Erlotinib also induces activation of Met in established cell lines, but only in one patient derived neurosphere 987 (FIGS. 1B-F and FIG. 8A). Since Axl activation is seen in all patient derived neurospheres and established cell lines tested, we focused on Axl in this study.

We examined if Axl was responsible for activation of ERK in response to EGFR inhibition. We used the Axl inhibitor R428 and found that inhibition of Axl results in a block of erlotinib induced ERK activation in patient derived GBM neurospheres as well as in multiple cell lines as shown in FIG. 1G-J. Similarly, siRNA knockdown of Axl also results in a block of erlotinib induced ERK activation (FIG. 1K-N). Thus, Axl plays an essential role in EGFR induced inhibition of ERK activation.

Activation of JNK by EGFR Inhibitor Triggers a Survival Feedback Loop

Figures 2A, 2B, 2C, 2D, 2E, 2F, 2G, 2H, 2I, 2J, 2K, 2L:
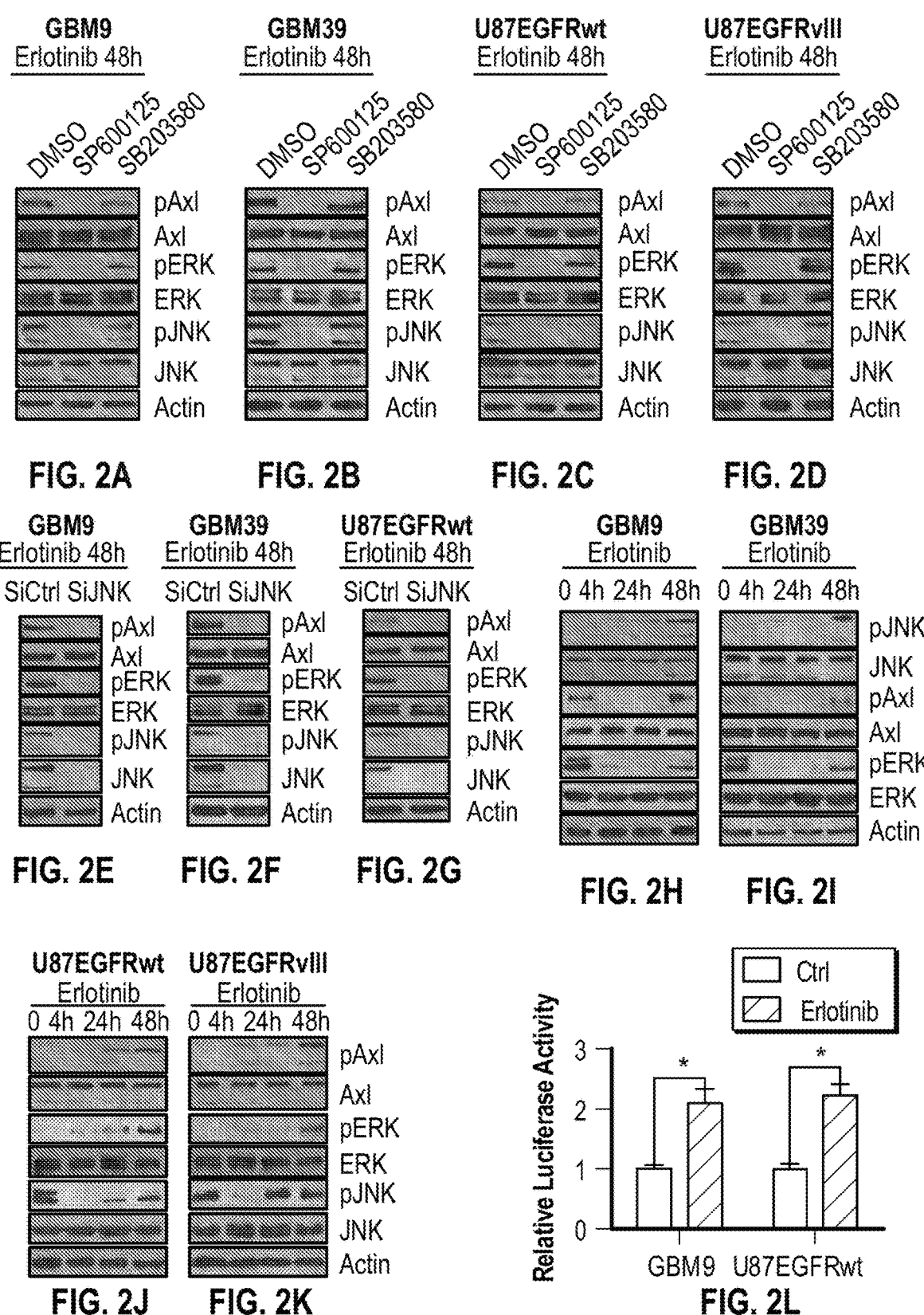
FIG. 2A-FIG. 2L—EGFR Inhibition Induced Axl and ERK Activation is Mediated by JNK FIG. 2A-FIG. 2B Patient derived primary GBM neurospheres were exposed to erlotinib for 48 hours in the presence or absence of JNK inhibitor SP600125 (1 μM) or p38 inhibitor SB203580 (10 μM) followed by Western blot with the indicated antibodies.

We next examined whether inhibition of key signaling pathways known to be active in EGFR signaling could block erlotinib induced Axl and ERK activation. We found that the JNK inhibitor SP600125 inhibited erlotinib induced activation of Axl and ERK in patient derived neurospheres and established GBM cell lines, but the p38 MAPK inhibitor SB203580 failed to do so (FIG. 1A-D). We also found that siRNA knockdown of JNK 1 and 2 resulted in a block of erlotinib induced EGFR Axl and ERK activation (FIG. 2E-G). Furthermore, erlotinib exposure of cells results in activation of INK as detected by phosphorylation of INK in Western blots (FIG. 2H-K). These findings suggest that INK activation plays an essential role in erlotinib induced ERK activation. INK refers to cJun NH$_2$-terminal kinases that are MAP kinases that phosphorylate c-Jun. This results in activation of the transcription factor AP1. Consistent with data demonstrating INK activation in response to EGFR inhibition, erlotinib also induces increased activity of the AP-1 reporter (FIG. 2L). These experiments support a model in which EGFR inhibition leads to the activation of INK signaling and, in turn, INK signaling mediates an activation of Axl. Axl activation then leads to ERK activation.

Figures 9A, 9B, 9C, 9D, 9E, 9F, 9G, 9H, 9I:
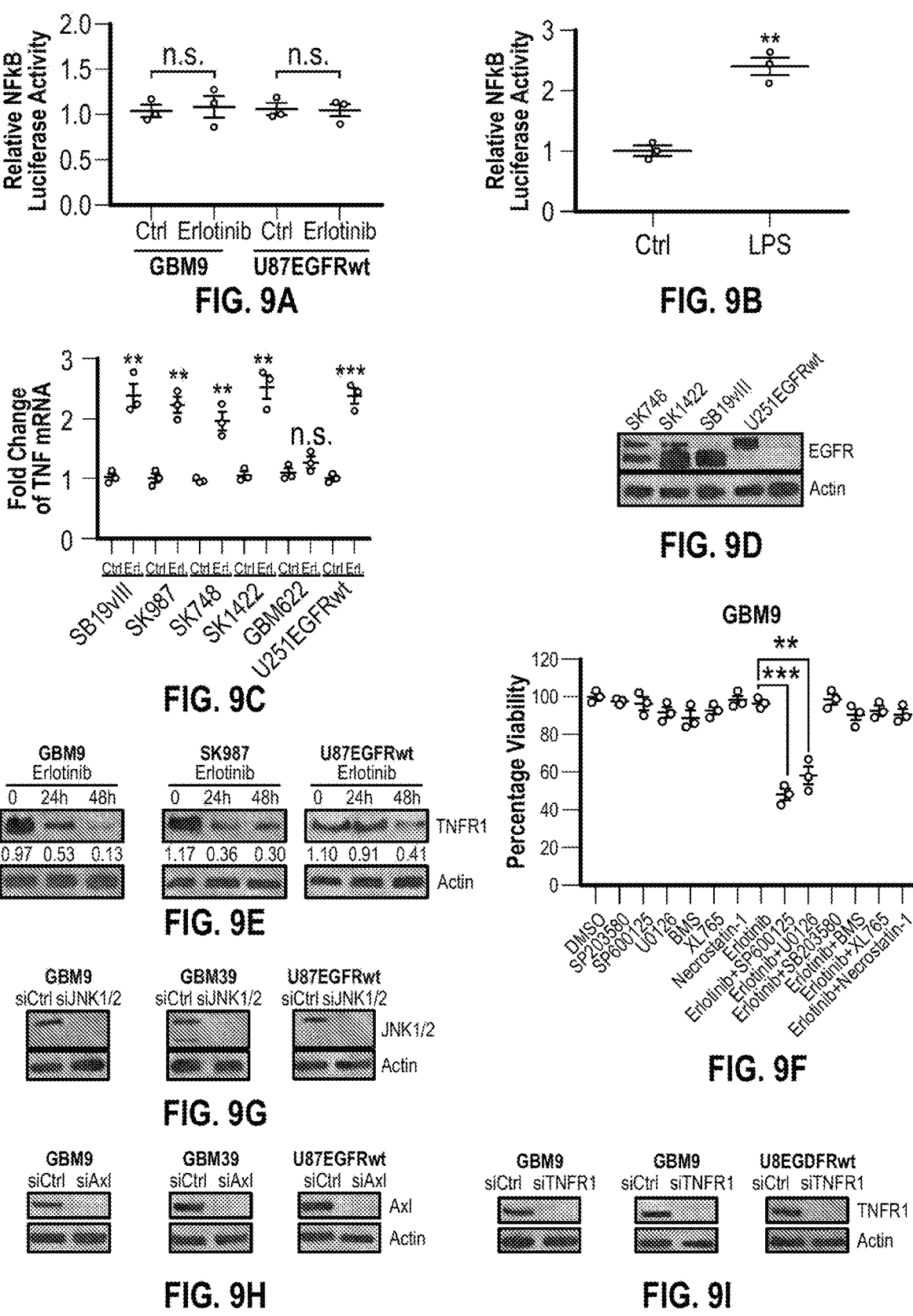
FIG. 9A-FIG. 9I—Intracellular Signaling Networks and Biological Responses to EGFR Inhibition in Glioma Cells FIG. 9A-FIG. 9B EGFR inhibition does not activate NF-κB transcriptional activity.

EGFR inhibition has also been reported to result in a rapid activation of NF-κB in lung cancer cells expressing EGFR activating mutations. However, we did not detect an increase in NF-κB transcriptional activity in response to EGFR inhibition in glioma cells, whereas LPS efficiently activated NF-κB transcriptional activity (FIG. 9A-B).

Activation of Axl Results from Increased Expression of GAS6

Figures 3A, 3B, 3C, 3D, 3E, 3F, 3G, 3H, 3I:
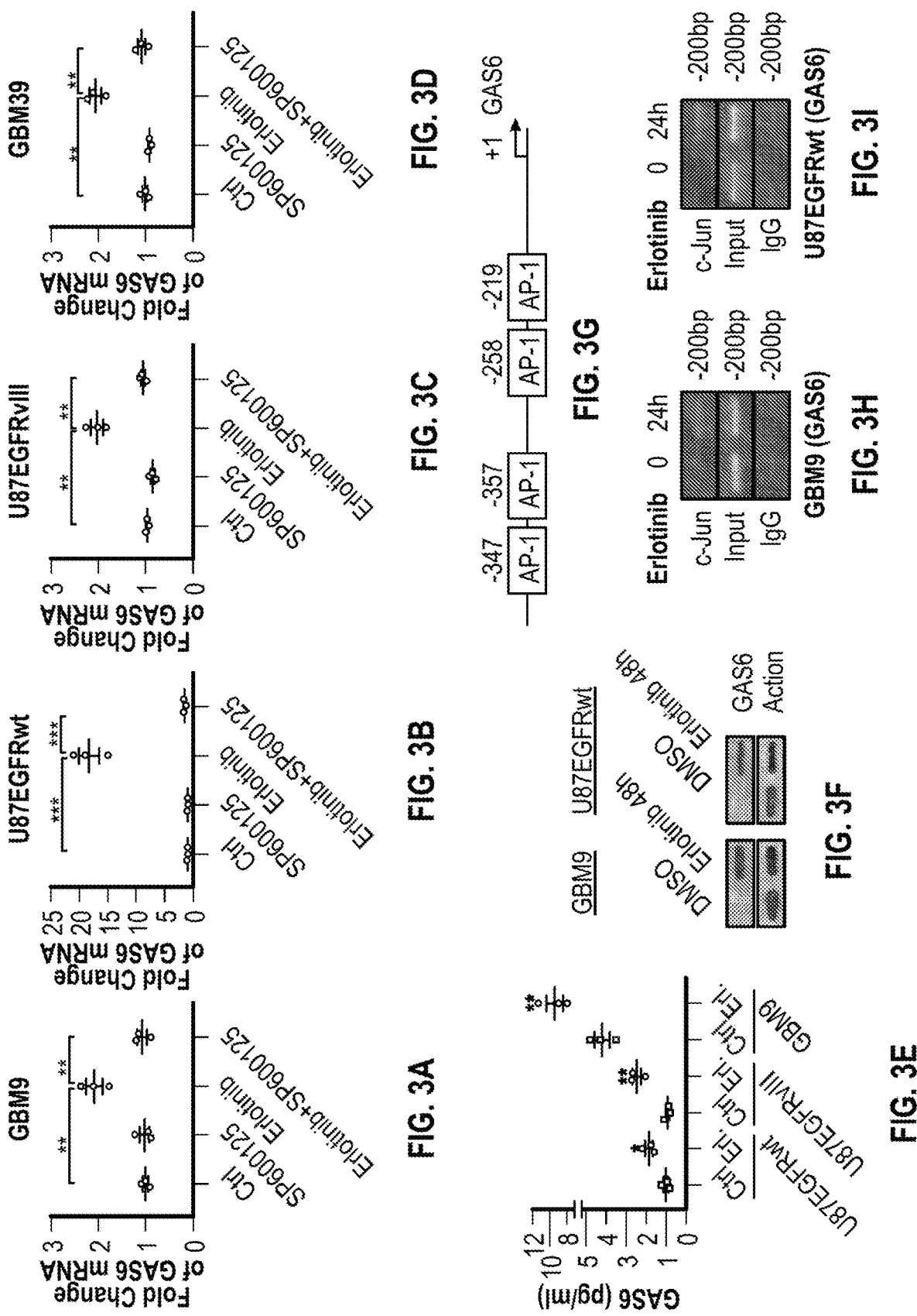
FIG. 3A-FIG. 3I—EGFR Inhibition Leads to Increased GAS6 Levels Via a JNK Dependent Mechanism FIG. 3A GBM9 neurospheres were exposed to erlotinib in the absence or presence of JNK inhibitor SP600125 for 24 h (1 μM) for 24 h followed by quantitative real time PCR for GAS6 mRNA. GAS6 is increased upon EGFR inhibition, and this increase is blocked by JNK inhibition. Ctrl vs erlotinib: P=0.0039, t=5.98, d.f.=4; erlotinib vs erlotinib+ SP600125: P=0.0070, t=5.10, d.f.=4. (b-d) A similar experiment was undertaken in U87EGFRwt, U87EGFRvIII and patient derived neurosphere GBM39.

Next, we examined the mechanism of Axl activation following exposure to erlotinib. Axl is activated about 24-48 hours after the EGFR is inhibited. We investigated the possibility that erlotinib may lead to increased expression of GAS6, the ligand for Axl. We examined the erltoinib induced expression of GASs6 at various time points by real time quantitative PCR. EGFR inhibition leads to an increase in GAS6 in patient derived neurospheres and in established GBM cell lines (FIG. 3A-D). Importantly, inhibition of JNK blocks erlotinib induced expression of GAS6 (FIG. 3A-D), consistent with the previously noted inhibition of erlotinib induced Axl activation by a chemical inhibition or silencing of JNK. An increased level of GAS6 was confirmed by ELISA and Western blot (FIG. 3E-F). These findings suggest that erlotinib induced activation of Axl likely results from increased levels of GAS6. Next, we examined whether activation of JNK leads to increased transcription of GAS6. Using TFBIND program, multiple predicted c-Jun (AP-1) binding sites were identified 500 bp upstream of the putative transcription start site of GAS6 (FIG. 3G). We then undertook a chromatin immunoprecipitation (ChIP) assay to investigate the presence of AP-1 at the GAS6 promotor. Erlotinib exposure leads to the binding of cJun to the GAS6 promoter in GBM9 and U87EGFRwt cells as shown in FIG. 3H-I.

JNK is Activated by an Erlotinib Induced Increase in TNF Levels

Figures 4A, 4B, 4C, 4D, 4E, 4F, 4G, 4H, 4I:
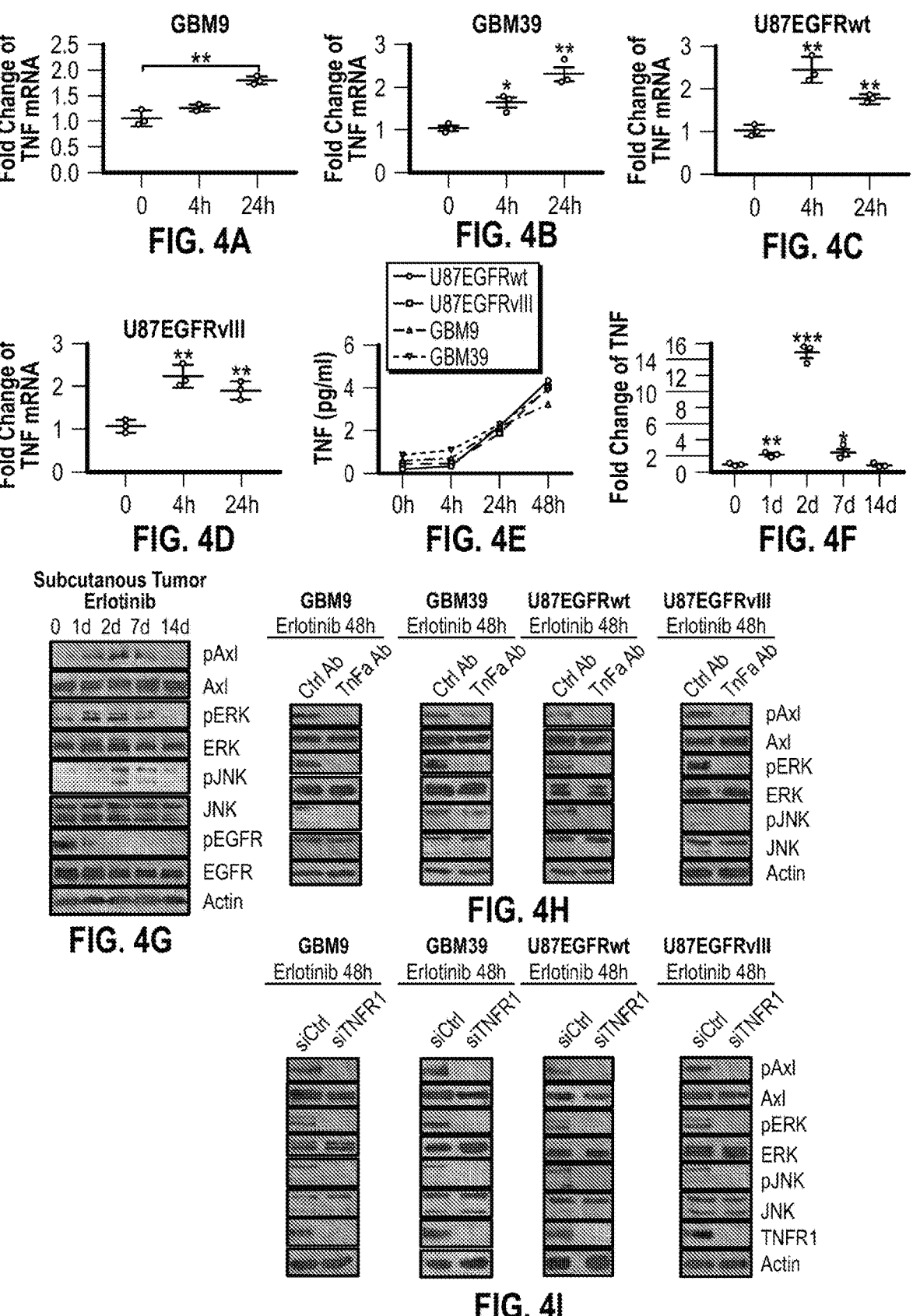
FIG. 4A-FIG. 4I—EGFR Inhibition Leads to Increased TNF Signaling that Triggers an Adaptive Signaling Pathway FIG. 4A-FIG. 4B EGFR inhibition leads to an increase in TNF mRNA in patient derived GBM9 and GBM39 neurospheres. Cells were exposed to erlotinib (100 nM) for the times indicated followed by qRT-PCR for TNF mRNA.

Next, we examined the mechanism of erlotinib-induced JNK activation. Previous studies have found that EGFR inhibition in lung cancer cells results in increased secretion of inflammatory cytokines. We hypothesized that EGFR inhibition in glioma cells may lead to a similar release of cytokines. Since TNF is a known and potent activator of JNK, we examined the level of TNF in patient derived GBM neurospheres as well as EGFR expressing cell lines. Erlotinib leads to a significant and rapid increase in TNF mRNA levels as determined by real time quantitative PCR and shown in FIG. 4A-D. The increase in TNF was confirmed at a protein level by ELISA as shown in FIG. 4E. Increase in TNF levels was noted in multiple additional lines and patient derived neurospheres as shown in FIG. 9C-D. Importantly, increased TNF levels can also be induced by EGFR inhibition in tumors growing in mice as shown in FIG. 4F. In this experiment patient derived primary GBM9 cells were injected into the flanks of nude mice. After formation of palpable tumor, erlotinib was administered as indicated followed by harvesting of tumors and ELISA for TNF. An erlotinib induced increase in TNF can be detected 1 day after administration of erlotinib (FIG. 4F). In addition, we also detect erlotinib induced activation of JNK, Axl and ERK in mouse tumors (FIG. 4G), peaking around 2-7 days and subsiding by 14 days.

Next, we examined whether TNF played an essential role in erlotinib induced JNK activation. Indeed, we find that the use of a neutralizing antibody to TNF lead to inhibition of erlotinib-induced JNK activation (FIG. 4H). Furthermore, erlotinib-induced Axl and ERK activation were also blocked by TNF inhibition. Similar results were found with siRNA knockdown of TNFR1 (FIG. 4I). We also examined the level of TNFR1 in glioma cells treated with erlotinib. We found that erlotinib induces a downregulation of TNFR1 in patient derived samples and established GBM cell lines as shown in FIG. 9E. As it is known that TNF induces downregulation of its receptor, this finding provides evidence that TNF signaling is activated by EGFR inhibition.

Figures 5A, 5B, 5C, 5D, 5E, 5F, 5G, 5H, 5I, 5J, 5K, 5L, 5M, 5N:
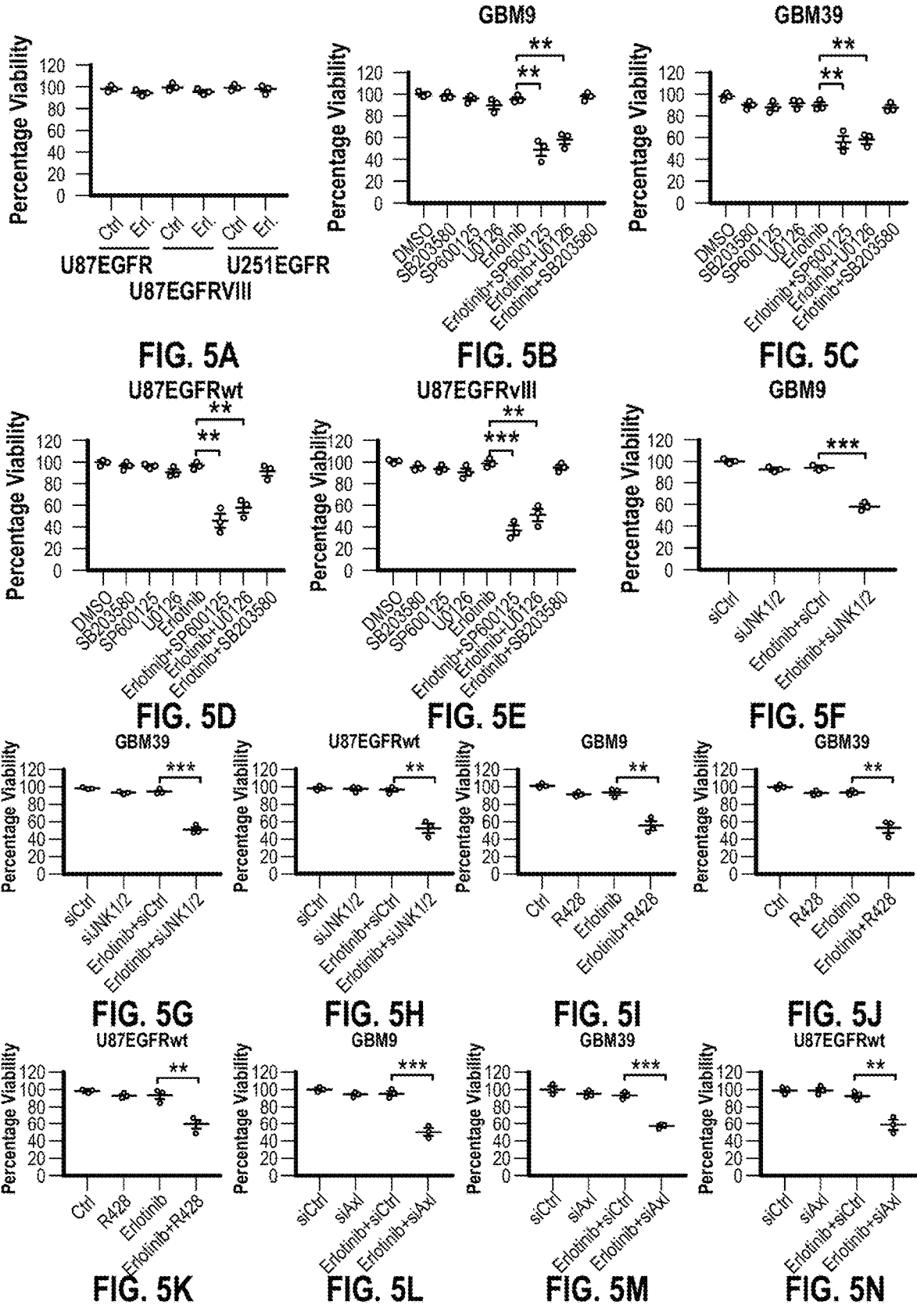

Inhibition of the TNF-JNK-Axl-ERK Axis Confers Erlotinib Sensitivity to EGFR Expressing Glioma Cells To investigate if this TNF-JNK-Axl-ERK signaling pathway influences the biological response to EGFR inhibition, we examined the effect of inhibiting this pathway on the viability of glioma cells exposed to erlotinib. First we examined the sensitivity of EGFR expressing GBM cell lines to erlotinib. The established cell lines appear to be completely resistant to Erlotinib regardless of whether EGFRwt or EGFRvIII is expressed (FIG. 5A). Patient derived primary neurosphere GBM9 and GBM39 cells are resistant to EGFR inhibition at a low concentration of erlotinib (100 nM). However, when combined with JNK inhibition using SP600125 or ERK inhibition using U0126, erlotinib leads to a significant cell death, while cells are resistant to JNK or ERK inhibition alone (FIG. 5B-C). Inhibitors of multiple other signaling pathways failed to sensitize glioma cells to EGFR inhibition (FIG. 9F). Established glioblastoma cell lines are also resistant to EGFR inhibition or JNK inhibition or ERK inhibition alone, but a combined inhibition of EGFR with ERK or JNK leads to a significant cell death (FIG. 5D-E). A biological inhibition of JNK using siRNA knockdown also renders glioma cells sensitive to EGFR inhibition as shown in FIGS. 5F-H and FIG. 9G.

Next, we examined whether inhibition of Axl would also render resistant glioma cells sensitive to EGFR inhibition, since Axl inhibition blocks the erlotinib induced ERK activation. Indeed, as shown in FIG. 5I-K, a specific chemical inhibitor of Axl R428 renders patient derived GBM neurospheres and U87EGFRwt cells sensitive to erlotinib. R428 by itself does not affect the viability of these cells. Axl inhibition also confers sensitivity to erlotinib in established GBM cell lines (FIG. 5J). Similarly siRNA knockdown of Axl, also confers erlotinib sensitivity to GBM9, GBM39 and U87EGFR cells (FIGS. 5L-N and FIG. 9H).

Figures 6A, 6B, 6C, 6D, 6E, 6F, 6G, 6H, 6I, 6J, 6K, 6L, 6M, 6N:
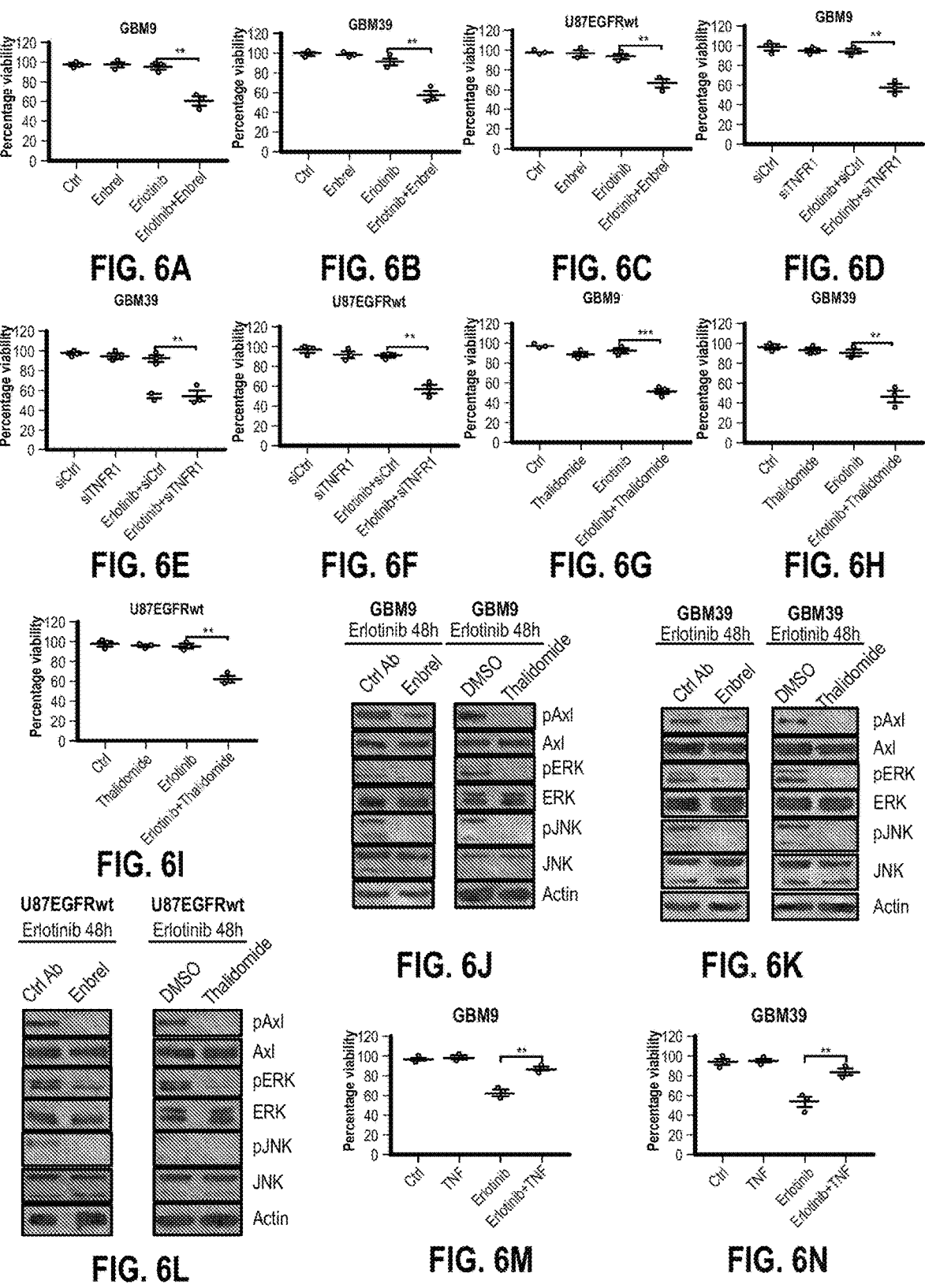
Figures 10A, 10B, 10C, 10D, 10E, 10F:
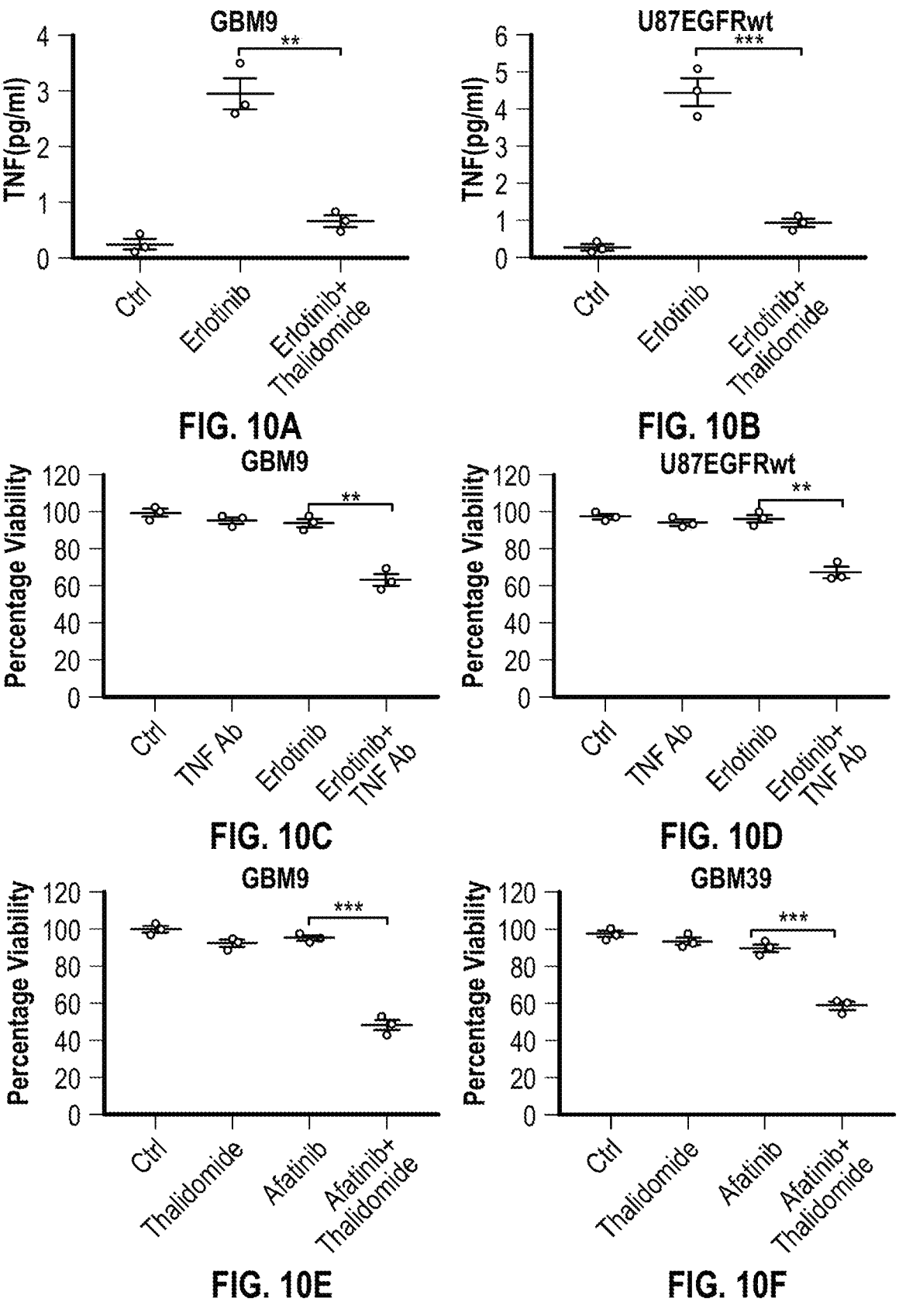
FIG. 10A-FIG. 10F—EGFR Inhibition Induces a Biologically Significant Upregulation of TNF in Glioma Cells FIG. 10A-FIG. 10B Thalidomide blocks EGFR inhibition induced upregulation of TNF. Patient derived GBM9 neurospheres or established GBM cell line U87EGFRwt cells were treated with erlotinib with or without thalidomide (1 μM) followed by collection of supernatants and TNF ELISA.
Figure 11A:
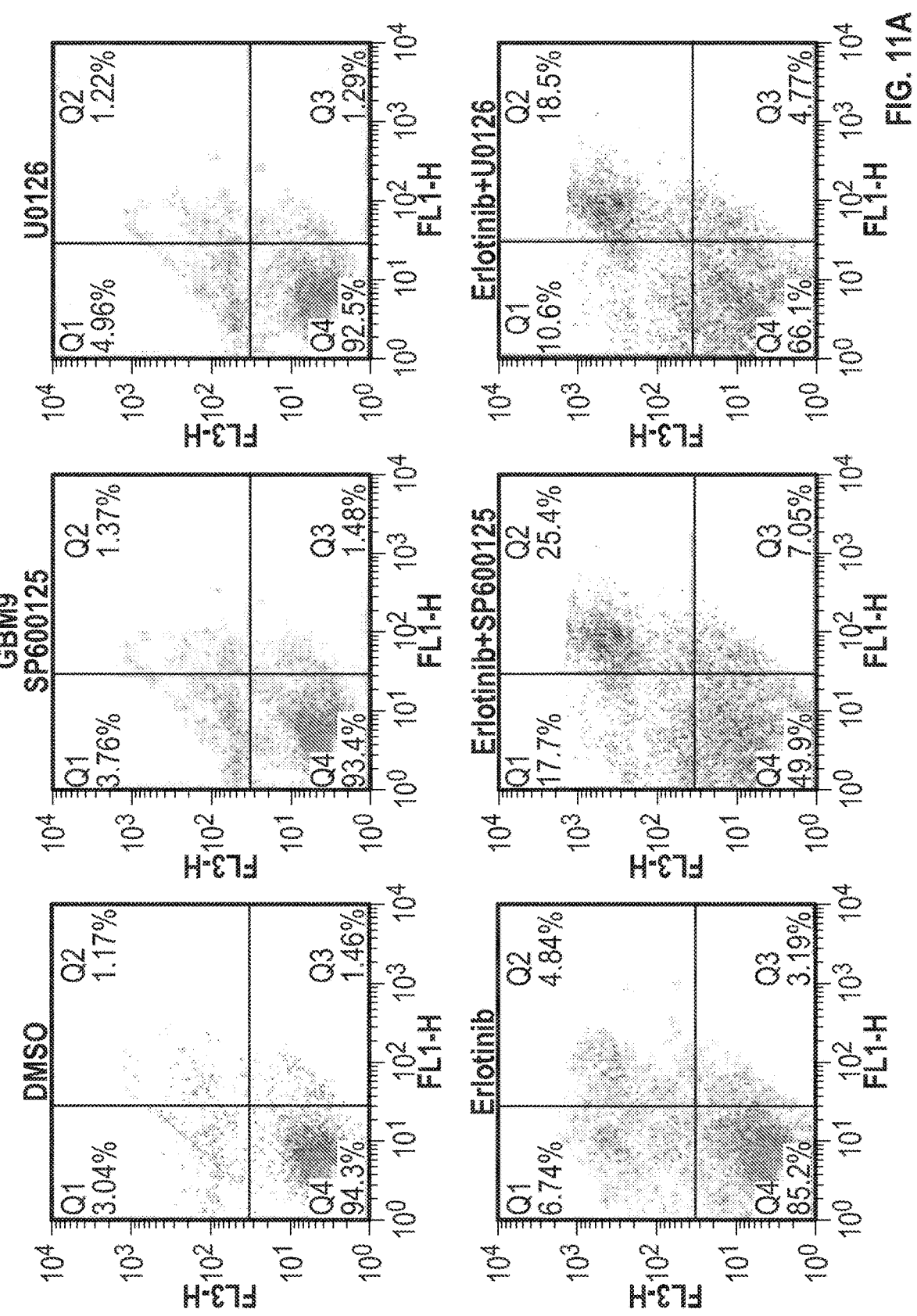
FIG. 11A-FIG. 11D—Inhibition of JNK and ERK Sensitizes Glioma Cells to EGFR Inhibition FIG. 11A-FIG. 11B GBM9 cells were treated with erlotinib and/or JNK inhibitor SP600125 (1 μM), ERK inhibitor U0126 (1 μM) for 72 hours followed by Annexin-FACS assay. Unstained cells represent viable cells. Annexin positive cells are undergoing apoptosis. PI (Propidium iodide) positive cells are undergoing late apoptosis. In "Control" cells are treated with control vehicle (DMSO). The combination treatment decreases the number of viable cells and there is an increase in double stained cells (Annexin+PI Positive).
Figure 11B:
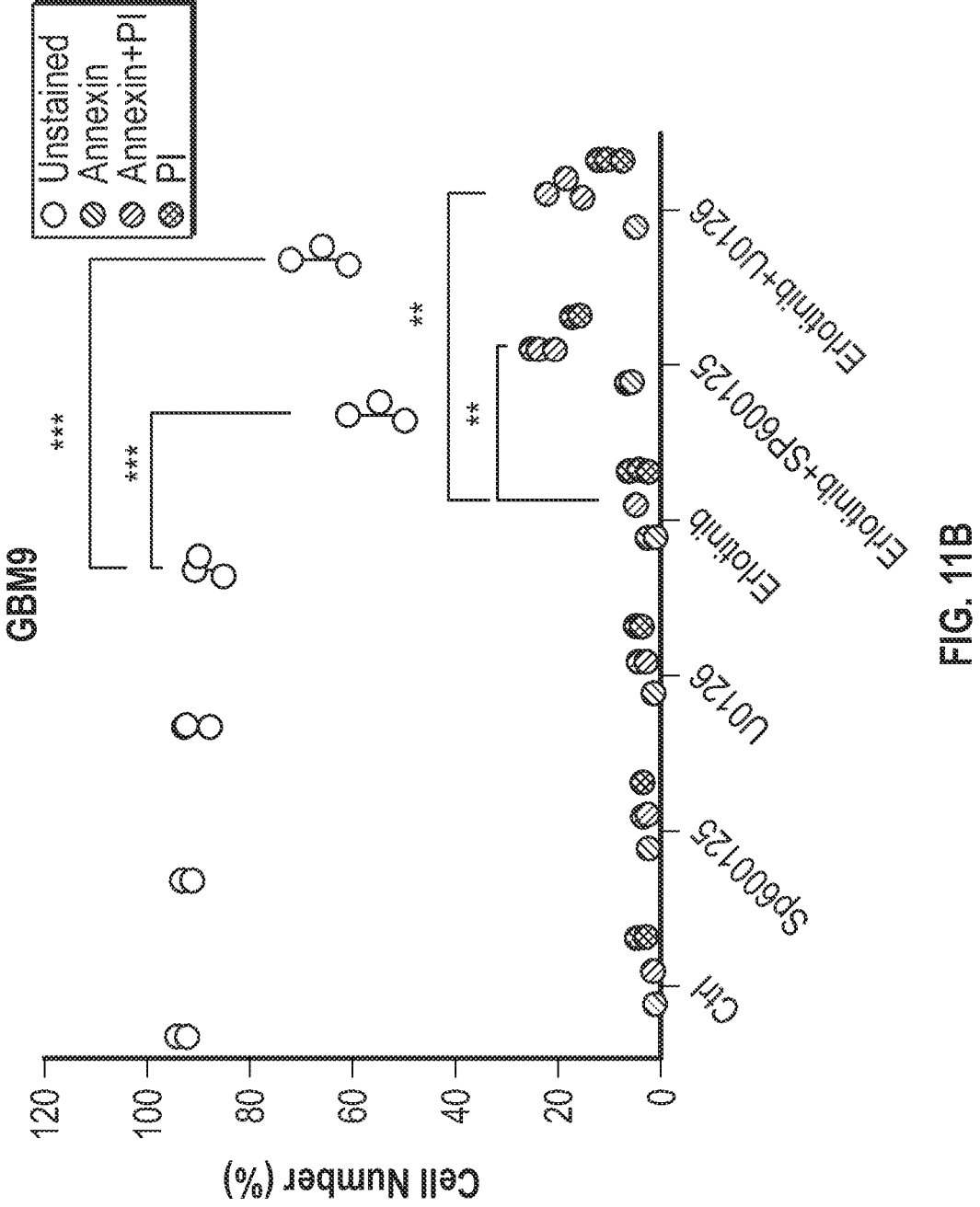
Figure 11C:
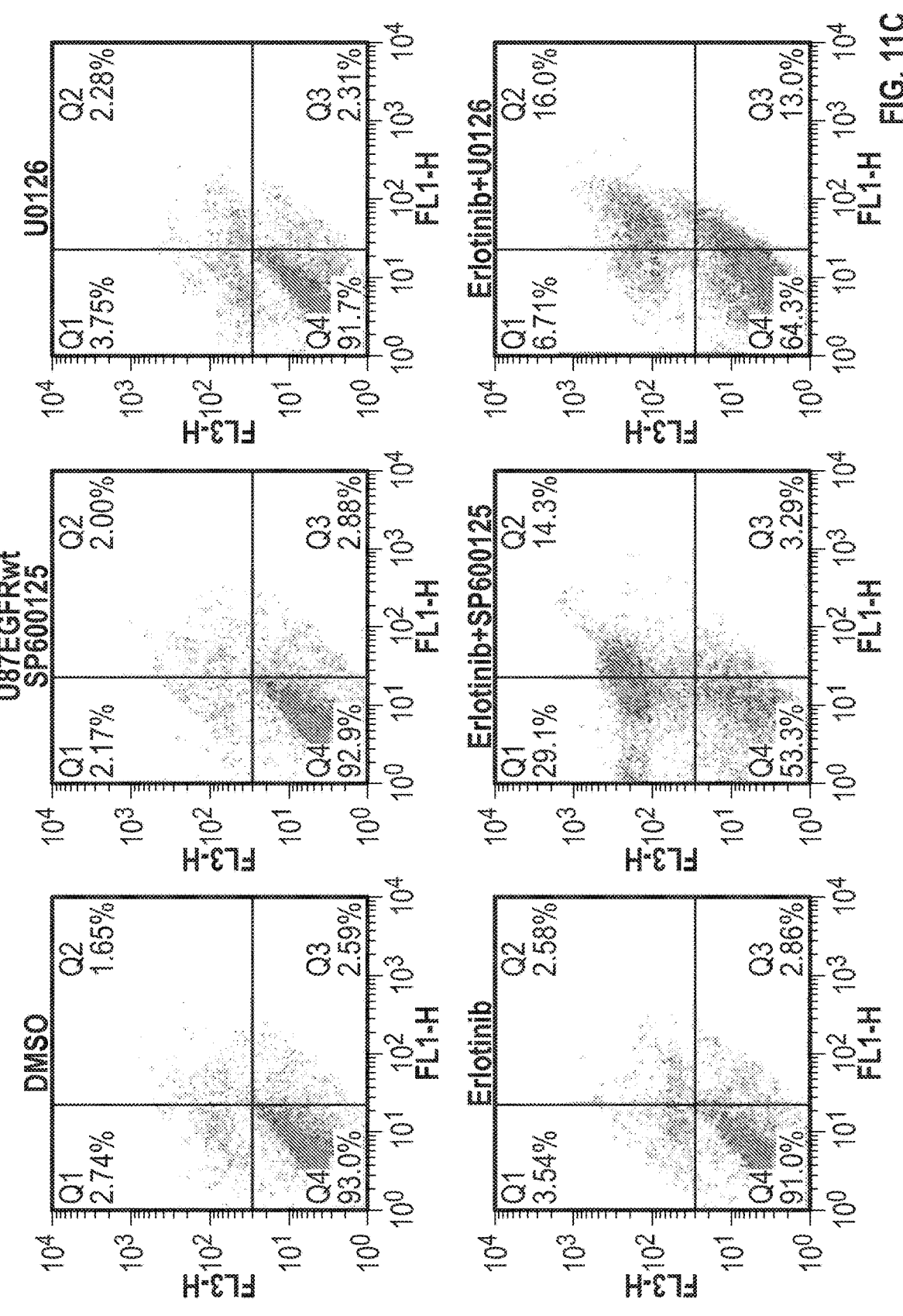
Figure 11D:
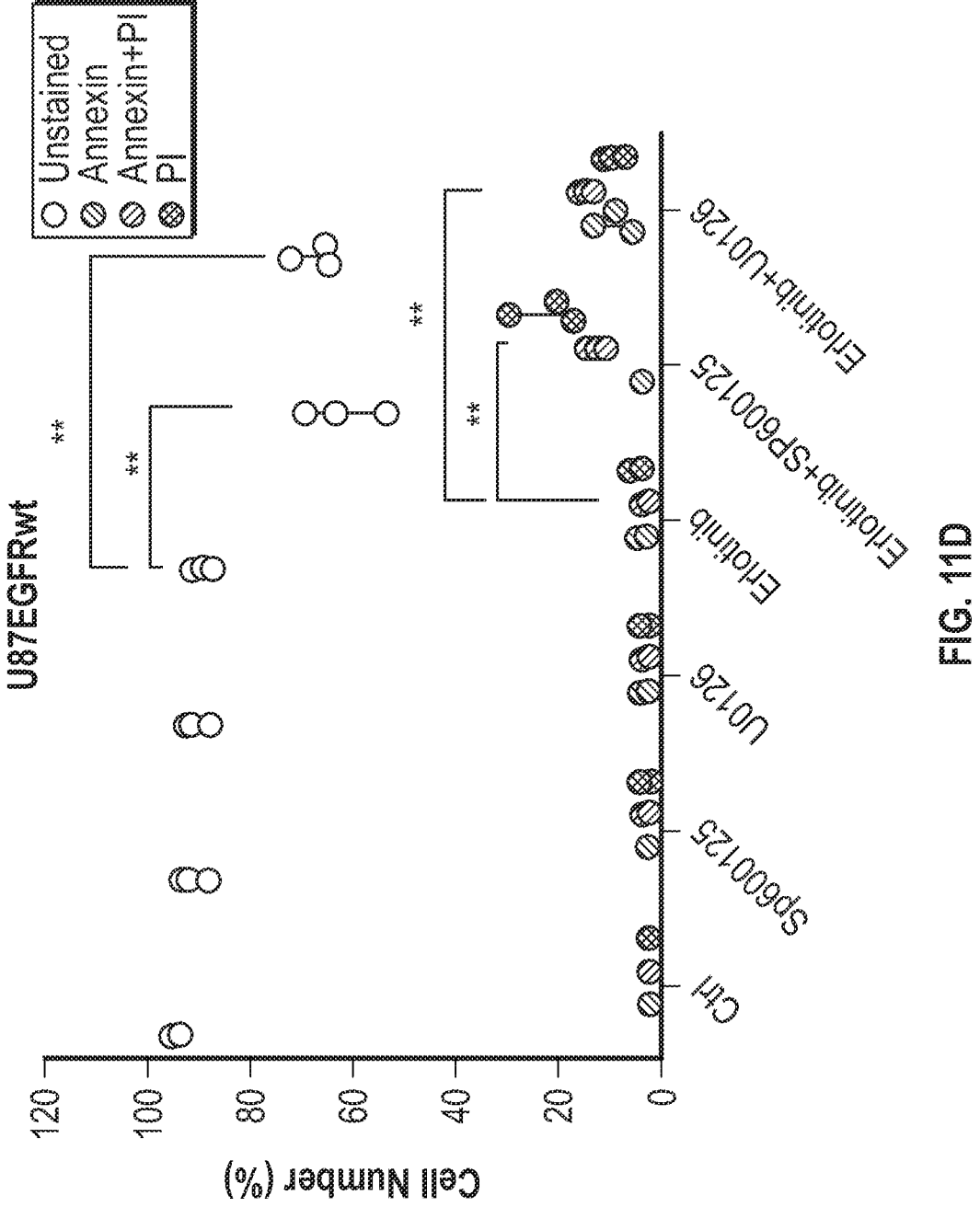
Figure 12A:
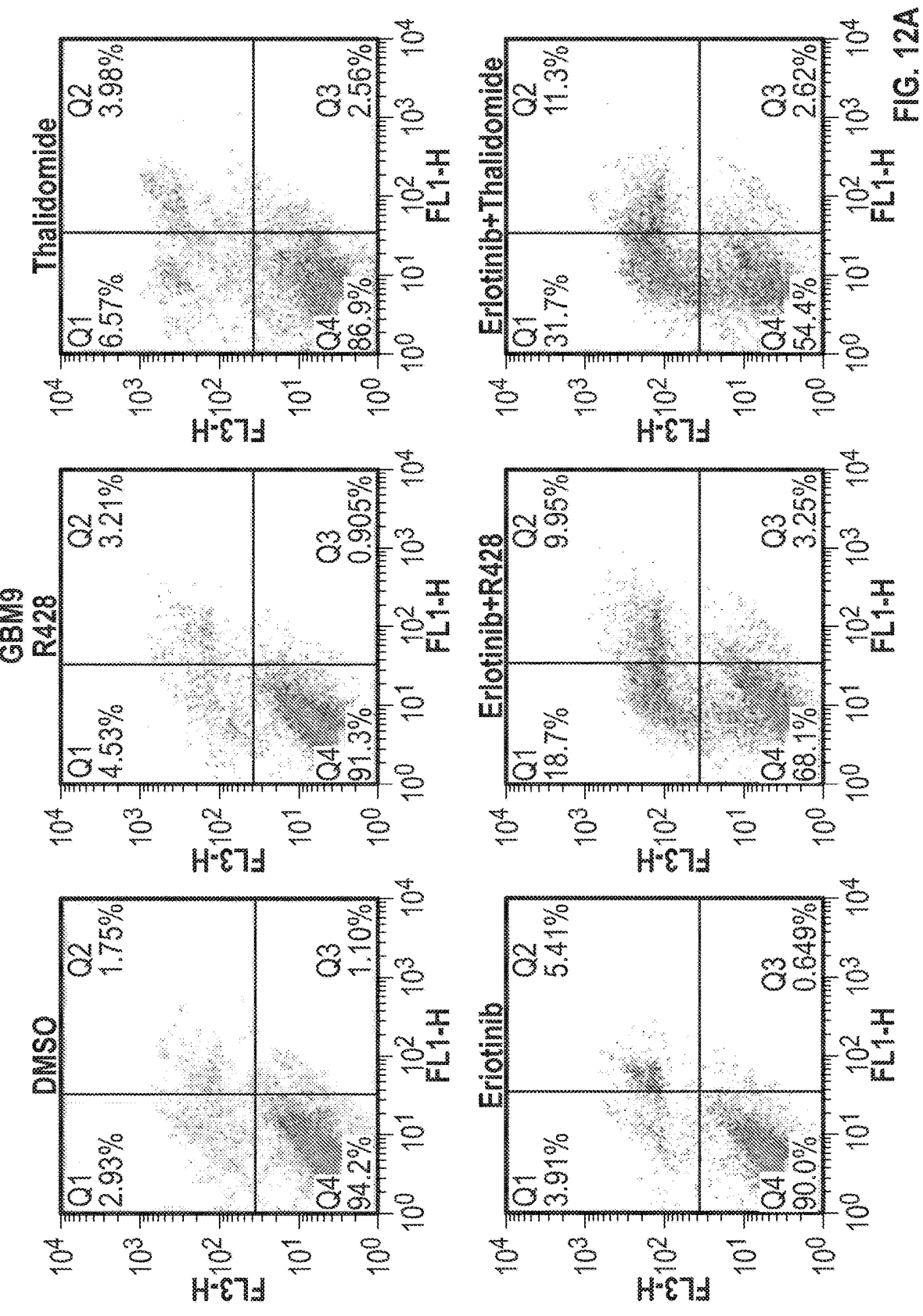
FIG. 12A-FIG. 12D—Axl and TNF Inhibition Renders Glioma Cells Sensitive to EGFR Inhibition FIG. 12A-FIG. 12B GBM9 cells were treated with erlotinib and/or Axl inhibitor R428 (1 μM), Thalidomide (1 μM) for 72 hours followed by Annexin-FACS assay. Unstained cells represent viable cells. Annexin positive cells are undergoing apoptosis. PI (Propidium iodide) positive cells are undergoing late apoptosis. In "Control" cells are treated with control vehicle (DMSO). The combination treatment decreases the number of viable cells and there is an increase in both PI and double stained cells (Annexin+PI Positive).
Figure 12B:
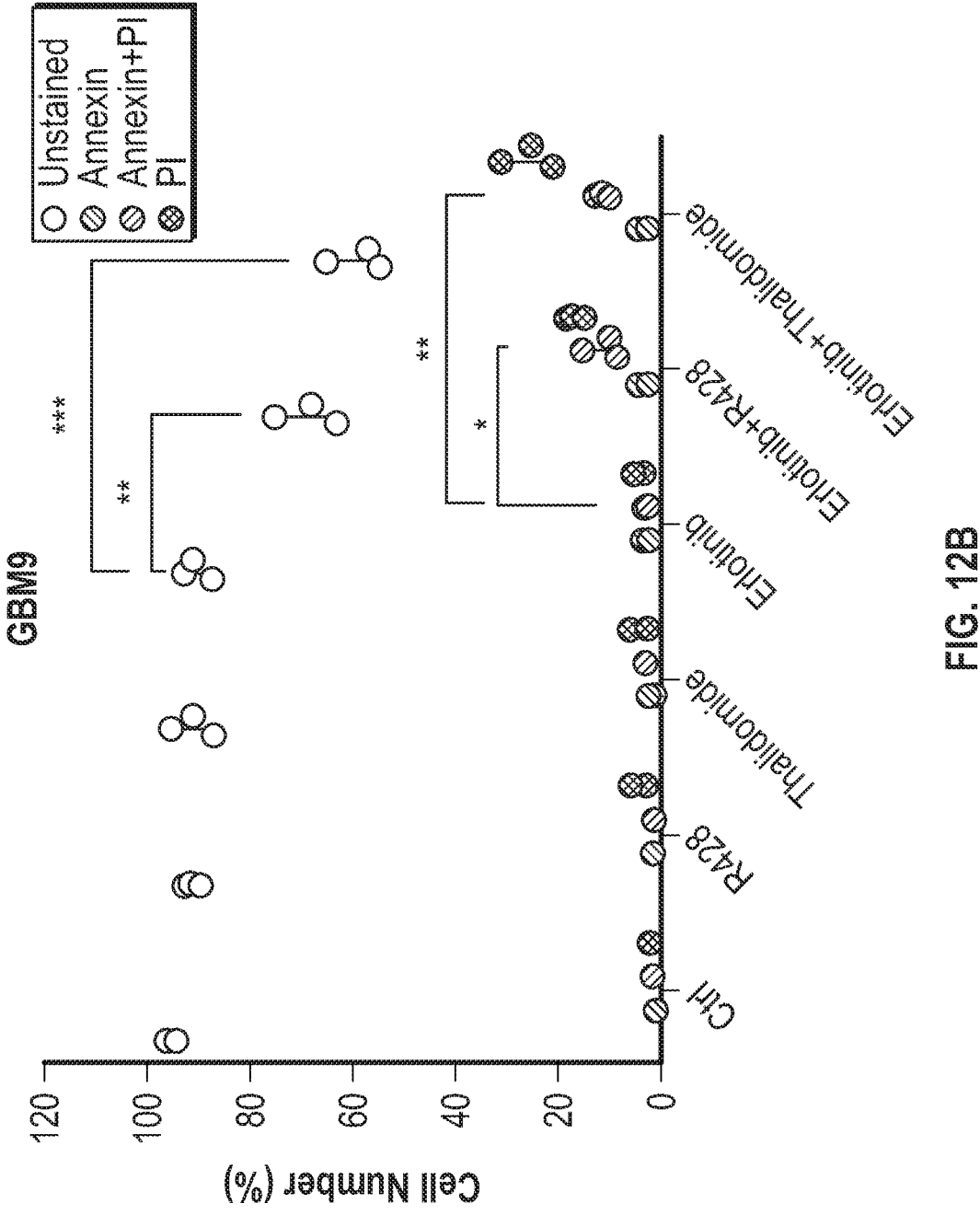
Figure 12C:
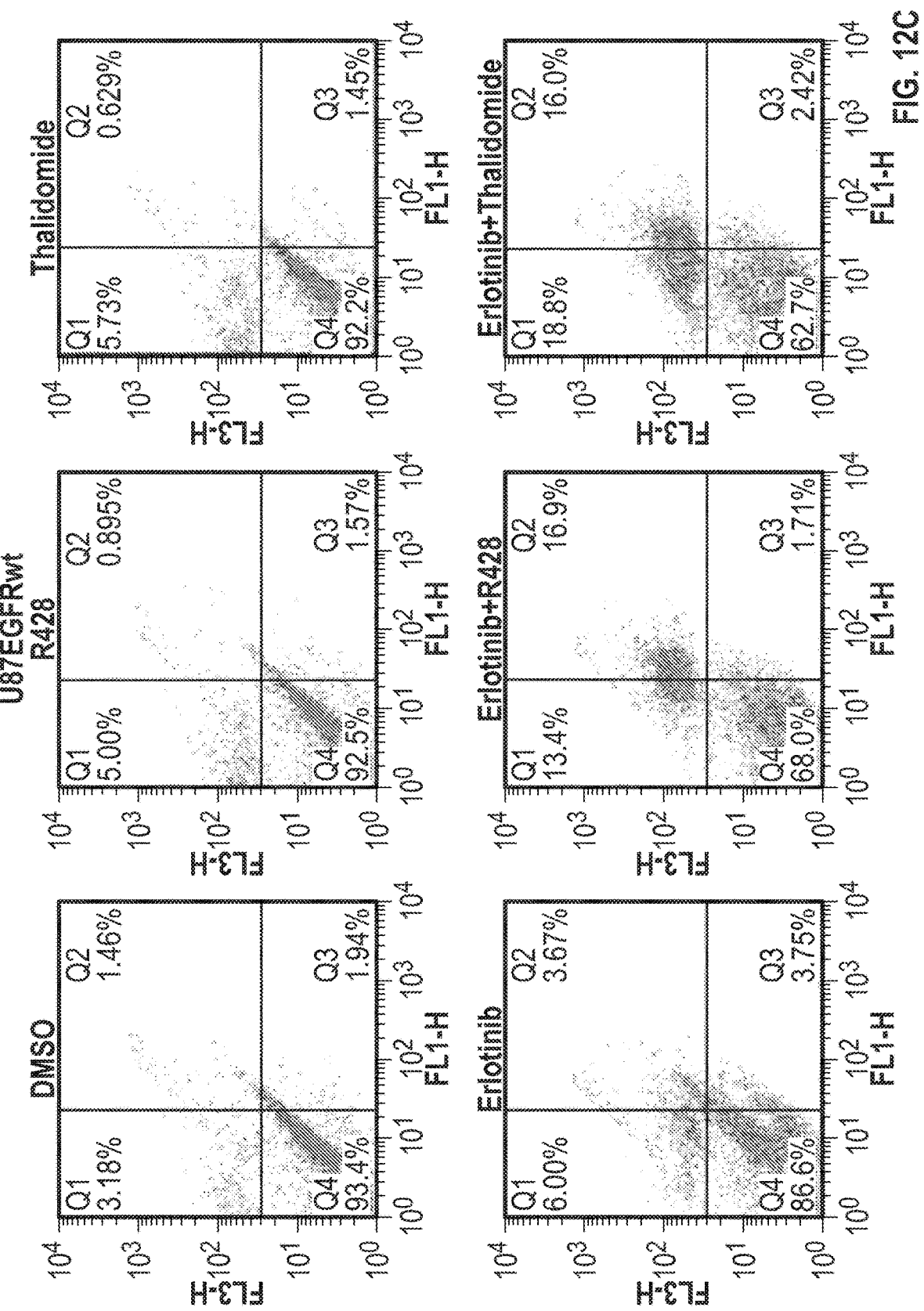
Figure 12D:
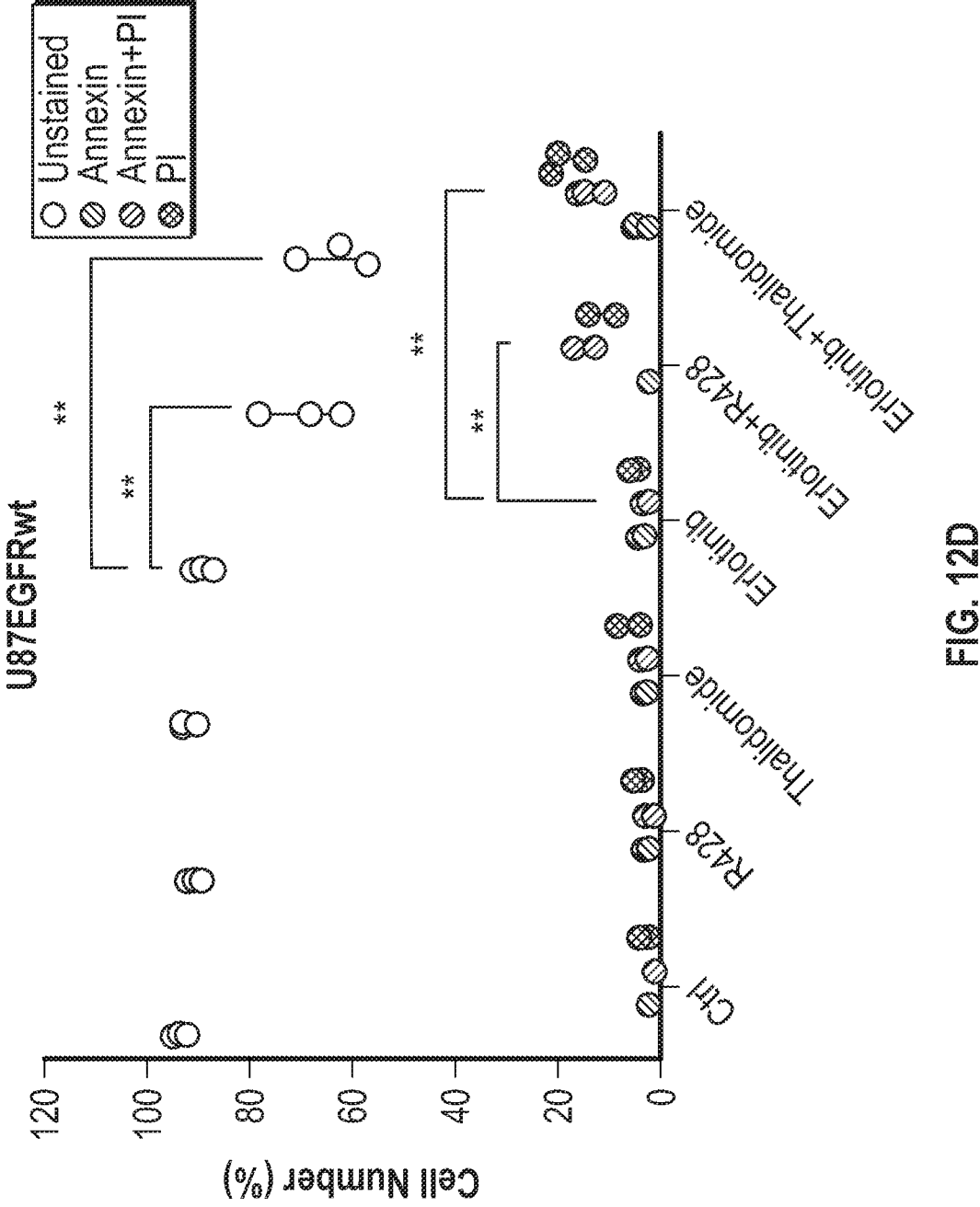

Finally, we examined if inhibition of TNF signaling could render glioma cells sensitive to erlotinib. Indeed, inhibition of TNF signaling with the use of Etanercept (Enbrel) renders patient derived primary GBM neurospheres as well as established GBM cell lines sensitive to the effects of EGFR inhibition as shown in FIG. 6A-C. Similarly, siRNA knockdown of TNFR1 also results in increased sensitivity of cells to EGFR inhibition (FIGS. 6D-F and FIG. 9I). Furthermore, the use of thalidomide, an inhibitor of TNF also had the same effect (FIGS. 6G-I). Thalidomide may inhibit other cytokines, and we confirmed that thalidomide does indeed block the erlotinib-induced increase in TNF secretion in glioma cell lines (FIG. 10A-B). We also confirmed that the use of Enbrel or Thalidomide resulted in an interruption of the erlotinib-induced activation of the JNK-Axl-ERK signaling pathway (FIG. 6J-L). In addition, a neutralizing antibody to TNF also enhanced sensitivity both patient derived and established GBM lines to EGFR inhibition (FIG. 10C-D). In addition, afatinib, an irreversible inhibitor of EGFR kinase, in combination with thalidomide had a similar effect (FIG. 10E-F). Thus, interruption of the adaptive TNF-JNK-Axl-ERK signaling axis at any node, renders resistant glioma cells sensitive to EGFR inhibition.

Conversely, activation of TNF signaling by addition of exogenous TNF, results in protection from cell death induced by EGFR inhibition in patient derived primary GBM neurospheres. In this experiment, we used a erlotinib concentration of 1 μM which induces a significant cell death in these cells. Addition of exogenous TNF protects patient derived primary GBM9 and GBM39 from cell death induced by EGFR inhibition (FIG. 6M-N).

Changes in cell viability were also measured by Flow Cytometry for Annexin V and Caspase 3/7 activation (FIG. 11-14). The data show that glioma cells are undergoing apoptotic cell death when erlotinib is used in combination with Axl, JNK, ERK or TNF inhibition. Finally, cell proliferation was examined by using a cell counting assay. Erlotinib was used in combination with Axl, JNK, ERK or TNF inhibition and the results are shown in FIG. 15, showing significant decreases in cell numbers in response to combined inhibition of EGFR and INK, Axl or ERK.

Inhibiting the Adaptive Response Renders Primarily Resistant Glioma Cells Sensitive in a Mouse Model Erlotinib-induced JNK activation appears to play a central role in orchestrating the adaptive response underlying primary resistance of glioma cells to EGFR inhibition. Thus, we examined the effect of inhibiting JNK in a xenograft model of GBM in athymic mice. The experiment was conducted by injecting patient derived GBM9 neurospheres in the flanks of athymic mice. Once subcutaneous tumors became visible, the mice were divided into control, erlotinib alone, JNK inhibitor (SP600125), or erlotinib+SP600125. erlotinib was administered to animals by oral gavage (50 mg/kg) for 10 days and SP6001125 was administered at a concentration of 40 mg/kg i.p. daily for 10 days. As is shown in FIG. 7A, a combined inhibition of JNK and EGFR strongly inhibits the growth of tumors, whereas SP600125 or erlotinib alone has no significant effect on the growth of tumors.

Next, we undertook an experiment to examine the effect of a combined inhibition of TNF and EGFR. We used thalidomide to inhibit TNF, because thalidomide, is known to penetrate the blood brain barrier and has been previously used in GBM (although not in combination with EGFR inhibition). The experiment was conducted by injecting patient derived GBM9 neurospheres in the flanks of athymic mice. Once subcutaneous tumors became visible, the mice were divided into control, erlotinib alone, thalidomide alone, or erlotinib+thalidomide. Erlotinib was administered to animals by oral gavage (50 mg/kg) daily for 10 days and thalidomide was administered at a concentration of 150 mg/kg i.p. daily for 10 days. As is shown in FIG. 7B, a combined inhibition of TNF and EGFR strongly inhibits the growth of tumors, whereas thalidomide or erlotinib alone has no significant effect on the growth of tumors.

Next we undertook an orthotopic experiment. Patient derived GBM9 cells were implanted intracranially followed by bioluminescence imaging. As we have described recently, GBM9 neurospheres rapidly form tumors in an intracranial model. When tumors became visible on bioluminescence imaging, the mice were divided into four groups and treated with control gavage, erlotinib alone, thalidomide alone, or a combination of erlotinib and thalidomide. While neither erlotinib nor thalidomide alone had a significant effect, the combined treatment resulted in a highly significant improved survival of mice treated with a combination of EGFR and TNF inhibition (FIG. 7C-D). The orthotopic experiment was repeated with afatinib, another EGFR inhibitor with similar results as shown in FIG. 16A-B. In our animal experiments, erlotinib or afatinib was used in combination with thalidomide or SP600125 for a total of 10 days without significant immediate short term toxicity up to the time the mice were sacrificed. The effects of these interventions on the body weight of mice are shown in FIG. 16C-F.

Figures 7A, 7B, 7C, 7D, 7E, 7F, 7G:
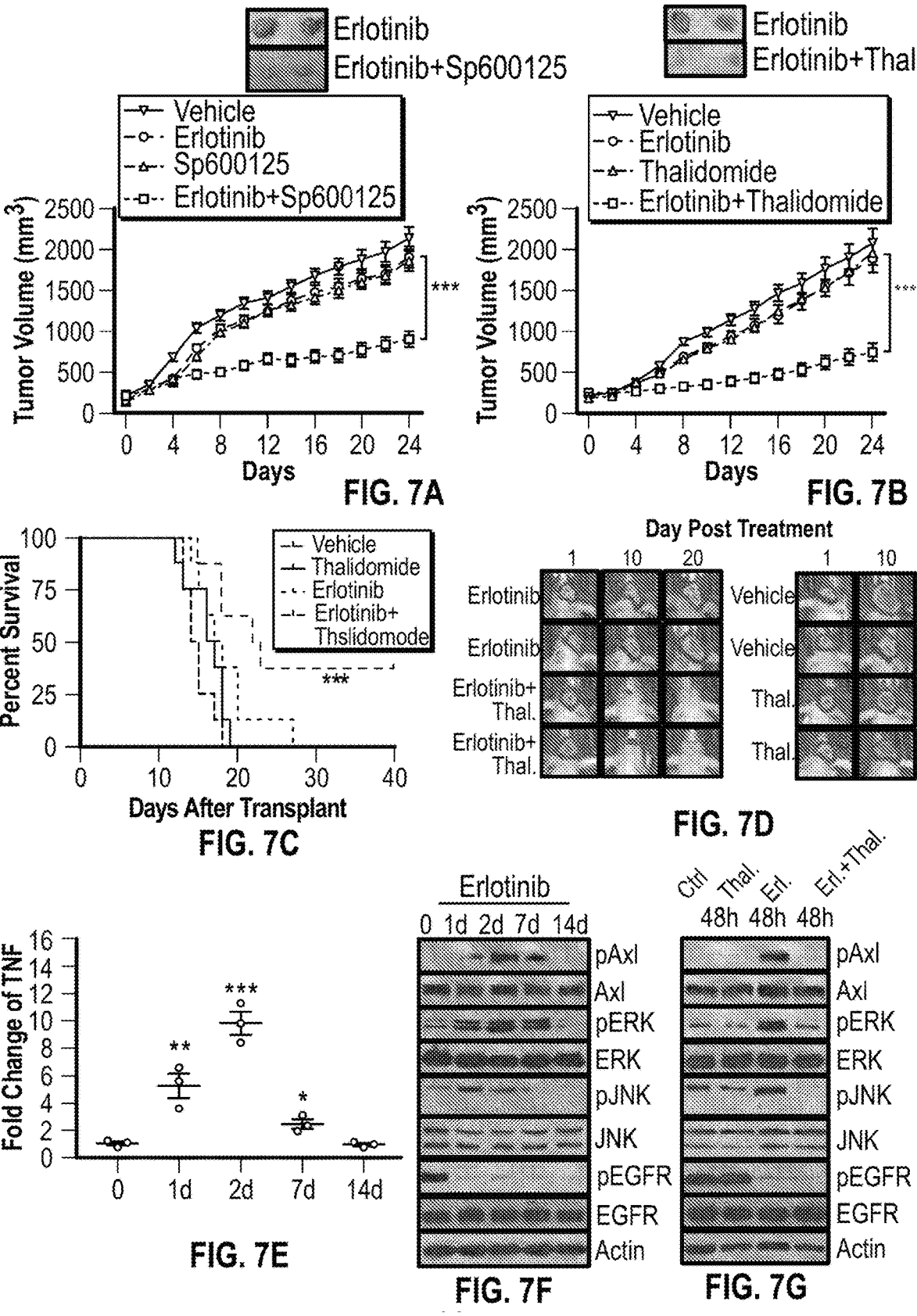
FIG. 7A-FIG. 7G—JNK or TNF Inhibition Sensitizes Mouse Tumors to EGFR Inhibition In Vivo FIG. 7A Treatment of subcutaneous tumors with a combination of erlotinib and SP600125. The tumor growth did not decrease in mice treated erlotinib or SP600125 alone, whereas the combination of erlotinib and SP600125 was found to decrease tumor growth significantly. Unpaired t-test, erlotinib vs erlotinib+SP600125: P=0.0003, t=4.70, d.f.=14, ***P<0.001.

Activation of the JNK-Axl-ERK signaling axis can be detected in intracranial tumors in mice exposed to erlotinib for various time points by Western blot as shown in FIG. 7E-F. We also examined the effect of therapeutic intervention and found that use of a TNF inhibitor (thalidomide) blocked the EGFR inhibition induced upregulation of the TNF-JNK-Axl-ERK signaling axis in intracranial tumors. (FIG. 7G). The temporal profile of this activation is similar to what was noted in the subcutaneous model (FIG. 4G) and shows an increased activation of this pathway peaking at 2-7 days and subsiding by 14 days. We also examined activation of JNK, Axl and ERK by IHC as shown in FIG. 17. The results are consistent with our Western blot results and show that EGFR inhibition leads to activation of the JNK-Axl-ERK signaling axis and administration of a TNF inhibitor (thalidomide) blocks activation of this pathway.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A pharmaceutical composition comprising a therapeutically effective amount of an EGFR inhibitor, one or more additional inhibitors selected from the group consisting of a JNK inhibitor selected from the group consisting of: CEP-1347, SP600125, AS601245, AEG 3482, BI 78D3, CC 401 dihydrochloride, IQ 1S, IQ 3, SR 3576, SU 3327, TCS JNK 5a, and TCS JNK 60, and an ERK inhibitor selected from the group consisting of: U0126, MK-8353, KO-947, AX 15836, BIX 02189, ERK5-IN-1, FR 180204, Pluripotin, TCS ERK 11e, TMCB, XMD 8-92, BVD-523, GDC-099, SCH772984, DEL-22379, LY3214996, Ulixertinib, pyrazolylpyrrole, pyrimidinylpyrrole, FR148083, and FR180289, and a pharmaceutically acceptable carrier, wherein the EGFR inhibitor is selected from the group consisting of afatinib and dacomitinib.

2. The composition of claim 1, wherein the EGFR inhibitor is afatinib and the one or more additional inhibitors is selected from the group consisting of: the JNK inhibitor SP600125 and the ERK inhibitor U0126.

3. The composition of claim 2, wherein the pharmaceutical composition comprises a combination selected from the group of consisting of: afatinib and SP600125; afatinib and U0126; and afatinib, SP600125, and U0126.

4. The composition of claim 1, further comprising an effective amount of a TNF inhibitor.

5. The composition of claim 4, wherein the TNF inhibitor is selected from the group consisting of: thalidomide, pomalidomide, lenalidomide, apremilast, prednisone, etanercept, certolizumab pegol, beclomethasone, betamethasone, cortisone, dexamethasone, hydrocortisone, methylprednisolone, and prednisolone.

6. The composition of claim 4, wherein the TNF inhibitor is selected from the group consisting of: thalidomide, prednisone, and etanercept.

7. The composition of claim 1, wherein the EGFR inhibitor is afatinib.

8. The composition of claim 1, wherein the EGFR inhibitor is capable of crossing the blood-brain barrier.

9. The composition of claim 1, wherein the one or more additional inhibitors is a JNK inhibitor.

10. The composition of claim 9, wherein the JNK inhibitor is SP600125.

11. A pharmaceutical composition comprising a therapeutically effective amount of an EGFR inhibitor, SP600125 and a pharmaceutically acceptable carrier, wherein the EGFR inhibitor is capable of crossing the blood-brain barrier.

12. The composition of claim 11, wherein the EGFR inhibitor is afatinib.

13. The composition of claim 11, further comprising an effective amount of a TNF inhibitor.

14. A pharmaceutical composition comprising a therapeutically effective amount of afatinib, SP600125, and a pharmaceutically acceptable carrier.

15. The composition of claim 14, further comprising a TNF inhibitor selected from the group consisting of thalidomide, prednisone, and etanercept.

* * * * *